US012686860B2

(12) United States Patent
Li et al.

(10) Patent No.: US 12,686,860 B2
(45) Date of Patent: Jul. 21, 2026

(54) SOLUBLE ACE2 PROTEIN, FUSION PROTEINS THEREOF WITH AN FC DOMAIN, AND METHODS OF TREATMENT OF AN ACE2-RELATED DISEASE

(71) Applicants: HUAHUI HEALTH LTD., Beijing (CN); NATIONAL INSTITUTE OF BIOLOGICAL SCIENCES, BEIJING, Beijing (CN)

(72) Inventors: Wenhui Li, Beijing (CN); Yonghe Qi, Beijing (CN); Jianhe Chen, Beijing (CN); Jianhua Sui, Beijing (CN); Juan Liu, Beijing (CN); Fengfeng Mao, Beijing (CN); Ximing Liu, Beijing (CN)

(73) Assignees: HUAHUI HEALTH LTD., Beijing (CN); NATIONAL INSTITUTE OF BIOLOGICAL SCIENCES, BEIJING, Beijing (CN)

( * ) Notice: Subject to any disclaimer, the term of this patent is extended or adjusted under 35 U.S.C. 154(b) by 912 days.

(21) Appl. No.: 17/802,499

(22) PCT Filed: Feb. 27, 2021

(86) PCT No.: PCT/CN2021/078343
§ 371 (c)(1),
(2) Date: Aug. 25, 2022

(87) PCT Pub. No.: WO2021/170131
PCT Pub. Date: Sep. 2, 2021

(65) Prior Publication Data
US 2023/0348880 A1 Nov. 2, 2023

(30) Foreign Application Priority Data
Feb. 27, 2020 (CN) .......................... 202010124368.4

(51) Int. Cl.
A61K 38/43 (2006.01)
A61K 47/68 (2017.01)
(Continued)

(52) U.S. Cl.
CPC .............. *C12N 9/485* (2013.01); *A61K 38/43* (2013.01); *A61K 47/6815* (2017.08); *A61P 1/00* (2018.01);
(Continued)

(58) Field of Classification Search
CPC ........... C12N 9/485; C12Y 304/17023; C07K 2317/52; C07K 2319/30; C07K 2319/32;
(Continued)

(56) References Cited

U.S. PATENT DOCUMENTS

| | | | |
|---|---|---|---|
| 2010/0150923 A1 | 6/2010 | Jiang et al. | |
| 2012/0100140 A1* | 4/2012 | Reyes ................ | C07K 16/2875 435/69.6 |
| 2023/0250410 A1* | 8/2023 | Tsai ....................... | C12N 9/485 424/94.63 |

FOREIGN PATENT DOCUMENTS

| | | |
|---|---|---|
| CN | 1884303 A | 12/2006 |
| CN | 102639147 A | 8/2012 |

(Continued)

OTHER PUBLICATIONS

Tokuriki et al, 2009, Current Opinion in Structural Biology. 19: 596-604.*

(Continued)

*Primary Examiner* — Zachary C Howard
(74) *Attorney, Agent, or Firm* — Kilpatrick Townsend & Stockton LLP

(57) ABSTRACT

A soluble ACE2 and a truncated form thereof, a fusion protein thereof and preparation methods therefor. A soluble ACE2 and a truncated form thereof, as well as a use of the (Continued)

ACE2-hFc          ACE2-hFc5              ACE2-hFc5-L309C          ACE2-hFc-ACE2  ACE2-ACE2-hFc
                  (pentamer/hexamer)    (pentamer/hexamer)

fusion protein in the preparation of a drug for an ACE2-related disease.

13 Claims, 12 Drawing Sheets

Specification includes a Sequence Listing.

(51) Int. Cl.

| | |
|---|---|
| *A61P 1/00* | (2006.01) |
| *A61P 1/16* | (2006.01) |
| *A61P 9/04* | (2006.01) |
| *A61P 11/00* | (2006.01) |
| *A61P 13/12* | (2006.01) |
| *A61P 31/14* | (2006.01) |
| *A61P 37/02* | (2006.01) |
| *C12N 9/48* | (2006.01) |
| *C12N 15/63* | (2006.01) |

(52) U.S. Cl.
CPC *A61P 1/16* (2018.01); *A61P 9/04* (2018.01); *A61P 11/00* (2018.01); *A61P 13/12* (2018.01); *A61P 31/14* (2018.01); *A61P 37/02* (2018.01); *C12Y 304/17023* (2013.01); *C07K 2317/52* (2013.01); *C07K 2319/30* (2013.01); *C07K 2319/32* (2013.01); *C12N 15/63* (2013.01)

(58) Field of Classification Search
CPC ....... A61K 38/43; A61K 47/6815; A61P 1/00; A61P 1/16; A61P 9/04; A61P 11/00; A61P 13/12
See application file for complete search history.

(56) References Cited

FOREIGN PATENT DOCUMENTS

| | | |
|---|---|---|
| CN | 112375149 A | 2/2021 |
| JP | 2008540600 A | 11/2008 |
| JP | 2015501291 A | 1/2015 |
| KR | 20100040809 A | 4/2010 |
| WO | 2009023306 A2 | 2/2009 |
| WO | 2011008974 A2 | 1/2011 |
| WO | 2011073692 A1 | 6/2011 |
| WO | 2018140456 A1 | 8/2018 |
| WO | 2022090469 A2 | 5/2022 |

OTHER PUBLICATIONS

Moore et al, 2004. Journal of Virology. 10628-10635.*
Tipnis et al, 2000. Journal of Biological Chemistry. 275(43). 33238-33243.*
Czajkowsky et al, 2012. EMBO Mol Med. 4: 1015-1028.*
Qian Kewen et al., "Ig-like ACE2 protein therapeutics: A revival in development during the COVID-19 pandemic", MABS, vol. 12, No. 1, Jul. 7, 2020.
Mao Xiaoniu et al., "A novel biparatopic hybrid antibody-ACE2 fusion that blocks SARS-CoV-2 infection: implications for therapy", MABS, vol. 12, No. 1, Aug. 17, 2020.
Wrapp Daniel et al.,"Cryo-EM structure of the 2019-nCoV spike in the prefusion conformation", Science, vol. 367,No. 6483, Feb. 19, 2020 (Feb. 19, 2020), pp. 1260-1263.
Liu Juan et al., "An IgM-like inhalable ACE2 fusion protein broadly neutralizes SARS-CoV-2 variants", Nature Communications, vol. 14, No. 1,Aug. 25, 2023.
Kryukov A.I., Turovskii A.B., Kolbanova I.G et al., "Guidelines for the acute respiratory viral infection treatment", RMJ. 2019; 8(I): 46-50.
Pakula AA and Sauer RT, "Genetic analysis of protein stability and function", Anna. Rev. Genet, 1989, vol. 23, pp. 289-310.
Ozlem Keskin et al., "A new, structurally nonredundant, diverse data set of protein—protein interfaces and its implications", Protein Sci., 2004, vol. 13, N.4, 1043-1055.
Czajkowsky, D.M., "Fc-fusion proteins: new developments and future perspectives", EMBO Mol Med., 4/10, pp. 1015-1028, Jul. 26, 2012.
Lei Changhai, et al., "Potent neutralization of 2019 novel coronavirus by recombinant ACE2-Ig", bioRxiv 2020.02.01.929976.
Mekhaiel, D., Czajkowsky, D., Andersen, J. et al. "Polymeric human Fc-fusion proteins with modified effector functions". Sci Rep 1, 124 (2011).
Han et al., "Effects of Spike Gene Mutation on Infectivity of SARS-CoV BJ01 Strain", Bulletin of the Academy of Military Medical Sciences, vol. 32, No. 2, Apr. 30, 2008, pp. 106-120.
Hannah et al., "Functional Analysis of Potential Cleavage Sites in the MERS-Coronavirus Spike Protein", Scientific Reports, No. 8, Article 16597, Nov. 9, 2018, pp. 1-11.
Kruse , "Therapeutic Strategies in an Outbreak Scenario to Treat the Novel Coronavirus Originating in Wuhan, China", F1000 Research, vol. 9, No. 72, Version 2, Jan. 31, 2020, pp. 1-14.
Application No. PCT/CN2021/078343 , International Search Report and Written Opinion, Mailed on May 28, 2021, 17 pages.

* cited by examiner

Green: Spike protein expressed cell    Red: hACE2 expressed cell    Blue: nucleus

Fig. 4

SARS-CoV2 S protein and Furin site

MFVFLVLLPLVSSQCVNLTTRTQLPPAYTNSFTRGVYYPDKVFRSSVLHSTQDL
FLPFFSNVTWFHAIHVSGTNGTKRFDNPVLPFNDGVYFASTEKSNIIRGWIFGT
TLDSKTQSLLIVNNATNVVIKVCEFQFCNDPFLGVYYHKNNKSWMESEFRVY
SSANNCTFEYVSQPFLMDLEGKQGNFKNLREFVFKNIDGYFKIYSKHTPINLV
RDLPQGFSALEPLVDLPIGINITRFQTLLALHRSYLTPGDSSSGWTAGAAAYYV
GYLQPRTFLLKYNENGTITDAVDCALDPLSETKCTLKSFTVEKGIYQTSNFRV
QPTESIVRFPNITNLCPFGEVFNATRFASVYAWNRKRISNCVADYSVLYNSASFS
TFKCYGVSPTKLNDLCFTNVYADSFVIRGDEVRQIAPGQTGKIADYNYKLPDD
FTGCVIAWNSNNLDSKVGGNYNYLYRLFRKSNLKPFERDISTEIYQAGSTPCN
GVEGFNCYFPLQSYGFQPTNGVGYQPYRVVVLSFELLHAPATVCGPKKSTNL
VKNKCVNFNFNGLTGTGVLTESNKKFLPFQQFGRDIADTTDAVRDPQTLEILDI
TPCSFGGVSVITPGTNTSNQVAVLYQDVNCTEVPVAIHADQLTPTWRVYSTGS
NVFQTRAGCLIGAEHVNNSYECDIPIGAGICASYQTQTNSPRRAR-
SVASQSIIAYTMSLGAENSVAYSNNSIAIPTNFTISVTTEILPVSMTKTSVDCTM
YICGDSTECSNLLLQYGSFCTQLNRALTGIAVEQDKNTQEVFAQVKQIYKTPPI
KDFGGFNFSQILPDPSKPSKRSFIEDLLFNKVTLADAGFIKQYGDCLGDIAARD
LICAQKFNGLTVLPPLLTDEMIAQYTSALLAGTITSGWTFGAGAALQIPFAMQ
MAYRFNGIGVTQNVLYENQKLIANQFNSAIGKIQDSLSSTASALGKLQDVVNQ
NAQALNTLVKQLSSNFGAISSVLNDILSRLDKVEAEVQIDRLITGRLQSLQTYV
TQQLIRAAEIRASANLAATKMSECVLGQSKRVDFCGKGYHLMSFPQSAPHGV
VFLHVTYVPAQEKNFTTAPAICHDGKAHFPREGVFVSNGTHWFVTQRNFYEP
QIITTDNTFVSGNCDVVIGIVNNTVYDPLQPELDSFKEELDKYFKNHTSPDVDL
GDISGINASVVNIQKEIDRLNEVAKNLNESLIDLQELGKYEQYIKWPWYIWLG
FIAGLIAIVMVTIMLCCMTSCCSCLKGCCSCGSCCKFDEDDSEPVLKGVKLHY
T-

Fig. 5

SARS-CoV2 S protein with mutated Furin cleavage site

MFVFLVLLPLVSSQCVNLTTRTQLPPAYTNSFTRGVYYPDKVFRSSVLHSTQDL
FLPFFSNVTWFHAIHVSGTNGTKRFDNPVLPFNDGVYFASTEKSNIIRGWIFGT
TLDSKTQSLLIVNNATNVVIKVCEFQFCNDPFLGVYYHKNNKSWMESEFRVY
SSANNCTFEYVSQPFLMDLEGKQGNFKNLREFVFKNIDGYFKIYSKHTPINLV
RDLPQGFSALEPLVDLPIGINITRFQTLLALHRSYLTPGDSSSGWTAGAAAYYV
GYLQPRTFLLKYNENGTITDAVDCALDPLSETKCTLKSFTVEKGIYQTSNFRV
QPTESIVRFPNITNLCPFGEVFNATRFASVYAWNRKRISNCVADYSVLYNSASFS
TFKCYGVSPTKLNDLCFTNVYADSFVIRGDEVRQIAPGQTGKIADYNYKLPDD
FTGCVIAWNSNNLDSKVGGNYNYLYRLFRKSNLKPFERDISTEIYQAGSTPCN
GVEGFNCYFPLQSYGFQPTNGVGYQPYRVVVLSFELLHAPATVCGPKKSTNL
VKNKCVNFNFNGLTGTGVLTESNKKFLPFQQFGRDIADTTDAVRDPQTLEILDI
TPCSFGGVSVITPGTNTSNQVAVLYQDVNCTEVPVAIHADQLTPTWRVYSTGS
NVFQTRAGCLIGAEHVNNSYECDIPIGAGICASYQTQTNSP<u>SRAS</u>SVASQSIIAY
TMSLGAENSVAYSNNSIAIPTNFTISVTTEILPVSMTKTSVDCTMYICGDSTECS
NLLLQYGSFCTQLNRALTGIAVEQDKNTQEVFAQVKQIYKTPPIKDFGGFNFS
QILPDPSKPSKRSFIEDLLFNKVTLADAGFIKQYGDCLGDIAARDLICAQKFNG
LTVLPPLLTDEMIAQYTSALLAGTITSGWTFGAGAALQIPFAMQMAYRFNGIG
VTQNVLYENQKLIANQFNSAIGKIQDSLSSTASALGKLQDVVNQNAQALNTL
VKQLSSNFGAISSVLNDILSRLDKVEAEVQIDRLITGRLQSLQTYVTQQLIRAA
EIRASANLAATKMSECVLGQSKRVDFCGKGYHLMSFPQSAPHGVVFLHVTYV
PAQEKNFTTAPAICHDGKAHFPREGVFVSNGTHWFVTQRNFYEPQIITTDNTF
VSGNCDVVIGIVNNTVYDPLQPELDSFKEELDKYFKNHTSPDVDLGDISGINA
SVVNIQKEIDRLNEVAKNLNESLIDLQELGKYEQYIKWPWYIWLGFIAGLIAIV
MVTIMLCCMTSCCSCLKGCCSCGSCCKFDEDDSEPVLKGVKLHYT.

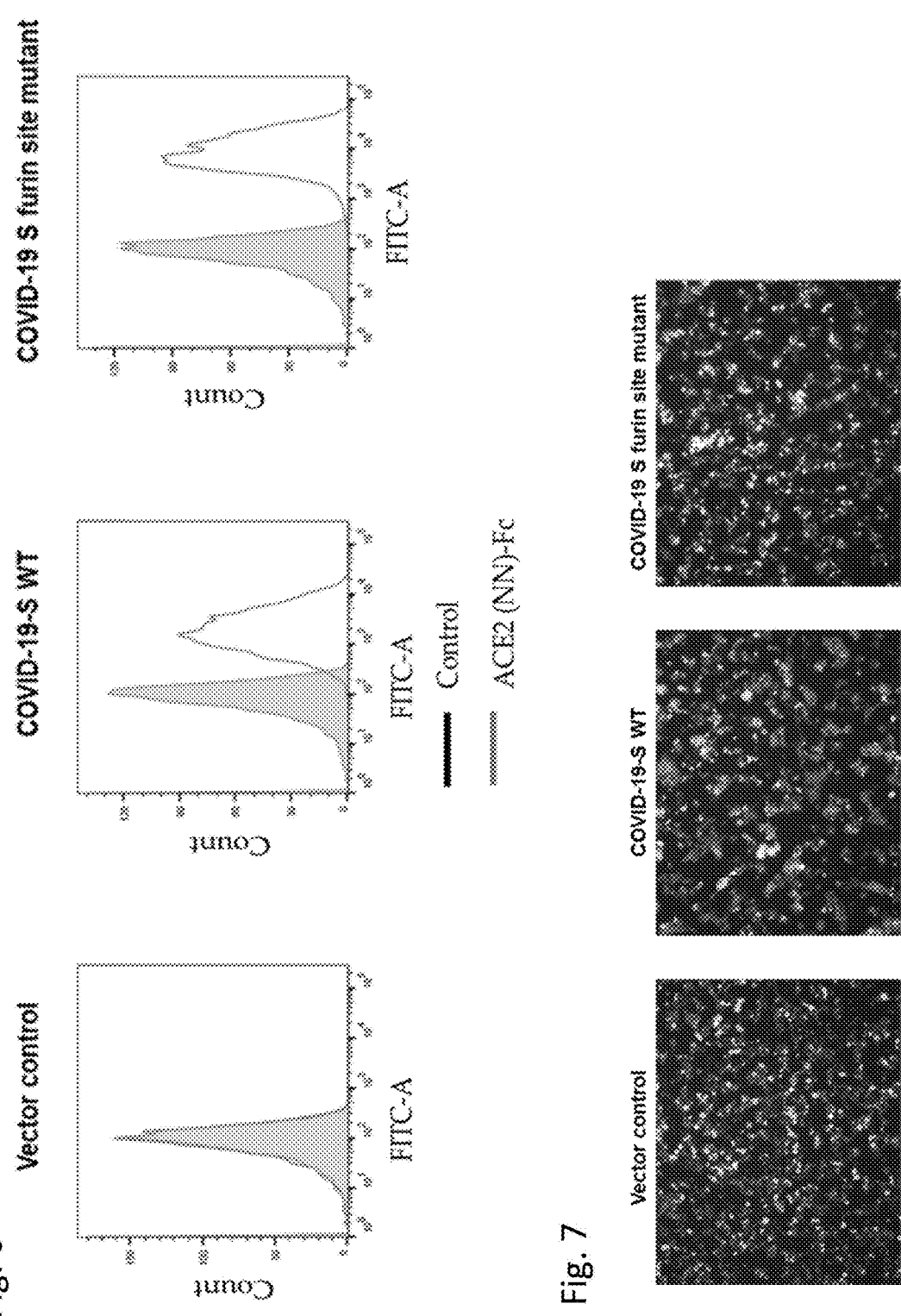

Fig. 8

Wide-type Ectdomain (1-1208 aa) of SARS-CoV2 S protein

MFVFLVLLPLVSSQCVNLTTRTQLPPAYTNSFTRGVYYPDKVFRSSVLHSTQDLFLPFFSNVTWFHAIHVS
GTNGTKRFDNPVLPFNDGVYFASTEKSNIIRGWIFGTTLDSKTQSLLIVNNATNVVIKVCEFQFCNDPFLG
VYYHKNNKSWMESEFRVYSSANNCTFEYVSQPFLMDLEGKQGNFKNLREFVFKNIDGYFKIYSKHTPIN
LVRDLPQGFSALEPLVDLPIGINITRFQTLLALHRSYLTPGDSSSGWTAGAAAYYVGYLQPRTFLLKYNEN
GTITDAVDCALDPLSETKCTLKSFTVEKGIYQTSNFRVQPTESIVRFPNITNLCPFGEVFNATRFASVYAWN
RKRISNCVADYSVLYNSASFSTFKCYGVSPTKLNDLCFTNVYADSFVIRGDEVRQIAPGQTGKIADYNYK
LPDDFTGCVIAWNSNNLDSKVGGNYNYLYRLFRKSNLKPFERDISTEIYQAGSTPCNGVEGFNCYFPLQS
YGFQPTNGVGYQPYRVVVLSFELLHAPATVCGPKKSTNLVKNKCVNFNFNGLTGTGVLTESNKKFLPFQ
QFGRDIADTTDAVRDPQTLEILDITPCSFGGVSVITPGTNTSNQVAVLYQDVNCTEVPVAIHADQLTPTWR
VYSTGSNVFQTRAGCLIGAEHVNNSYECDIPIGAGICASYQTQTNSPRRARSVASQSIIAYTMSLGAENSV
AYSNNSIAIPTNFTISVTTEILPVSMTKTSVDCTMYICGDSTECSNLLLQYGSFCTQLNRALTGIAVEQDKN
TQEVFAQVKQIYKTPPIKDFGGFNFSQILPDPSKPSKRSFIEDLLFNKVTLADAGFIKQYGDCLGDIAARD
LICAQKFNGLTVLPPLLTDEMIAQYTSALLAGTITSGWTFGAGAALQIPFAMQMAYRFNGIGVTQNVLYE
NQKLIANQFNSAIGKIQDSLSSTASALGKLQDVVNQNAQALNTLVKQLSSNFGAISSVLNDILSRLDKVE
AEVQIDRLITGRLQSLQTYVTQQLIRAAEIRASANLAATKMSECVLGQSKRVDFCGKGYHLMSFPQSAP
HGVVFLHVTYVPAQEKNFTTAPAICHDGKAHFPREGVFVSNGTHWFVTQRNFYEPQIITTDNTFVSGNC
DVVIGIVNNTVYDPLQPELDSFKEELDKYFKNHTSPDVDLGDISGINASVVNIQKEIDRLNEVAKNLNESL
IDLQELGKYEQ

Ectdomain (1-1208 aa) of SARS-CoV2 S protein with mutated Furin site

MFVFLVLLPLVSSQCVNLTTRTQLPPAYTNSFTRGVYYPDKVFRSSVLHSTQDLFLPFFSNVTWFHAIHVS
GTNGTKRFDNPVLPFNDGVYFASTEKSNIIRGWIFGTTLDSKTQSLLIVNNATNVVIKVCEFQFCNDPFLG
VYYHKNNKSWMESEFRVYSSANNCTFEYVSQPFLMDLEGKQGNFKNLREFVFKNIDGYFKIYSKHTPIN
LVRDLPQGFSALEPLVDLPIGINITRFQTLLALHRSYLTPGDSSSGWTAGAAAYYVGYLQPRTFLLKYNEN
GTITDAVDCALDPLSETKCTLKSFTVEKGIYQTSNFRVQPTESIVRFPNITNLCPFGEVFNATRFASVYAWN
RKRISNCVADYSVLYNSASFSTFKCYGVSPTKLNDLCFTNVYADSFVIRGDEVRQIAPGQTGKIADYNYK
LPDDFTGCVIAWNSNNLDSKVGGNYNYLYRLFRKSNLKPFERDISTEIYQAGSTPCNGVEGFNCYFPLQS
YGFQPTNGVGYQPYRVVVLSFELLHAPATVCGPKKSTNLVKNKCVNFNFNGLTGTGVLTESNKKFLPFQ
QFGRDIADTTDAVRDPQTLEILDITPCSFGGVSVITPGTNTSNQVAVLYQDVNCTEVPVAIHADQLTPTWR
VYSTGSNVFQTRAGCLIGAEHVNNSYECDIPIGAGICASYQTQTNSPSRASSVASQSIIAYTMSLGAENSV
AYSNNSIAIPTNFTISVTTEILPVSMTKTSVDCTMYICGDSTECSNLLLQYGSFCTQLNRALTGIAVEQDKN
TQEVFAQVKQIYKTPPIKDFGGFNFSQILPDPSKPSKRSFIEDLLFNKVTLADAGFIKQYGDCLGDIAARD
LICAQKFNGLTVLPPLLTDEMIAQYTSALLAGTITSGWTFGAGAALQIPFAMQMAYRFNGIGVTQNVLYE
NQKLIANQFNSAIGKIQDSLSSTASALGKLQDVVNQNAQALNTLVKQLSSNFGAISSVLNDILSRLDKVE
AEVQIDRLITGRLQSLQTYVTQQLIRAAEIRASANLAATKMSECVLGQSKRVDFCGKGYHLMSFPQSAP
HGVVFLHVTYVPAQEKNFTTAPAICHDGKAHFPREGVFVSNGTHWFVTQRNFYEPQIITTDNTFVSGNC
DVVIGIVNNTVYDPLQPELDSFKEELDKYFKNHTSPDVDLGDISGINASVVNIQKEIDRLNEVAKNLNESL
IDLQELGKYEQ

Fig. 14
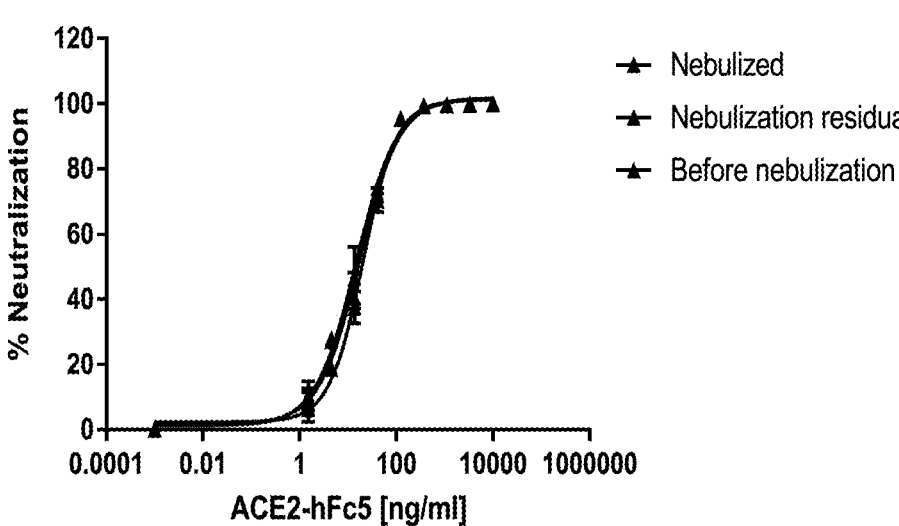
Fig. 15
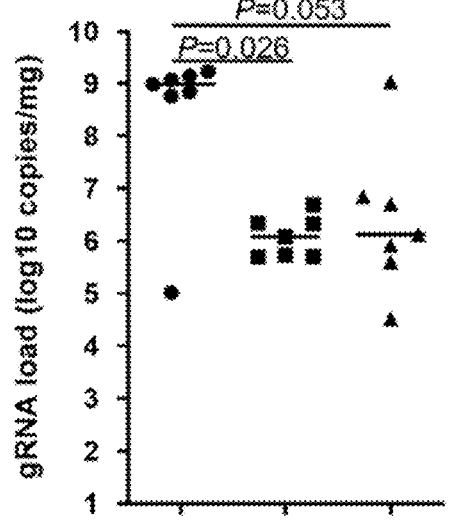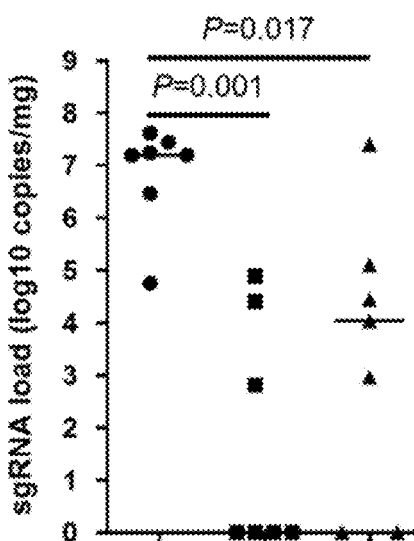

SOLUBLE ACE2 PROTEIN, FUSION PROTEINS THEREOF WITH AN FC DOMAIN, AND METHODS OF TREATMENT OF AN ACE2-RELATED DISEASE

PRIORITY CLAIM

The application is a U.S. 371 of International Application No. PCT/CN2021/078343 filed Feb. 27, 2021, which claims priority to CN Patent Application No. 202010124368.4 filed on Feb. 27, 2020, the contents of which are hereby incorporated herein by reference in their entirety.

REFERENCE TO AN ELECTRONIC SEQUENCE LISTING

The instant application contains a Sequence Listing which has been submitted electronically in ASCII format and is hereby incorporated by reference in its entirety. Said ASCII copy, created on Jan. 13, 2023, is named WO21508HHUS-Sequence-listing.TXT and is 127,219 bytes in size.

TECHNICAL FIELD

The present disclosure relates to a soluble ACE2 and fusion proteins thereof, and uses thereof.

BACKGROUND ART

In December 2019, a pneumonia caused by infection of a new coronavirus, severe acute respiratory syndrome coronavirus 2 (SARS-CoV2) broke out, and spread rapidly around the world. As of February 2021, the number of infected people in the world had reached more than 100 million, with a mortality rate of about 2.2%. It not only triggered a global health crisis but also had extensive and far-reaching impacts on society, economy and the like.

Coronaviruses belong to the order Torovirus, the family Coronaviridae and the genus Coronaviridae. Coronaviruses refer to a type of viruses with an envelope and a linear single-strand of positive-sense RNA, and are a large group of viruses that are widespread in nature. In patients, they cause diseases that have different clinical symptoms ranging from common cold to severe lung infection. In the past two decades, the coronaviruses have caused two large-scale epidemics, i.e., Severe Acute Respiratory Syndrome (SARS) in 2002/2003 and Middle East Respiratory Syndrome (MERS) in 2012. Since the end of 2019, the new coronavirus (SARS-CoV2) epidemic has far exceeded SARS and MERS epidemics, in terms of not only the epidemic scope and cumulative number of infected people, but also the number of deaths.

The viral genome of SARS-CoV2 is highly similar to RaTG13 strain isolated from a bat (Chinese chrysanthemum bat) discovered in Yunnan, China in 2013, with a sequence identity of up to 96.2% (Zhou et al., 2020). Thus, it can be inferred that the origin of this new coronavirus is consistent with those of the coronaviruses that caused SARS and MERS. That is, they all originated from bats. The pathway leading to the epidemic of this new coronavirus, SARS-CoV2, in humans is likely to be consistent with SARS and MERS. The virus came from bats, evolved and amplified in intermediate hosts (e.g., animals that have closer relationship with humans), and finally infected humans. The virus continued to evolve in humans and spread rapidly, resulting in the outbreak of the virus infection. In the nature, coronaviruses similar to SARS have existed for a long time in bats from many parts of the world, and most of them cannot infect humans.

Nonetheless, some "natural focus" diseases may accidentally infect humans through another intermediate host. The "SARS" epidemic of March 2002 and the outbreak of SARS-CoV2 infection after 17 years show that, as long as the natural host exists, there is the possibility that other pathogenic coronavirus infections occur in future.

In November 2020, the FDA authorized the emergency use of two monoclonal antibodies, i.e., bamlanivimab of Eli Lilly and the combination of casirivimab and imdevimab of Regeneron, for the treatments of SARS-CoV2 infection. Both of the antibodies were approved for non-hospitalized adults and children over 12 years old with mild to moderate SARS-CoV2 symptoms and at risk of disease exacerbations. It is generally difficult for monoclonal antibodies to balance high efficiency and broad-spectrum activity. With the worldwide epidemic of the SARS-CoV2, variants have been produced and will continue to be produced under selection pressures such as for further adaptation to human hosts and human immunity. The variants may have changes in the antigenic sites that render the existing neutralizing antibodies ineffective.

The coronavirus SARS-CoV, and the animal viruses related to it all use angiotensin-converting enzyme 2 (ACE2) as a receptor to invade and infect target cells. The surface of the coronavirus has multiple S proteins in the form of trimers which have high affinity with ACE2. Thus, the multivalent high-affinity binding between S proteins and ACE2 is required to be blocked at the same time, in order to achieve effective neutralization of the viruses. A soluble receptor, which is formed by fusing the extracellular region of ACE2 with the constant region of an antibody, has a similar action mechanism to neutralizing antibodies, and can block the infection by variants that have mutations but still use ACE2 as a receptor. Soluble ACE2 fusion proteins can be developed as therapeutic drugs, which have broad-spectrum neutralization ability and will not be restricted by virus mutations. Such fusion proteins not only can be used as therapeutic drugs for SARS-CoV-2 infections, but also can deal with similar epidemics that may occur in the future.

SUMMARY OF THE INVENTION

A soluble ACE2, a soluble ACE2 having mutation(s) in an enzyme active center (NN), and an ACE2-Fc fusion protein having the soluble ACE2 or the soluble ACE2 having mutation(s) in the enzyme active center (NN) and an Fc fragment from human IgG1, can effectively neutralize SARS-CoV2 and SARS-CoV, and block the formation of multinucleated syncytia, which can be induced by the binding of a spike (S) protein (containing a Furin protease cleavage site) of SARS-CoV2 to its receptor human ACE2.

In a first aspect, the present disclosure provides a soluble ACE2 or truncated form thereof. The soluble ACE2 or truncated form thereof may comprise or consist of an extracellular domain of ACE2, or a fragment thereof that retains an ability of binding to a coronavirus.

In some embodiments, the soluble ACE2 or truncated form thereof may comprise a metalloprotease domain (19-615aa) in the extracellular region of human ACE2. In some embodiments, the soluble ACE2 or truncated form thereof may comprise a metalloprotease domain (1-740aa) in the extracellular region of human ACE2. In some embodiments, the soluble ACE2 or truncated form thereof may comprise Q24, T27, F28, D30, K31, H34, E37, D38, Y41, Q42, L45, M82, Y83, Q325, E329, N330, K353, G354, D355, R357 and R393 of human ACE2, especially K31 and K353.

In some embodiments, the soluble ACE2 or truncated form thereof may comprise human binding to the coronavirus.

The soluble ACE2 or truncated form thereof can effectively neutralize a virus that uses ACE2 as a host-binding receptor. The virus may comprise SARS-CoV, HCoV-NL63 or SARS-CoV2.

In some embodiments, the soluble ACE2 or truncated form thereof may comprise ACE2 containing a mutation in an enzyme active center, or a truncated form thereof. Preferably, the ACE2 containing a mutation in the enzyme active center, or truncated form thereof, may be a human soluble ACE2 or a truncated form thereof having H374N and/or H378N mutation(s) at position(s) 374 and/or 378 (ACE2-NN).

The soluble ACE2 or truncated form thereof may be a soluble ACE2 or truncated form thereof that has an enzymatic activity of ACE2.

Preferably, the soluble ACE2 or truncated form thereof may be glycosylated, which, preferably, may be glycosylated at position(s) 53, 90, 103, 322, 432, 546 and/or 690 at the N-terminal of human ACE2.

Preferably, the soluble ACE2 or truncated form thereof may have an amino acid sequence as shown by SEQ ID NO: 1.

Preferably, the soluble ACE2 or truncated form thereof may have an amino acid sequence as shown by SEQ ID NO: 2.

In a second aspect, the present disclosure provides an ACE2-Fc fusion protein which is obtained by fusing the soluble ACE2 or truncated form thereof with an antibody Fc domain.

In some embodiments, the soluble ACE2 or truncated form thereof may comprise or consist of the extracellular domain of ACE2, or a fragment thereof that retains the ability of binding to a coronavirus.

In some embodiments, the soluble ACE2 or truncated form thereof may comprise a metalloprotease domain (19-615aa) in the extracellular region of human ACE2. The soluble ACE2 or truncated form thereof may comprise a metalloprotease domain (1-740aa) in the extracellular region of human ACE2. The soluble ACE2 or truncated form thereof may comprise Q24, T27, F28, D30, K31, H34, E37, D38, Y41, Q42, L45, M82, Y83, Q325, E329, N330, K353, G354, D355, R357 and R393 of human ACE2, especially K31 and K353.

In some embodiments, the soluble ACE2 or truncated form thereof may comprise human ACE2, or any homolog or ortholog thereof, or a fragment thereof that has the ability of binding to the coronavirus.

The soluble ACE2 or truncated form thereof can effectively neutralize a virus that uses the ACE2 as a host-binding receptor. The virus may comprise SARS-CoV, HCoV-NL63 or SARS-CoV2.

In some embodiments, the soluble ACE2 or truncated form thereof may comprise ACE2 containing a mutation in the enzyme active center, or a truncated form thereof. Preferably, the ACE2 containing a mutation in the enzyme active center or truncated form thereof may comprise a human soluble ACE2 or truncated form thereof (ACE2-NN) having H374N and/or H378N mutation(s) at position(s) 374 and/or 378.

The soluble ACE2 or truncated form thereof may comprise a soluble ACE2 or truncated form thereof that has the enzymatic activity of ACE2.

Preferably, the soluble ACE2 or truncated form thereof may be glycosylated, which, preferably, may be glycosylated at position(s) 53, 90, 103, 322, 432, 546 and/or 690 at the N-terminal of human ACE2.

Preferably, the soluble ACE2 or truncated form thereof may have an amino acid sequence as shown by SEQ ID NO: 1.

Preferably, the soluble ACE2 or a truncated form thereof may have an amino acid sequence as shown by SEQ ID NO: 2.

The soluble ACE2 or truncated form thereof can effectively neutralize a virus that uses the ACE2 as a host-binding receptor. The virus may comprise SARS-CoV, HCoV-NL63 or SARS-CoV2.

In some embodiments, the antibody may be an IgG antibody. The antibody may be a human IgG, such as IgG1, IgG2, IgG3 or IgG4, preferably IgG1. The antibody Fc domain may be an antibody Fc-domain containing two heavy chain Fc domains of the antibody. Preferably, each of the heavy chain Fc domains has a hinge region at its N-terminal. Preferably, each of the heavy chain Fc domains may comprise a CH3 domain derived from IgG1, IgG2, IgG3 or IgG4. Preferably, each of the heavy chain Fc domains may comprise CH2 and CH3 domains derived from IgG1, IgG2, IgG3 or IgG4. The Fc domains can promote the dimerization of two ACE2 domains.

The soluble ACE2 or truncated form thereof may be linked to the C-terminal end of the heavy chain Fc domain, or to the N-terminal end of the heavy chain Fc domain.

In some embodiments, 2n (n is 1, 2 or 3) of the soluble ACE2s or truncated forms thereof may be linked to the C- and/or N-terminal end(s) of the two heavy chain Fc domains.

In some embodiments, two soluble ACE2s or truncated forms thereof may be linked respectively to the N-terminal end of the two heavy chain Fc domains to form a dimer. Alternatively, two soluble ACE2s or truncated forms thereof may be linked to the C-terminal end of the two heavy chain Fc domains to form a dimer.

In some embodiments, two soluble ACE2s or truncated forms thereof may be linked respectively to the N-terminal end of the two heavy chain Fc domains, and other two soluble ACE2s or truncated forms thereof may be linked respectively to the C-terminal ends of the two heavy chain Fc domains, thereby forming a tetrameric ACE2-Fc fusion protein. Further, each of the two soluble ACEs or truncated forms thereof at the N-terminal of the tetrameric ACE2-Fc fusion protein further, at its N-terminal end, links to a soluble ACE2 or truncated form thereof in tandem, thereby forming a hexameric ACE2-Fc fusion protein. The soluble ACE2s or truncated forms thereof may be linked in tandem via a linker. The linker may be a cysteine AAA linker. Alternatively, each of the two soluble ACEs or truncated forms thereof at the C-terminal of the tetrameric ACE2-Fc fusion protein further, at its C-terminal end, links to a soluble ACE2 or a truncated form thereof in tandem, thereby forming a hexameric ACE2-Fc fusion protein. The soluble ACE2s or truncated forms thereof are linked in tandem via a linker. The linker may be a cysteine AAA linker.

In some embodiments, each of the two heavy chain Fc domains may be, at its N-terminal end, linked to two soluble ACE2s or truncated forms thereof which are linked in tandem, thereby forming a tetrameric ACE2-Fc fusion protein. The two soluble ACE2s or truncated forms thereof are linked in tandem via a linker. The linker may be a cysteine AAA linker. Further, the soluble ACE2 or truncated form thereof may be, at each of the N-terminal ends of the tetrameric ACE2-Fc fusion protein, further linked to a soluble ACE2 or a truncated form thereof in tandem, thereby forming a hexameric ACE2-Fc fusion protein. The soluble ACE2s or truncated forms thereof are linked in tandem via a linker. The linker may be a cysteine AAA linker. Alternatively, each of the two heavy chain Fc domains of the tetrameric ACE2-Fc fusion protein may be, at its C-terminal end, linked to a soluble ACE2 or truncated form thereof, thereby forming a hexameric ACE2-Fc fusion protein.

Alternatively, each of the two heavy chain Fc domains may be, at its C-terminal end, linked to two soluble ACE2s or truncated forms thereof which are linked in tandem, thereby forming a tetrameric ACE2-Fc fusion protein. The two soluble ACE2s or truncated forms thereof may be linked in tandem via a linker. The linker may be a cysteine AAA linker. Further, each of the two heavy chain Fc domains of the tetrameric ACE2-Fc fusion protein may be, at its N-terminal end, linked to a soluble ACE2 or truncated form thereof, thereby forming a hexameric ACE2-Fc fusion protein.

Preferably, the ACE2-Fc fusion protein may be actually a dimeric ACE2-Fc fusion protein, wherein one ACE2 truncated form and one heavy chain Fc domain may have an amino acid sequence as shown by SEQ ID NO: 3.

Preferably, one ACE2 truncated form and one heavy chain Fc domain in the ACE2-Fc fusion protein may have an amino acid sequence as shown by SEQ ID NO: 4.

Preferably, the ACE2-Fc fusion protein may further comprise a signal peptide, preferably a CD33 signal peptide.

Preferably, one ACE2 truncated form and one heavy chain Fc domain in the ACE2-Fc fusion protein may have an amino acid sequence as shown by SEQ ID NO: 5.

Preferably, one ACE2 truncated form and one heavy chain Fe domain in the ACE2-Fc fusion protein may have an amino acid sequence as shown by SEQ ID NO: 6.

Preferably, in the tetrameric ACE2-Fc fusion protein, one ACE2 truncated form may be linked to one heavy chain Fc domain which is further linked to one ACE2 (ACE2-Fc-ACE2), resulting in an amino acid sequence as shown by SEQ ID NO: 13.

Preferably, in the tetrameric ACE2-Fc fusion protein, the two ACE2s or truncated forms thereof may be linked to one heavy chain Fc domain (ACE2-ACE2-Fc), resulting in an amino acid sequence as shown by SEQ ID NO: 14.

The ACE2-Fc fusion protein can effectively neutralize a virus that uses ACE2 as a host-binding receptor. The virus may comprise SARS-CoV, HCoV-NL63 or SARS-CoV2.

The ACE2-Fc fusion protein of the present disclosure can improve the half-life and yield of the soluble ACE2, and meet, to the greatest extent, the needs of rapid process development and emergency use.

In a third aspect, the present disclosure provides an Fc fusion protein multimer ACE2-hFc(n) of the soluble ACE2 or truncated form thereof, which may comprise n polypeptide monomer units, each of the polypeptide monomer units may be a dimer in which two soluble ACE2s or truncated forms thereof are linked to the N-terminal ends of the two heavy chain Fc domains respectively, and the n polypeptide monomer units are assembled into the multimer via a tail located at each of the C-terminal of the antibody Fc-domains.

In some embodiments, each of the heavy chain Fc domains in each polypeptide monomer unit may be, at its C-terminal end, linked with a tail. Therefore, each of two heavy chain Fc domains of the polypeptide monomer unit is, at its C-terminal end, linked with one tail, and n polypeptide monomer units have a total of 2n tails, which are connected to each other to form a closed circular multimer.

The tail may have any suitable amino acid sequences and may be a tail found in naturally occurring antibodies. Alternatively, it may be a modified tail that differs from the native tail in length and/or composition. Alternatively, the tail may be an artificially synthesized tail suitable for multimerization, such as a tail consisting of a flexible Cys-sequence of a suitable length. Alternatively, the tail may comprise a variant or fragment from a natural sequence, such as an IgM tail PTLYNVSLVMSDTAGTCY (SEQ ID NO: 15) or an IgA tail PTHVNVSVVMAEVDGTCY (SEQ ID NO: 16). Alternatively, a variant from IgM or IgA tail usually may have an amino acid sequence comprising 8, 9, 10, 11, 12, 13, 14, 15, 16, 17 or 18 amino acids from IgM tail PTLYNVSLVMSDTAGTCY (SEQ ID NO: 15) or IgA tail PTHVNVSVVMAEVDGTCY (SEQ ID NO: 16). The tail may also be a hybrid IgM/IgA tail. Preferably, the tail may comprise an amino acid sequence TGKPT-LYNVSLVMSDTAGTCY (SEQ ID NO: 17).

In some embodiments, the soluble ACE2 or truncated form thereof may comprise or consist of the extracellular domain of ACE2, or a fragment thereof that retains the ability of binding to the coronavirus.

In some embodiments, the soluble ACE2 or truncated form thereof may comprise a metalloprotease domain (19-615aa) in the extracellular region of human ACE2. The soluble ACE2 or truncated form thereof may comprise a metalloprotease domain (1-740aa) in the extracellular region of human ACE2. The soluble ACE2 or truncated form thereof may comprise Q24, T27, F28, D30, K31, H34, E37, D38, Y41, Q42, L45, M82, Y83, Q325, E329, N330, K353, G354, D355, R357 and R393 of human ACE2, especially K31 and K353.

In some embodiments, the soluble ACE2 or truncated form thereof may comprises human ACE2 or any homolog or ortholog thereof, or a fragment thereof that retains the ability of binding to the coronavirus.

The soluble ACE2 or truncated form thereof can effectively neutralize a virus that uses the ACE2 as a host-binding receptor. The virus may comprise SARS-CoV, HCoV-NL63 or SARS-CoV2.

In some embodiments, the soluble ACE2 or truncated form thereof may comprise ACE2 containing a mutation in an enzyme active center, or a truncated form thereof. Preferably, the ACE2 containing a mutation in an enzyme active center, or a truncated form thereof, may comprise human soluble ACE2 or truncated form thereof (ACE2-NN) having H374N and/or H378N mutation(s) at position 374 and/or position 378.

The soluble ACE2 or truncated form thereof may comprise a soluble ACE2 or truncated form thereof that has an enzymatic activity of ACE2.

Preferably, the soluble ACE2 or truncated form thereof may be glycosylated, which, preferably, may be glycosylated at position(s) 53, 90, 103, 322, 432, 546 and/or 690 in the N-terminal of the human ACE2.

Preferably, the soluble ACE2 or truncated form thereof may have an amino acid sequence as shown by SEQ ID NO: 1.

Preferably, the soluble ACE2 or truncated form thereof may have an amino acid sequence as shown by SEQ ID NO: 2.

The soluble ACE2 or truncated form thereof can effectively neutralize a virus that uses the ACE2 as a host-binding receptor. The virus may comprise SARS-CoV, HCoV-NL63 or SARS-CoV2.

In some embodiments, the antibody may be an IgG antibody. The antibody may be a human IgG, such as IgG1, IgG2, IgG3 or IgG4, preferably IgG1. The antibody Fc domain may refer to an antibody Fc-domain containing two heavy chain Fc domains of the antibody. Preferably, each of the heavy chain Fc domains may have a hinge region at its N-terminal. Preferably, each of the heavy chain Fc domains may comprise a CH3 domain derived from IgG1, IgG2, IgG3 or IgG4. Preferably, each of the heavy chain Fc domains may comprise CH2 and CH3 domains derived from IgG1, IgG2, IgG3 or IgG4. The Fc domains can promote the dimerization of two ACE2 domains.

In some embodiments, the heavy chain Fc domain may comprise a heavy chain Fc domain having an L309C mutation at position 309.

The soluble ACE2 or truncated form thereof may be linked to the C-terminal end of the heavy chain Fc domain, or to the N-terminal end of the heavy chain Fc domain.

Preferably, in each polypeptide monomer unit, one ACE2 truncated form, one heavy chain Fc domain along with the tail may have an amino acid sequence as shown by SEQ ID NO: 7.

Preferably, in each polypeptide monomer unit, one ACE2 truncated form, one heavy chain Fc domain along with the tail may have an amino acid sequence as shown by SEQ ID NO: 8.

Preferably, in each polypeptide monomer unit, one ACE2 truncated form, one heavy chain Fc domain along with the tail may have an amino acid sequence as shown by SEQ ID NO: 18.

In some embodiments, the fusion protein multimer ACE2-hFc(n) may comprise ACE2-hFc5, ACE2-NN-hFc5, or ACE2-NN-hFc5 L309C, wherein:

ACE2-hFc5 refers to a tetramer assembled from 5 polypeptide monomer units via 10 tails located at the C-terminals of 5 Fc-domains, each of the polypeptide monomer units comprises a dimer composed of two ACE2 truncated forms and two heavy chain Fc domains, wherein one ACE2 truncated form, one heavy chain Fc domain along with the tail comprise an amino acid sequence as shown by SEQ ID NO: 7;

ACE2-NN-hFc5 refers to a tetramer assembled from 5 polypeptide monomer units via 10 tails located at the C-terminals of 5 Fc-domains, each of the polypeptide monomer units comprises a dimer composed of two ACE2 truncated forms and two heavy chain Fc domains, wherein one ACE2 truncated form, one heavy chain Fc domain along with the tail comprise an amino acid sequence as shown by SEQ ID NO: 8;

ACE2-NN-hFc5-L309C refers to a tetramer assembled from 5 polypeptide monomer units via 10 tails at the C-terminals of 5 Fc-domains, each of the polypeptide monomer units comprises a dimer composed of two ACE2 truncated forms and two heavy chain Fc domains, wherein one ACE2 truncated form, one heavy chain Fc domain along with the tail comprise an amino acid sequence as shown by SEQ ID NO: 18, and wherein the heavy chain Fc domain comprises an L309C mutation at position 309.

In some embodiments, the fusion protein multimer ACE2-hFc(n) may comprise ACE2-hFc6, ACE2-NN-hFc6, or ACE2-NN-hFc6 L309C, wherein:

ACE2-hFc6 refers to a hexamer assembled from 6 polypeptide monomer units via 12 tails at the C-terminals of 6 Fc-domains, each of the polypeptide monomer units comprises a dimer composed of two ACE2 truncated forms and two heavy chain Fc domains, wherein one ACE2 truncated form, one heavy chain Fc domain along with the tail comprise an amino acid sequence as shown by SEQ ID NO: 7;

ACE2-NN-hFc6 refers to a hexamer assembled from 6 polypeptide monomer units via 12 tails at the C-terminals of 6 Fc-domains, each of the polypeptide monomer units comprises a dimer composed of two ACE2 truncated forms and two heavy chain Fc domains, wherein one ACE2 truncated form, one heavy chain Fc domain along with the tail comprise an amino acid sequence as shown by SEQ ID NO: 8;

ACE2-NN-hFc6-L309C refers to a hexamer assembled from 6 polypeptide monomer units via 12 tails at the C-terminals of 6 Fc-domains, each of the polypeptide monomer units comprises a dimer composed of two ACE2 truncated forms and two heavy chain Fc domains, wherein one ACE2 truncated form, one heavy chain Fc domain along with the tail comprise an amino acid sequence as shown by SEQ ID NO: 18.

In some embodiments, the fusion protein multimer may be one or more selected from the following fusion protein multimers:

ACE2-hFc4, which is a tetramer assembled from 4 polypeptide monomer units via the tails at the C-terminals of the Fc-domains, each of the polypeptide monomer units comprises a dimer composed of two ACE2 truncated forms and two heavy chain Fc domains, wherein one ACE2 truncated form, one heavy chain Fc domain along with the tail comprise an amino acid sequence as shown by SEQ ID NO: 7;

ACE2-NN-hFc4, which is a pentamer assembled from 4 polypeptide monomer units the tails at the C-terminals of the Fc-domains, each of the polypeptide monomer units comprises a dimer composed of two ACE2 truncated forms and two heavy chain Fc domains, wherein one ACE2 truncated form, one heavy chain Fc domain along with the tail comprise an amino acid sequence as shown by SEQ ID NO: 8;

ACE2-NN-hFc4-L309C, which is a tetramer assembled from 4 polypeptide monomer units via the tails at the C-terminals of the Fc-domains, each of the polypeptide monomer units comprises a dimer composed of two ACE2 truncated forms and two heavy chain Fc domains, wherein one ACE2 truncated form, one heavy chain Fc domain along with the tail comprise an amino acid sequence as shown by SEQ ID NO: 18, and wherein the heavy chain Fc domain has an L309C mutation at position 309;

ACE2-hFc5, which is a pentamer assembled from 5 polypeptide monomer units via the tails at the C-terminals of the Fc-domains, each of the polypeptide monomer units comprises a dimer composed of two ACE2 truncated forms and two heavy chain Fc domains, wherein one ACE2 truncated form, one heavy chain Fc domain along with the tail comprise an amino acid sequence as shown by SEQ ID NO: 7;

ACE2-NN-hFc5, which is a pentamer assembled from 5 polypeptide monomer units via the tails at the C-terminals of the Fc-domains, each of the polypeptide monomer units comprises a dimer composed of two ACE2 truncated forms and two heavy chain Fc domains, wherein one ACE2 truncated form, one heavy chain Fc domain along with the tail comprise an amino acid sequence as shown by SEQ ID NO: 8;

ACE2-NN-hFc5-L309C, which is a pentamer assembled from 5 polypeptide monomer units via the tails at the C-terminals of the Fc-domains, each of the polypeptide monomer units comprises a dimer composed of two ACE2 truncated forms and two heavy chain Fc domains, wherein one ACE2 truncated form, one heavy chain Fc domain along with the tail comprise an amino acid sequence as shown by SEQ ID NO: 18, and wherein the heavy chain Fc domain has an L309C mutation at position 309;

ACE2-hFc6, which is a hexamer assembled from 6 poly-peptide monomer units via the tails at the C-terminals of the Fc-domains, each of the polypeptide monomer units comprises a dimer composed of two ACESARS-CoV22 truncated forms and two heavy chain Fc domains, wherein one ACE2 truncated form, one heavy chain Fc domain along with the tail comprise an amino acid sequence as shown by SEQ ID NO: 7;

ACE2-NN-hFc6, which is a hexamer assembled from 6 polypeptide monomer units via the tails at the C-ter-minals of the Fc-domains, each of the polypeptide monomer units comprises a dimer composed of two ACE2 truncated forms and two heavy chain Fc domains, wherein one ACE2 truncated form, one heavy chain Fc domain along with the tail comprise an amino acid sequence as shown by SEQ ID NO: 8;

ACE2-NN-hFc6-L309C, which is a hexamer assembled from 6 polypeptide monomer units via the tails at the C-terminals of the Fc-domains, each of the polypeptide monomer units comprises a dimer composed of two ACE2 truncated forms and two heavy chain Fc domains, wherein one ACE2 truncated form, one heavy chain Fc domain along with the tail comprise an amino acid sequence as shown by SEQ ID NO: 18.

The fusion protein multimers can greatly enhance the affinity with the viral S protein, and, meanwhile, will also enhance the effector function of the Fc molecule.

In a fourth aspect, the present disclosure provides an expression vector comprising a gene encoding the soluble ACE2 or truncated form thereof of the first aspect, the ACE2-Fc fusion protein of the second aspect, or the Fc fusion protein multimer ACE2-hFc(n) of the soluble ACE2 or a truncated form thereof of the third aspect.

In a fifth aspect, the present disclosure provides a mam-malian cell strain comprising a gene encoding the soluble ACE2 of the first aspect, the ACE2-Fc fusion protein of the second aspect, or the Fc fusion protein multimer ACE2-hFc (n) of the soluble ACE2 or a truncated form thereof of the third aspect. The cell strain may include, but be not limited to, a CHO cell strain, a 293 cell strain and a Vero cell strain and a cell strain derived therefrom, e.g., Vero E6 cells or HEK293T cells.

In a sixth aspect, the present disclosure provides a method for preparing the soluble ACE2 of the first aspect, the ACE2-Fc fusion protein of the second aspect, or the Fc fusion protein multimer ACE2-hFc(n) of the soluble ACE2 or a truncated form thereof of the third aspect, which comprises the following steps:

(1) transfecting a mammalian cell strain with the expres-sion vector of the fourth aspect to obtain a mammalian cell strain expressing the soluble ACE2 of the first aspect, the ACE2-Fc fusion protein of the second aspect, or the Fc fusion protein multimer ACE2-hFc(n) of the soluble ACE2 or a truncated form thereof of the third aspect;

(2) culturing the mammalian cell strain obtained in step (1) under a culture condition to produce the soluble ACE2 of the first aspect, the ACE2-Fc fusion protein of the second aspect, or the Fc fusion protein multimer ACE2-hFc(n) of the soluble ACE2 or a truncated form thereof of the third aspect so as to produce a recombinant protein; and (3) purifying the recombinant protein produced in step (2).

In a seventh aspect, the present disclosure further provides a pharmaceutical composition comprising: the soluble ACE2 of the first aspect, the ACE2-Fc fusion protein of the second aspect, or the Fc fusion protein multimer ACE2-hFc(n) of the soluble ACE2 or a truncated form thereof of the third aspect; and a pharmaceutically accept-able carrier.

In an eighth aspect, the present disclosure provides use of the soluble ACE2 of the first aspect, the ACE2-Fc fusion protein of the second aspect, or the Fc fusion protein multimer ACE2-hFc(n) of the soluble ACE2 or a truncated form thereof of the third aspect in the preparation of a medicament for treating or preventing an ACE2-related disease.

The disease may be a disease selected from any one caused by an infection of a virus employing ACE2 as a receptor. The virus may comprise a coronavirus, e.g., SARS-CoV, HCoV-NL63, or SARS-CoV2. The disease may be selected from pneumonia, severe acute respiratory infection, renal failure, heart failure, adult respiratory distress syn-drome (ARDS), liver injury, intestinal disease, or severe acute respiratory syndrome.

The soluble ACE2 of the first aspect, the ACE2-Fc fusion protein of the second aspect, or the Fc fusion protein multimer ACE2-hFc(n) of the soluble ACE2 or a truncated form thereof of the third aspect in the present disclosure can be used for administration in emergency situations, thereby avoiding high morbidity and lethality caused by the infec-tion of viruses employing ACE2 as a receptor, especially coronavirus infections.

The soluble ACE2 of the first aspect, the ACE2-Fc fusion protein of the second aspect, or the Fc fusion protein multimer ACE2-hFc(n) of the soluble ACE2 or a truncated form thereof of the third aspect in the present disclosure can also be used for passive immunization of a medical worker and a person at risk of exposing to a virus, especially a coronavirus, employing ACE2 as a receptor.

The syncytia refer to multinucleated giant cells which are eventually formed by fusion of cells after the infection of viruses of host cells. SARS-CoV2-infected severe patients may have diffuse damages to alveolar epithelium, resulting in the formation of fused multinucleated cells (syncytia). The syncytia are caused by the binding of viral S protein to ACE2, which is an important reason for the cytopathic effect. Meanwhile, cytokine storm can also cause alveolar damages. The multimeric Fc fusion protein (ACE2-NN-hFcn) of the soluble ACE2 can effectively prevent the binding of viral S protein to ACE2, thereby avoiding the formation of the fused multinucleated cells (syncytia) as well as the subsequent cytopathic effect.

Preferably, the medicament can be administered by inha-lation, intranasal or airway instillation, ocular and middle ear injection, ear drops, topical, transdermal, parenteral, subcutaneous and intravenous injection, intradermal injec-tion, intramuscular injection, intrapleural instillation, intra-peritoneal injection, intralesional administration, application to mucosa, or transplantation of a sustained-release carrier. Preferably, the medicament is administered by nebulizer inhalation.

In a ninth aspect, the present disclosure provides a method for screening a medicament against an infection of a virus, especially a coronavirus, employing ACE2 as a receptor which comprises: screening the medicament using the soluble ACE2 of the first aspect, the ACE2-Fc fusion protein of the second aspect, the Fc fusion protein multimer ACE2- hFc(n) of the soluble ACE2 or a truncated form thereof of the third aspect, the vector of the fourth aspect, or the mammalian cell strain of the fifth aspect.

In a tenth aspect, the present disclosure provides a method for screening a medicament against an infection of a virus, especially a coronavirus, employing ACE2 as a receptor, which comprises: using a Furin protease or a Furin cleavage site in S protein of the coronavirus as a target for drug screening.

The medicament may be an inhibitor for the Furin protease.

The medicament may be capable of blocking the formation of syncytia via the S protein containing the Furin cleavage site during the infection of the virus, especially a coronavirus, employing ACE2 as a receptor.

In an eleventh aspect, the present disclosure provides use of a reagent targeting a Furin protease or a Furin cleavage site in S protein of the coronavirus in the preparation of a medicament for an infection of a virus, especially a coronavirus, employing ACE2 as a receptor.

Especially, the present disclosure relates to use of a reagent blocking formation of syncytia via S protein containing a Furin cleavage site during the infection of the virus, especially a coronavirus, employing ACE2 as a receptor, in the preparation of a medicament for the infection of the virus employing ACE2 as a receptor, especially the coronavirus.

Preferably, the reagent may be an inhibitor of Furin protease.

The coronavirus may be SARS-CoV2.

In a twelfth aspect, the present disclosure provides a mutant S protein, which is a truncated form, and/or a form in which the Furin cleavage site is mutated.

The truncated form may comprise S protein only containing an ectodomain (S1+S2), i.e., deleting the transmembrane and intracellular regions.

The Furin cleavage site may be mutated by deletion, substitution or addition of one or more amino acids, so that the Furin cleavage site is no longer active as a Furin cleavage site.

Preferably, the form, in which the Furin cleavage site is mutated, may comprise a mutation from RRAR to SRAS at the Furin cleavage site of S protein.

Preferably, in addition to the mutation at the Furin cleavage site, the mutated S protein may contain only an ectodomain (S1+S2), i.e., deleting transmembrane and intracellular regions.

The mutated S protein may have an amino acid sequence as shown by SEQ ID NO: 10, SEQ ID NO: 11 or SEQ ID NO: 12.

SEQ ID NO: 10 is an amino acid sequence in which the Furin cleavage site of S protein is mutated from RRAR to SRAS. SEQ ID NO: 11 is an amino acid sequence of S protein in a truncated form, with the transmembrane and intracellular regions deleted. SEQ ID NO: 12 is an amino acid sequence in which the Furin cleavage site is mutated from RRAR to SRAS, and the S protein is in a truncated form, with deleting the transmembrane and intracellular regions.

In a thirteen aspect, the present disclosure further relates to use of the mutant S protein of the twelfth aspect in the preparation of a medicament for treating or preventing an ACE2-related disease.

The disease is a disease caused by an infection of a virus employing ACE2 as a receptor, and, preferably, the virus may be a coronavirus, preferably SARS-CoV, HCoV-NL63, or SARS-CoV2.

The disease may be selected from pneumonia, severe acute respiratory infection, renal failure, heart failure, adult respiratory distress syndrome (ARDS), liver injury, intestinal disease, or severe acute respiratory syndrome.

The medicament can be used for passive immunization of a medical worker and a person at risk of exposing to a virus employing ACE2 as a receptor, especially coronaviruses.

In a fourteenth aspect, the present disclosure provides a recombinant vaccine for the prevention of an infection of SARS-CoV2, which comprises the S protein of the twelfth aspect.

The Furin cleavage site of SARS-CoV2 S protein and Furin protease can be used as targets for screening drugs for treating a disease caused by the infection of virus employing ACE2 as a receptor.

The present disclosure confirms that the Furin cleavage site in SARS-CoV2 S protein is necessary for the formation of syncytia. Specifically, the SARS-CoV 2 spike (S) protein has an RRAR motif near residues 681-685 (near the S1/S2 junction), which can be cleaved by a protease such as Furin. It shows, by sequence alignment, that this motif is present in all of the known SARS-CoV2 strains, but not in the RaTG13 bat strain, which is the closest to SARS-CoV2. With the alignment of the bat virus sequences in the database, there is only a similar sequence (RRAT) in the bat SARS-HKU5 virus. We found that 293T cell transfected with the plasmids expressing wild-type SARS-CoV2 S protein or SARS-CoV2 S protein with mutated Furin protease cleavage site could bind to ACE2-IgG1 Fc. While the control cells transfected with an empty vector did not bind to ACE2-IgG1 Fc. The wild-type SARS-CoV2 S protein and the SARS-CoV2 S protein with mutated Furin protease cleavage site could be expressed normally on the surfaces of 293T cells. Further, the SARS-CoV2 S protein with mutated Furin protease cleavage site (RRAR mutated to SRAS) could bind stronger to ACE2-IgG1 Fc.

In a syncytia formation experiment, no cell fusion was observed between the control cells transfected with the empty vector and the cells expressing a full-length human ACE2 (human natural ACE2), and thus no formation of multinucleated syncytia was observed. In contrast, it was observed that a large number of multinucleated syncytia were formed after co-culturing the cells expressing wild-type SARS-CoV2 S protein with the cells expressing the full-length human ACE2 for 3 h. The formed syncytia died after 24 h of continuous culture. When the Furin site RRAR in the SARS-CoV2 S protein was mutated to SRAS, the cell fusion was completely inhibited and no multinucleate syncytia were observed, which showed that the mutated S protein lost the ability of mediating the cell fusion, and that the Furin site in the S protein was crucial for the cell infection of SARS-CoV2.

Therefore, the drugs targeting the S protein Furin site (PRRAR) and Furin protease have the ability of inhibiting SARS-CoV2 infection. Moreover, the antiviral drugs for treating the SARS-CoV2 infection can be developed by inhibiting the fusion of the coronavirus in the process of entering cells.

Further, when the Furin site RRAR in the SARS-CoV2 S protein was mutated to SRAS, the cell fusion was completely inhibited, and no multinucleate syncytia were observed. It shows that the mutated S protein lost the ability of mediating the cell fusion. Therefore, the SARS-CoV2 S with mutated Furin protease cleavage site in the present disclosure, especially the SARS-CoV2 S having mutation(s) at the Furin protease cleavage site of deleting the transmembrane and intracellular regions, can be used as a recombinant protein drug to competitively block the binding of the virus with wild-type S protein to a cellular receptor, thereby blocking the infection. Further, the SARS-CoV2 S protein with mutated Furin protease cleavage site can also be used as a candidate molecule for a recombinant vaccine, and is more stable than the wild-type S protein.

The SARS-CoV2, a β-coronavirus, has an envelope. SARS-CoV2 virions are round or oval particles, with polymorphism, in a diameter of 60-140 nm. The spike glycoproteins (S protein) on the envelope surface are main antigenic proteins of the coronavirus, and are very important for the infection and spread of the viruses. The S protein has two subunits, wherein the subunit S1 binds to a cell surface receptor and the subunit S2 contains basic motifs required for the membrane fusion process.

The amino acid sequence of the Spike (S) protein of SARS-CoV2 has about 76% homology with the S protein of SARS-CoV. That is, the homology is relatively low. Therefore, most of the neutralizing antibodies of the SARS-CoV virus cannot neutralize SARS-CoV2. However, the SARS-CoV2 shares the same host cell receptor as SARS-CoV, i.e., angiotensin-converting enzyme 2 (ACE2). Like SARS-CoV, the infection of SARS-CoV2 has to employ ACE2 as a receptor for entry target cells. In other words, although there are multiple differences between the amino acid sequence of the SARS-CoV2 S protein and that of the SARS-CoV S protein, both of them still use ACE2 as the receptor for entry host cells. This indicates that the ACE2 protein has high structure compatibility at its surface with the S protein of such coronaviruses. Thus, ACE2, as a host protein molecule, can be easily utilized by the spike proteins with many differences in the sequences. Thus, ACE2 would still be an entry point for such viruses to infect humans in the future. The soluble ACE2 and the soluble ACE2 (NN) with a mutated enzyme active center obtained by the present disclosure can block the binding of the virus which employs ACE2 as a host receptor, to the ACE2 receptor, thereby inhibiting the virus invasion. Both of the soluble ACE2 and ACE2 (NN) have great significance for the prevention and control of the possible future epidemic.

Moreover, with the epidemic of SARS-CoV2 in the population, many variants are generating under selection pressures such as further adaptation to human hosts and human immunity. These variants may have changes in the virulence and antigenic sites. Similar changes have been observed and recorded several times for SARS-CoV. The latest sequencing data of SARS-CoV2 shows that the receptor binding domain (RBD) of the S protein is still in the process of mutation in the sequence. The advantage of the soluble ACE2 and the soluble ACE2 (NN) with a mutated enzyme active center obtained by the present disclosure also lies in that SARS-CoV2 can be strongly neutralized, as long as the virus uses ACE2 as a entry receptor, even the virus proteins, especially the S protein, are mutated. For the prevention and treatment of a virus that is undergoing evolution, the soluble ACE2 receptor of the present disclosure, unlike the monoclonal neutralizing antibodies of S protein, can be used as a therapeutic drug having a broad-spectrum neutralizing ability, and be not restricted by virus mutations, without the requirement of antibody screening. Thus, it is very applicable for the urgent needs for the prevention of the virus epidemic at present and in the future. The experimental results show that the pentameric ACE2-NN-hFc5 of the present disclosure has a strong neutralizing activity against the infections of all the existing main variant pseudoviruses.

In addition, unlike antibody drugs, the receptor is a human body's own protein, and thus does not need tissue cross-reactivity assay. The receptor fusion proteins are used as an emergency drug for acute infectious diseases, have a long half-life, and are usually administered 1-2 times for the treatment. Therefore, it can also avoid anti-drug antibody and long-term toxicity researches, and shorten the development cycle.

The ACE2-Fc fusion protein and the multimers of the soluble ACE2-Fc fusion protein (ACE2-NN-hFcn) of the present disclosure can be therapeutic drugs which are specific for new epidemic in a quickest way. The ACE2-Fc fusion proteins and the multimers thereof of the present disclosure mainly comprise the following advantages:

(1) avoiding virus escape as neutralizing antibodies;

(2) preventing the formation of SARS-CoV2 and SARS-CoV syncytia;

(3) being capable of recruiting, through relevant receptors, complements, dendritic cells, macrophages and natural killer cells against virions or infected cells, due to the preserved effector function of the Fc domain;

(4) prolonging the circulating half-life of the soluble ACE2 molecules;

(5) the ACE2-Fc, ACE2(NN)-Fc or ACE2-NN-hFcn of the present disclosure being applicable for compassionate use in emergencies (the formal clinical trials can be performed subsequently), because a recombinant human ACE2 (rhACE2) had been evaluated in a phase II clinical trial and shows good tolerance and safety, although no significant improvement was observed in the clinical symptoms of the subjects;

(6) the ACE2-Fc, ACE2(NN)-Fc or ACE2-NN-hFcn of the present disclosure being capable of widely using in the coming months or years to help infected patients before the vaccination;

(7) the soluble ACE2 obtained by the present disclosure being applicable for blocking virus infection which is independent of the natural enzyme activity of ACE2 and does not affect the activity of natural ACE2 in patients; in which the soluble ACE2 (NN) with a mutated enzyme active center even avoids potential side effect caused by the ACE2 enzymatic activity in the body, thereby maximizing the use safety in the human body;

(8) as compared with anti-S protein antibodies, another advantage of the soluble ACE2 lying in that, as long as the virus uses ACE2 as an entry receptor, the virus mutation(s) would not affect the effectiveness of the soluble ACE2, including enhanced affinity with the receptor caused by the virus mutation(s).

The ACE2 is a metalloprotease that catalyzes the degradation of angiotensin I to angiotensin nonapeptide (1-9), or angiotensin II to angiotensin heptapeptide (1-7). It is thought to be involved in the regulation of cardiovascular functions and may play a protective role in acute lung injuries, e.g., for vasodilation, anti-proliferation and anti-oxidative stress. The ACE2 is expressed in the vasculature as well as in most organs, but mainly in lung, heart, liver, kidney and testis. Therefore, the drug candidates that inhibit the ACE2 enzymatic activity are not ideal drugs.

The human natural ACE2 (called a membrane-type ACE2) has a full length of 805 amino acids, in which the region of positions 1-740 are the extracellular domain, and the remaining 65 amino acids serve as short transmembrane and intracellular regions. The enzymatic activity of the ACE2 is performed by the extracellular domain. The soluble ACE2 or a truncated form thereof in the present disclosure does not have the transmembrane domain.

BRIEF DESCRIPTION OF THE DRAWINGS

FIG. 4 shows an amino acid sequence (SEQ ID NO: 9) and Furin site of the Spike protein (S protein) of the SARS-CoV2.

FIG. 5 shows an amino acid sequence (SEQ ID NO: 10) of the SARS-CoV2 S protein having mutations at the Furin cleavage site.

FIG. 6 shows the expression of the SARS-CoV2 S protein at the cell surface and the cell surface analysis result of the SARS-CoV2 S protein having mutations at the Furin site.

FIG. 7 shows that no cell fusion occurs between control cells transfected with the empty vector (marked in red) and cells expressing the human ACE2 (marked in green), without the formation of multinucleated syncytia; in the group of wild-type SARS-CoV2 S protein-expressing cells (marked in red), it is observed that a large number of multinucleated syncytia is formed after co-culture with the cells expressing ACE2 (marked in green) for 3 h, and the formed syncytia died after 24 h of continuous culture; and the S protein having mutations at the furin site does not produce syncytia after being mixed with the cells expressing ACE.

FIG. 8 shows a wild-type Ectdomain (1-1208aa) (SEQ ID NO: 11) of the SARS-CoV2 S protein, and an Ectdomain (1-1208aa) (SEQ ID NO: 12) of the SARS-CoV2 S protein having mutations at the Furin cleavage site.

FIG. 14 shows the evaluation results of the in vitro neutralization activity of the ACE2-hFc5 molecule against the SARS-CoV2 pseudovirus infection before and after nebulization.

FIG. 15 shows RT-qPCR quantitative analysis of the contents of SARS-CoV2 gRNA and sgRNA in hamster lungs.

DETAILED DESCRIPTION OF THE EMBODIMENTS

The following embodiments are intended to illustrate the present disclosure, but not to limit the scope of the present disclosure. Modifications or substitutions made to the methods, steps or conditions of the present disclosure, without departing from the spirit and essence of the present disclosure, all fall within the scope of the present disclosure.

Figure 16:
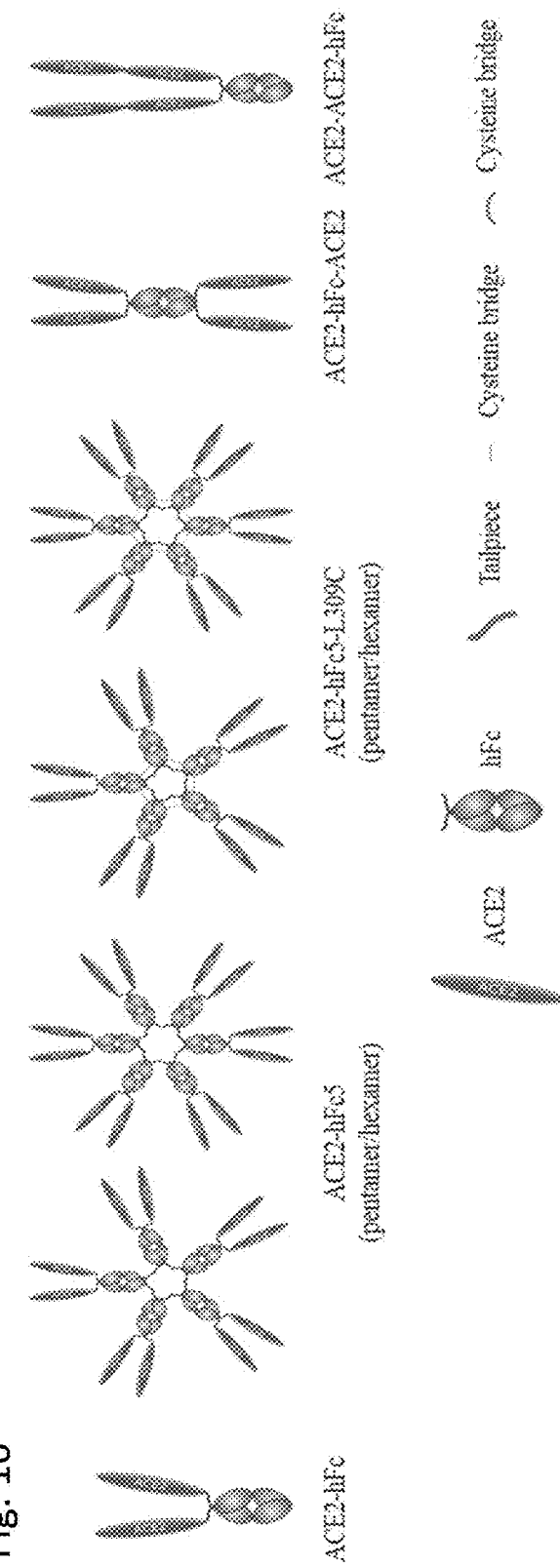
FIG. 16 schematically shows the molecular structures of different forms of ACE2-IgG1 fusion proteins.

Unless otherwise specified, the chemical reagents used in the embodiments are all conventional commercially available reagents, and the technical means adopted in the embodiments are conventional means well known to those skilled in the art. The Fc throughout the embodiments and figures is derived from IgG1. The ACE2-hFc throughout the embodiments and figures is ACE2-NN-hFc in which one ACE2 truncated form and one heavy chain Fc domain have an amino acid sequence as shown by SEQ ID NO: 4. Unless otherwise specified, different forms of ACE2-hFc refer to all ACE2-hFc and ACE2-hFc multimers and mutants. The ACE2-hFc-ACE2s throughout the embodiments and figures are tetrameric ACE2(NN)-hFc-ACE2(NN), in which one ACE2 truncated form is linked to one heavy chain Fc domain and then linked to one ACE2 (ACE2-Fc-ACE2), resulting in an amino acid sequence as shown by SEQ ID NO: 13. The ACE2-ACE2-hFcs throughout the embodiments and figures are tetrameric ACE2(NN)-ACE2(NN)-hFc, in which one heavy chain Fc domain (ACE2-ACE2-Fc) are linked two ACE2s or truncated forms thereof that are linked in tandem, resulting in an amino acid sequence as shown by SEQ ID NO: 14. The ACE2-hFc5s throughout the embodiments and figures refers to ACE2(NN)-hFc(5), which is a tetramer assembled from 5 polypeptide monomer units via 10 tails located at the C-terminals of 5 Fc-domains, each of the polypeptide monomer unit comprises a dimer composed of two ACE2 truncated forms and two heavy chain Fc domains, wherein one ACE2 truncated form, one heavy chain Fc domain along with the tail comprise an amino acid sequence as shown by SEQ ID NO: 8. The ACE2-hFc5-L309C throughout the embodiments and figures refers to ACE2(NN)-hFc(5)-L309C, which is a tetramer assembled from 5 polypeptide monomer units via 10 tails located at the C-terminals of 5 Fc-domains, each of the polypeptide monomer unit comprises a dimer composed of two ACE2 truncated forms and two heavy chain Fc domains, wherein one ACE2 truncated form, one heavy chain Fc domain along with the tail comprise an amino acid sequence as shown by SEQ ID NO: 18, and the heavy chain Fc domain comprises an L309C mutation at position 309. Refer to FIG. 16.

Example 1: Construction of ACE2-hFc Fusion Protein Expression Plasmid, SARS-CoV2 S Protein Expression Plasmid and Furin Site Mutated SARS-CoV2 S Protein Expression Plasmid By using primers as shown in Table 1, DNA sequences encoding CD33 signal peptide, ACE2 metalloprotease domain extracellular region (containing H374N and H378N enzyme inactivation mutations) and hIgG1 Fc were obtained via Overlap PCR. The specific cloning steps comprise the following: regarding the construction of the ACE2-hFc expression plasmid, using pcDNA3.0-ACE2-NEMGE as a template, and using primers 2-FrontIn and 4-MidR to obtain, via PCR, DNA fragments encoding ACE2 extracellular region (19-615aa) containing enzymatic activity inactivation mutations H374N and H378N; using pCHOGS-HH009 as a template, and using primers 3-MidF and 5-IgG1Cterm to obtain, via PCR, DNA fragments encoding the hIgG1 Fc; then using the obtained products as templates, and using primers 6-FrontOutXhoI and 5-IgG1Cterm to synthesize, via Overlap PCR, a full-length DNA encoding CD33 signal peptide-ACE2 extracellular region-hFc, which then was inserted into human pCHOGS expression vector between XhoI and Pad cleavage sites to obtain pCHOGS-ACE2-NN-hIgG1 expression plasmid.

TABLE 1

Construction Primers of ACE2 IgG1 Fusion Protein Expression Plasmid

| Primer ID | Sequence(5'-3') |
| --- | --- |
| 6-FrontOutXhoI | aagCTCGAGgccaccATGCCGCTGCTGCTACTGCTGCCCCTGCTGTGGGC |
| 2-FrontIn | CTGCCCCTGCTGTGGGCAGGGGCGCTCGCTaccattgaggaacaggccaag |
| 3-MidF | gactggagtccatatgcagacgagcccaaatcttCtgacaaaactcacacatgcc |
| 4-MidR | ggcatgtgtgagttttgtcaGaagatttgggctcgtctgcatatggactccagtc |
| 5-IgG1Cterm | cccTTAATTAAtcatttacccg |
| 7-Oligomer (pentamer)In | CATCACCAGAGACACGTTGTAGAGGGTGGGCTTGCCGGTagacagggagaggctcttc |
| 8-Oligomer (pentamer)Out | cccTTAATTAAtcaGTAGCATGTGCCGGCGGTGTCGCTCATCACCAGAGACACG TTGTA |

Regarding the construction of the coronavirus spike protein expression plasmid pCAGGS-SARS-CoV2 S-C9, pCMV3-2019-nCoV-Spike(S1+S2)-long (Sino Biological, Cat #: VG40589-UT) was used as a template, and SB-S-NheI: CGTGCTAGCcGTGAACCT GACCACCAGGACC-CAA and SB-S-C9-XhoI: CGCCTCGAGCTAGGCGGGCGC-CACCTGGCTGGTCTCGGTGGTGTAGTGCAGTTT-CAC TCC were used as primers, to obtain DNA fragments encoding the SARS-CoV2 spike protein, which were inserted into a human pCAGGS vector between NheI and XhoI cleavage sites to obtain the SARS-CoV2 S protein expression plasmid. In the plasmid, the N-terminal signal peptide was a CD4 signal peptide, and a C9 tag was comprised at the C-terminal.

On the basis of this plasmid, primers SB-S-NheI, SB-S-C9-XhoI, and SB-Drs-f: CAGCC-CAagcAGGGCAagcTCTGTGCAAGCCAG and SB-Drs-r: CTGGCTTGCCACAGAgctTGCCCTgctTGGGCTG were used, the Furin protease cleavage site PRRAR in the S protein was mutated to PSRAS via Overlap PCR, so as to obtain SARS-CoV2 S protein expression plasmid which comprised mutated Furin site.

Example 2: Construction of ACE2-hFc-ACE2 Fusion Protein, ACE2-ACE2-hFc Fusion Protein, ACE2-hFc5 Fusion Protein and ACE2-hFc5-L309C Fusion Protein Expression Plasmids The construction of the ACE2-hFc-ACE2 fusion protein, ACE2-ACE2-hFc fusion protein, ACE2-hFc5 fusion protein, and ACE2-hFc5-L309C fusion protein expression plasmids were similar to that of the ACE2-hFc fusion protein expression plasmid, and were constructed using the method similar to Example 1.

Example 3: Expression, Purification and SEC-HPLC Analysis of ACE2-hFc Fusion Protein and ACE2-hFc5 Fusion Protein The expression plasmid expressing the ACE2-hFc fusion protein obtained in Example 1 and the expression plasmid expressing the ACE2-hFc5 fusion protein obtained in Example 2 were respectively transfected into 293F cells by PEI. The culture supernatants were collected 5 days after transfection and purified via a Protein A column in one step, to obtain the purified ACE2-hFc fusion protein and ACE2-hFc5 fusion protein, respectively. After protein quantification by Nano drop2000, SEC-HPLC purity analysis was performed (FIGS. 1A and 1C). As can be seen from FIG. 1A, the purity analysis of the obtained ACE2-hFc fusion protein shows only one peak, and the main peak is 99.34%. As can be seen from FIG. 1C, the purity analysis of the obtained ACE2-hFc5 fusion protein shows only one peak, and the main peak is 66.94%.

Example 4: Expression, Purification and SEC-HPLC Analysis of ACE2-hFc-ACE2 Fusion Protein, ACE2-ACE2-hFc Fusion Protein and ACE2-hFc5-L309C Fusion Protein The expression plasmids expressing the ACE2-hFc-ACE2 fusion protein, the ACE2-ACE2-hFc fusion protein and the ACE2-hFc5-L309C fusion protein obtained in Example 2 were respectively transfected into 293F cells by PEI. The culture supernatants were collected 5 days after transfection, and purified via a Protein A and a molecular sieve in two steps, to obtain the purified ACE2-ACE2-hFc fusion protein, ACE2-hFc-ACE2 fusion protein and ACE2-hFc5-L309C fusion protein, respectively. After protein quantification by Nano drop2000, SEC-HPLC purity analysis was performed for each of them (FIGS. 1B, 1D and 1E). As can be seen from FIG. 1B, the main peak of the ACE2-ACE2-hFc fusion protein is 98.96%. As can be seen from FIG. 1D, the main peak of the ACE2-hFc-ACE2 fusion protein is 97.99%. As can be seen from FIG. 1E, the main peak of the ACE2-hFc5-L309C fusion protein is 97.99%.

Example 5: Expression, Purification and SEC-HPLC Analysis of ACE2-hFc5 Fusion Protein The expression plasmid expressing the ACE2-hFc5 fusion protein obtained in Example 2 was transfected into 293F cells by PEI. The culture supernatant was collected 5 days after transfection and purified in multiple steps, to obtain the purified ACE2-hFc5 fusion protein. After protein quantification by Nano drop2000, SEC-HPLC purity analysis was performed (FIG. 1F). As can be seen from FIG. 1F, the main peak of the ACE2-hFc5 fusion protein is 99.2%.

Example 6: In Vitro Intercellular Membrane Fusion Inhibition Experiment

6.1 Method

Experiment of the ACE2 Fusion Proteins Inhibiting the Formation of Coronavirus (SARS-CoV2) Syncytia The pCAGGS control vector, and the plasmids expressing the SARS-CoV2 S-protein and the SARS S-protein were co-transfected, respectively, with pEGFP-N1 into 293T cells. The plasmid expressing hACE2-C9 (preserved in our laboratory) and the pmCherry-C1 vector were co-transfected into 293T cells by PEI. The cells were digested 24 h after transfection, washed once with a DMEM complete medium (10% FBS, 1×PS) and counted. Then, 10 μg/mL of the control protein and the ACE2-hFc5 fusion proteins were co-incubated, respectively, with 2.5E5/well pCAGGS control vector-transfected cells, SARS-CoV2-S and SARS-S transfected cells at 37° C. for 30 min. hACE2-C9 transfected cells were then added at 2.5E5/well. After co-culture in a 5% CO$_2$ cell incubator at 37° C. for 3 h, the inhibition activities of the ACE2-hFc5 fusion proteins for the formation of coronavirus (SARS-CoV2) syncytia were observed under a fluorescence microscope. The experimental results were photographed and recorded.

Figure 2:
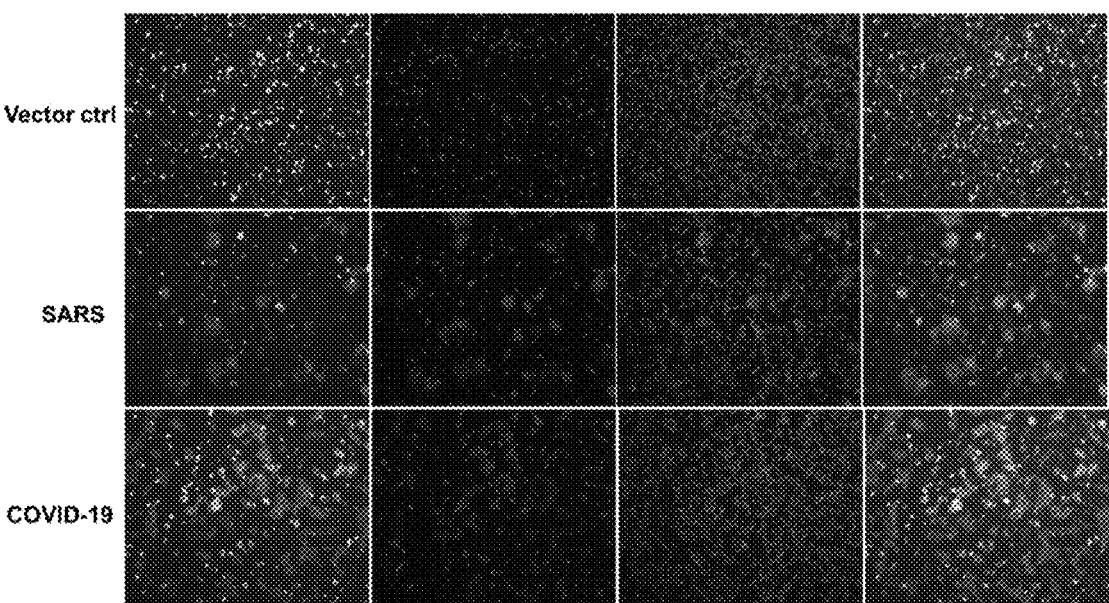
FIG. 2 shows that the spike protein of the new coronavirus can induce the formation of syncytia.
Figure 3:
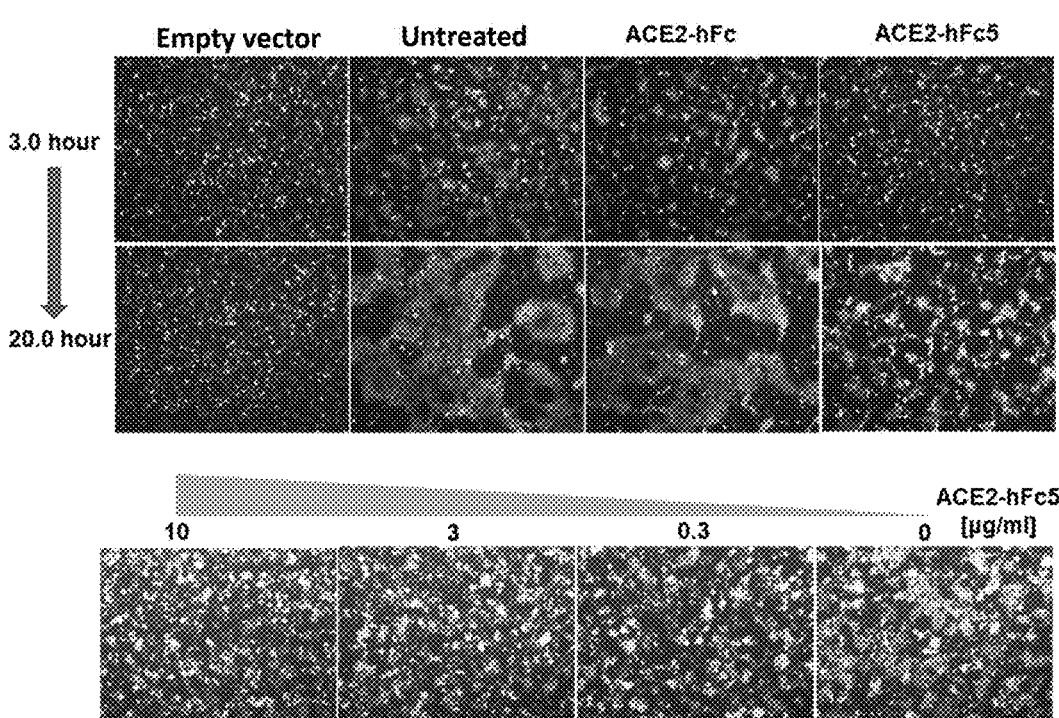
FIG. 3 shows that the ACE2-hFc5 fusion protein significantly inhibits the intercellular membrane fusion mediated by the SARS S protein in vitro.

6.2 From FIG. 2, it can be seen that a large number of syncytia were formed in both the SARS-CoV2 virus group and the SARS virus group. The largest number of syncytia were formed in the SARS-CoV2 virus group. In contrast, no cell fusion was observed in the control vector group. This result shows that the SARS-CoV2 virus S protein is similar to the SARS virus S protein, and has the ability of inducing cell fusion to form the syncytia. The SARS-CoV2 virus S protein has stronger induction ability than that of the SARS virus S protein (the top panel in FIG. 3). This also indirectly proves that the SARS-CoV2 virus S protein has a stronger affinity with the receptor hACE2 than the SARS virus S protein. When the ACE2-hFc5 fusion protein was added, it was observed that, as compared with the control protein, the ACE2-hFc5 fusion protein could significantly inhibit the SARS-CoV2 virus S protein-induced formation of syncytia, with an inhibition rate of up to 90% or more, and even completely inhibit the formation of syncytia induced by the SARS virus.

In addition, it can also be seen (the bottom panel in FIG. 3) that a large number of syncytia were formed when the cells expressing the coronavirus S protein were co-incubated with the cells expressing the receptor ACE2, It showed that the coronavirus S protein could induce a membrane fusion process after binding to the receptor ACE2. The multinucleated syncytia were more obvious at 20 h. When 10 μg/mL ACE2-hFc5 was added into the experimental system, the number of syncytia was significantly reduced, with an inhibition rate of up to 90% or more. While, the inhibitory effect of the ACE2-hFc was non-obvious under the same conditions. Further, it can be seen that the ACE2-hFc5 inhibited the formation of syncytia in a dose-dependent manner. ACE2-hFc5 still had a significant inhibitory activity for the formation of syncytia at a low concentration of 0.3 μg/mL.

The enveloped virus (including coronaviruses)-cell (inner) membrane fusion process is critical for the virus infection. The formation of syncytia is a prominent pathological change that occurs in the lungs after the SARS-CoV2 virus infects the human body. Our experimental results show that the ACE2-hFc5 fusion protein has a strong activity of inhibiting syncytia formation and can block the infection of coronaviruses, especially the SARS-CoV2.

Example 7: Cell Surface Expression and Syncytia Formation Assays for SARS-CoV2 Wild-Type S Protein and Mutated S Protein Containing Mutations in Furin Protease Cleavage Site The pCAGGS empty vector (control), and the plasmids expressing SARS-CoV2 S protein and Furin site-mutated SARS-CoV2 S protein (in which PRRAR was mutated to PSRAS) were respectively co-transfected, by PEI, with pmCherry-C1 into 293T cells. The plasmid expressing the full-length ACE2 having the extracellular, transmembrane and intracellular regions and the pEGFP-N1 vector were co-transfected into 293T cells by PEI. The cells were digested 24 h after transfection, washed once with a DMEM complete medium (10% FBS, 1×PS) and counted. A part of the empty vector-transfected control cells and the cells expressing the SARS-CoV2 S protein (SEQ ID NO: 9) (FIG. 4) and the Furin site-mutated SARS-CoV2 S protein (SEQ ID NO: 10) (FIG. 5) were then examined for the cell surface expression of the SARS-CoV2 S proteins. The remaining part of the cells was used for the examination of the syncytia formation.

Regarding the examination of the cell surface expression of the SARS-CoV2 S protein, 20 μg/mL of the ACE2-NN-Fc fusion protein was respectively incubated with the above cells on ice for 45 min, the cells were then washed three times with the FACS buffer (PBS, 0.5% BSA), followed by the addition of a FITC-anti-human-Fc-secondary antibody (F9512, Sigma) diluted at 1:300 and incubation on ice for 30 min. The surface expressions of the SARS-CoV2 S protein and the Furin site-mutated SARS-CoV2 S protein were analyzed by the flow cytometer after the cells were washed three times with the FACS buffer (PBS, 0.5% BSA). The results were analyzed with FlowJo V10 software and showed in FIG. 6.

Regarding the examination of the syncytia formation experiment, the empty vector-transfected control cells, and the cells transfected with the SARS-CoV2 S plasmid and the Furin site-mutated SARS-CoV2 S plasmid were separately seeded into a 48-well cell culture plate at 2.5E5/well. After 30 min, the ACE2-transfected cells were then added into the above wells containing cells at 2.5E5/well. After continuous co-culture in a 5% CO$_2$ cell incubator at 37° C. for 3 h, the formation of viral syncytia was observed under a fluorescence microscope. The experimental results were photographed and recorded. As shown in FIG. 7, neither cell fusion nor the formation of multinucleated syncytia was observed between the empty vector-transfected control cells (marked in red) and the cells expressing the human full-length ACE2 (marked in green). In contrast, a large number of multinucleated syncytia was formed after co-culture of the wild-type S protein-expressing cells (marked in red) with the cells expressing the human full-length ACE2 (marked in green) for 3 h. When the Furin cleavage site RRAR in the SARS-CoV2 S protein was mutated to SRAS, the cell membrane fusion was completely inhibited, and no multinucleated syncytia were observed. This indicates that the mutated S protein lost the ability of mediating the cell membrane fusion. Therefore, the Furin site in the SARS-CoV2 S protein is necessary for the S protein-mediated cell fusion.

Moreover, the Furin protease cleavage site-mutated SARS-CoV2 S protein has a significant effect in inhibiting virus-cell fusion and the formation of the multinucleated syncytia (see the rightmost image in FIG. 7).

Example 8: Affinity and Avidity Analysis of Different Forms of ACE2-hFc Fusion Proteins

8.1 Methods

The affinity (BIAcore T200) and avidity (Fortebio Octet RED384) of the ACE2-NN-hFc and ACE2-NN-hFc5 fusion proteins with the receptor binding region (RBD) (aa331-527) of the coronavirus (SARS-CoV-2) S protein were detected by surface plasmon resonance (SPR) and bio-layer interferometry (BLI), respectively.

In the affinity assay, the ACE2-hFc and ACE2-hFc5 fusion proteins were first captured on the surface of a CM5 biosensor chip coated with an anti-human Fc antibody. Then, 2-fold serial dilutions between 200 nM and 6.25 nM of the SARS-CoV-2 RBD protein, which has a His6-Avi tag at the C-terminal, were flowed through the chip at a rate of 30 μL/min, to detect the intermolecular binding and dissociation kinetics of the proteins. The 1:1 Langmuir binding model (BIA Evaluation Software) was used to calculate the association constant (Ka), dissociation constant (Kd), and equilibrium dissociation constant (KD). Regarding the avidity assay, 20 μg/mL of the SARS-CoV-2 RBD protein with a C-terminal His6-Avi tag was first captured on the surface of a streptavidin biosensor. Then, different concentrations of ACE2-hFc (0 nM, 2-fold serial dilutions between 1.65-105.3 nM) and ACE2-hFc5 fusion proteins (0 nM, 2-fold serial dilutions between 8.22-526.3 nM) were used as analytes, for binding to the RBD-bound sensor surface for 180 seconds, followed by dissociation for 300 seconds. The 1:1 binding model (Fortebio data Analysis 11.1-knetics software) was used to calculate the binding constants Ka, Kd and KD.

8.2 Results

Figure 9:
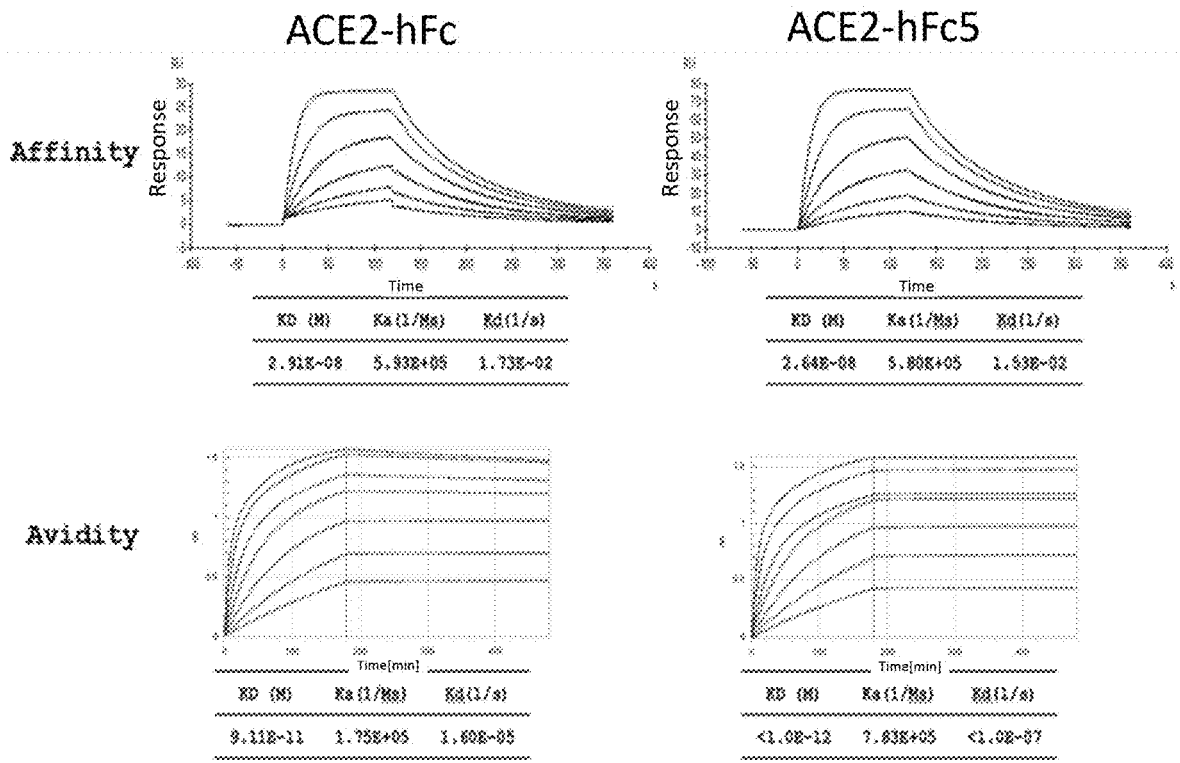
FIG. 9 shows affinity and avidity of the ACE2-hFc and ACE2-hFc5 fusion proteins with the RBD region of the SARS-CoV2 spike protein.

By employing a method for determining the affinity of monovalent binding (BIAcore T200) (FIG. 9), it was found that the ACE2-hFc and ACE2-hFc5 fusion proteins had the same affinity for the SARS-CoV-2 RBD, i.e., 26.4 nM and 29.1 nM, respectively. Fortebio was used to analyze the avidity of the ACE2-NN-hFc and ACE2-NN-hFc5 fusion proteins with the S protein RBD. In the experiments, 20 μg/mL of the RBD-His-avi protein was captured on the surface of the streptavidin biosensor, and different concentrations of the ACE2-NN-hFc and ACE2-NN-hFc5 fusion proteins were used as the mobile phases. Octet DataAnalysis 11.0 software was used to analyze the experimental data, and 0 nM was used as the background value for subtraction. The results show (FIG. 9) that, as compared with the ACE2-hFc fusion protein, the multimerized ACE2-hFc5 fusion protein significantly enhances the affinity with the spike protein RBD-His-avi, with KD values (<1.0 E-12 M) beyond the detection range of the instrument.

Example 9: In Vitro Coronavirus Pseudovirus Neutralization Experiment

9.1 Methods

9.1.1 Package of Coronavirus Pseudovirus

Regarding the package the pseudovirus of a coronavirus strain (D614), HEK293T cells were inoculated in a 10 cm cell culture dish. When the cells reached 80% confluence, a coronavirus full-length S protein expression plasmid pSARS-CoV2 S-C9 (D614) was co-transfected with the packaging plasmid psPAX2 and a fluorescein expression plasmid pHIV-Luc, at a ratio of 1:3:4, by means of Lipofactamine 3000 The medium was discarded after 6 h of the transfection, and fresh DMEM medium containing 2% FBS and penicillin was added and continuously cultured for 48 h. Then, the culture supernatant containing pseudovirus particles was collected, centrifuged and filtered to remove cell debris, and frozen at −80° C. for future use. For the package of other SARS-CoV-2 variants, SARS and pangolin coronaviruses, the preparation conditions were the same except that the pSARS-CoV2 S-C9 (D614) was replaced with a plasmid expressing the S proteins of the variants. The coronavirus pseudoviruses used in the present disclosure include: SARS-CoV2 initial strain D614; SARS-CoV2 initial strain D614 having mutated Furin site; SARS-CoV2 main epidemic strain G614; SARS-CoV2 variant D614 (L18F; A22V; V367F; N439K; Y453F; N501Y; T478I; P1263L); SARS; and, pangolin coronavirus.

9.1.2 Neutralization Experiments of Coronavirus Pseudovirus

In the neutralization experiments of the coronavirus pseudovirus, 293T-ACE2 cells stably expressing human ACE2 were first seeded on an opaque 96-well cell culture plate at 1E5/well, and cultured in a $CO_2$ incubator at 37° C. for 20 h for the neutralization experiment. On the day of the experiment, 75 μL of the coronavirus pseudoviruses were uniformly mixed with 25 μL of different forms of serial diluted soluble ACE2 fusion proteins, followed by incubation at room temperature for 30 min. Then, the cell culture supernatant in the 96-well cell culture plate was discarded. The premixed pseudovirus-ACE2 fusion protein mixtures were then added to 293T-ACE2 cells. After incubating in a $CO_2$ incubator at 37° C. for 24 h, fresh DMEM medium containing 2% FBS was added instead to continue the culture. After 24 h, the luciferase activity was measured by means of a Bright-Glo luciferase assay system and a microplate luminometer. In the experiment, at least two duplicate wells and a PBS control well were provided.

9.2 Results

Figure 10:
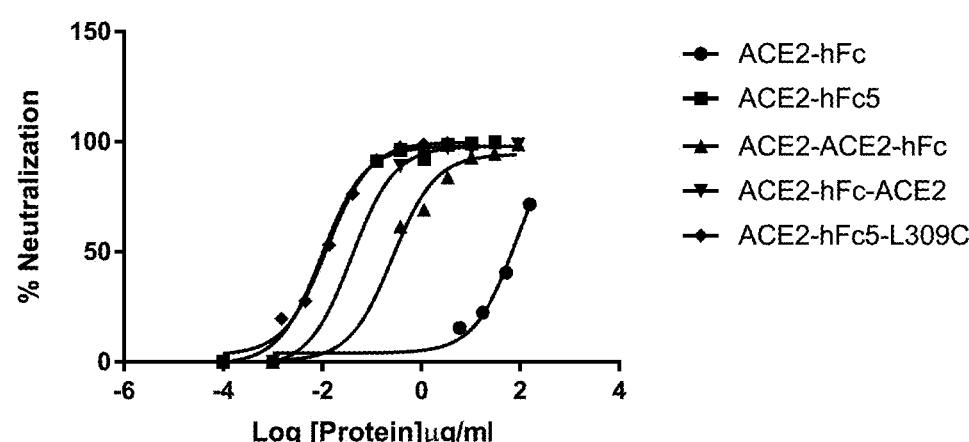
FIG. 10 shows that different forms of ACE2 fusion protein multimers inhibit the infection of a SARS-CoV2 pseudovirus (D614).
Figure 11:
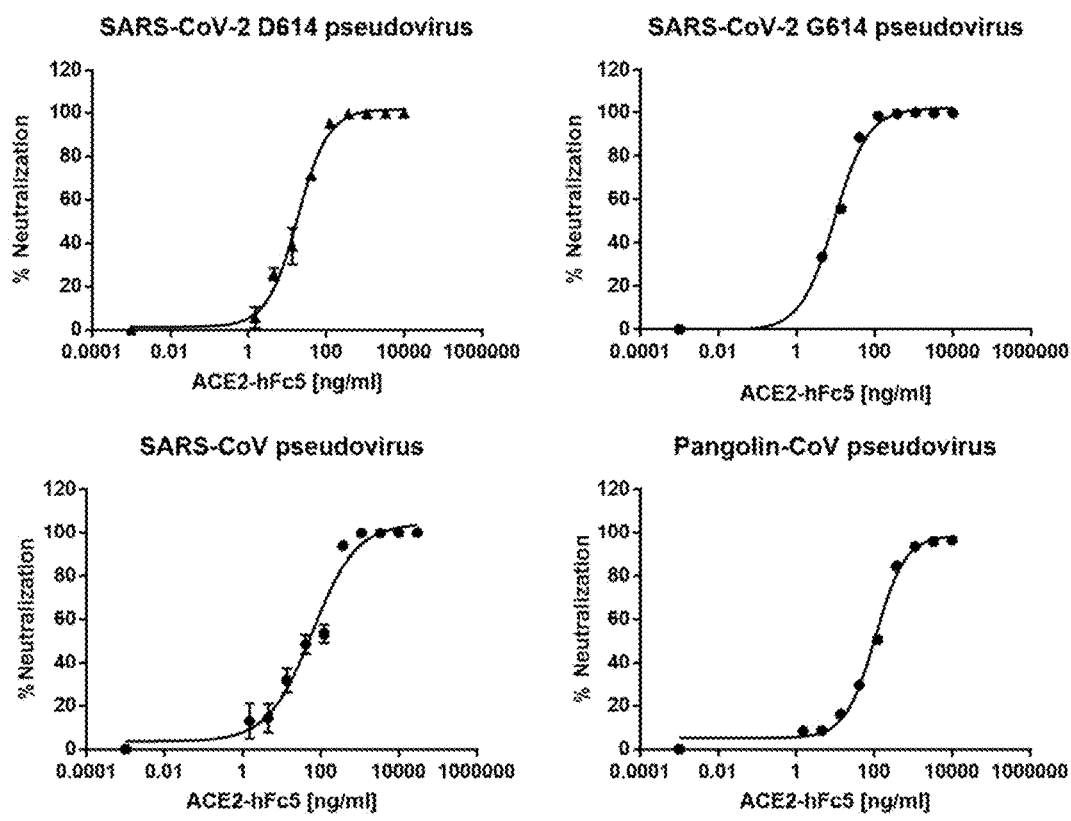
FIG. 11 shows that the ACE2-hFc5 fusion protein inhibits the infections of SARS-CoV2 pseudoviruses D614 and G614, a SARS virus, and a pangolin-CoV pseudovirus.

9.2.1 Neutralization of Coronavirus Pseudovirus Infection by Different Forms of ACE2-hFc Fusion Protein Multimers Regarding the comparison of the different forms of ACE2-hFc fusion proteins for neutralizing the coronavirus pseudovirus infection, 293T cells stably expressing human ACE2 were used as the host cells, and the serially diluted ACE2-NN-hFc fusion proteins were mixed with the SARS-CoV-2 pseudoviruses to infect 293T-ACE2 cells. The intracellular luciferase activity (RLU) was detected on the second day after the infection. The percentage inhibition of the ACE2-NN-hFc fusion proteins at different concentrations was calculated based on the RLU of the virus-infected PBS control group. As shown in FIG. 10, the different forms of ACE2-hFc fusion proteins all have neutralizing activity against the SARS-CoV-2 pseudovirus D614 infection. In particular, the ACE2-hFc5 and the ACE2-hFc5 L309C have the strongest in vitro neutralizing activity, with IC50s of 9.86 ng/mL and 12.4 ng/mL respectively, followed by the ACE2-hFc-ACE2 tetramer and ACE2-ACE2-hFc tetramer with IC50s of 39.31 ng/mL and 260.8 ng/mL respectively, and the ACE2-NN-hFc has the worst neutralizing activity. This result indicates that the activity of the ACE2 fusion proteins for neutralizing the SARS-CoV-2 infection is proportional to their affinity with the S protein RBD, i.e, the higher the degree of multimerization, the better the neutralization effect. Thus, the neutralizing activity of the ACE2-hFc fusion protein is significantly enhanced by the multimerization modification.

Figure 1:
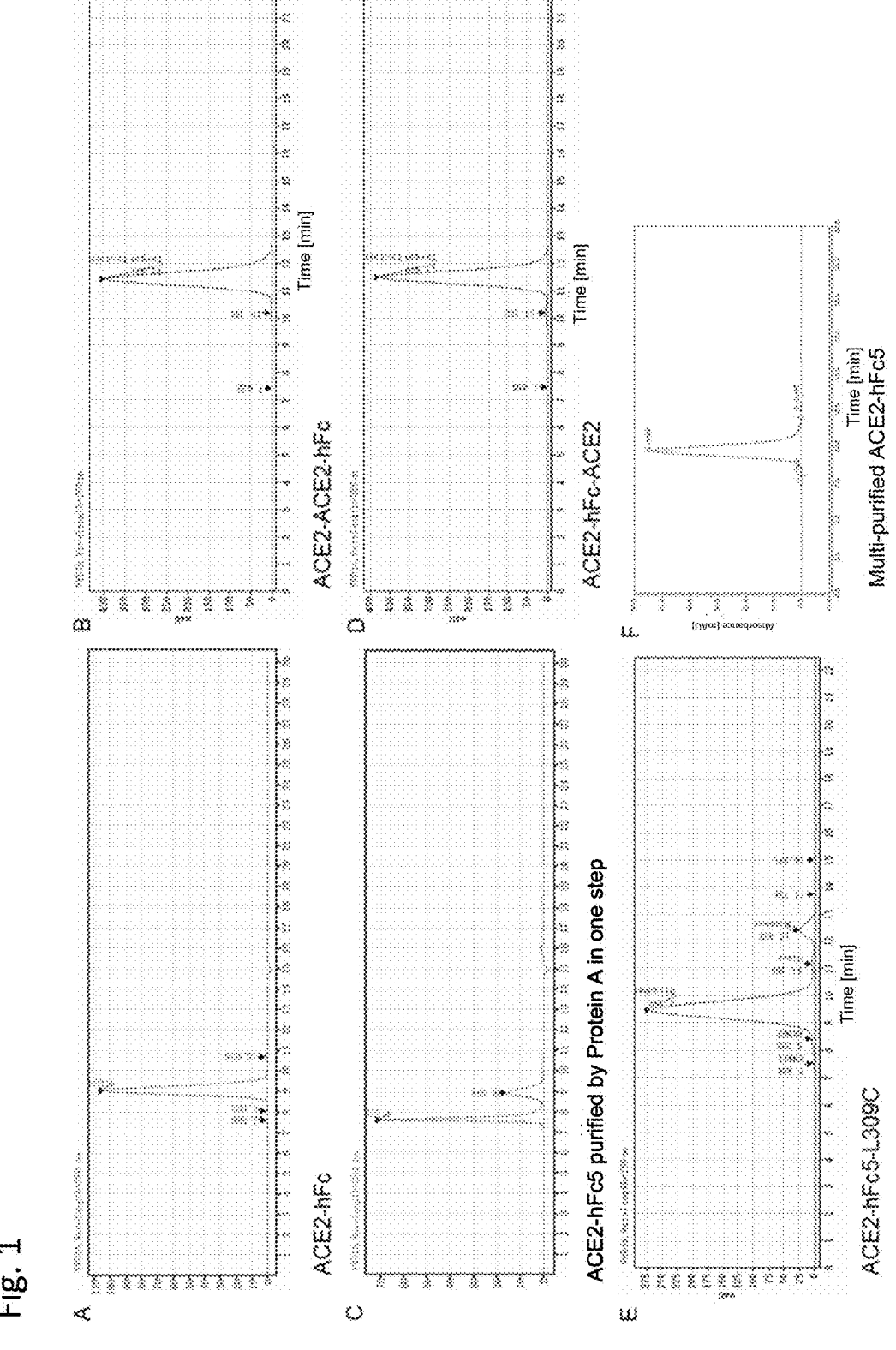
FIG. 1 shows SEC-HPLC peaks of fusion proteins ACE2-hFc-ACE2, ACE2-ACE2-hFc, ACE2-hFc5 and ACE2-hFc5-L309C obtained after purification.

9.2.2 Broad-Spectrum Neutralizing Activity of ACE2-NN-hFc5 Against Coronavirus Infection In order to evaluate the broad-spectrum anti-infection activity of ACE2-NN-hFc5 against SARS-CoV-2 variants and related coronaviruses, we packaged multiple SARS-CoV-2 single-point mutant pseudoviruses based on the main prevalent variants present in the population, and evaluated the neutralizing activity of ACE2-NN-hFc5 by using the infection model of the 293T-ACE2 stable cell line. The results show that ACE2-NN-hFc5 has strong neutralizing activity and broad-spectrum antiviral activity against the initial strain D614, the main epidemic strain G614 and other SARS-CoV-2 variants, as well as SARS virus and pangolin coronavirus pseudovirus. ACE2-NN-hFc5 has neutralizing activity IC50 of 9.56 ng/mL for the main epidemic strain G614 pseudovirus (FIG. 1 and Table 2 below). In terms of the neutralizing activity for the pseudovirus infection of the main SARS-CoV-2 variants (see Table 3), the results show that the ACE2-NN-hFc5 multimer has a strong in vitro neutralizing ability. In particular, ACE2-NN-hFc5 has stronger neutralizing activity with IC50 of 0.036 ng/mL for the N501Y variant. These results indicate that ACE2-NN-hFc5 has high-efficiency and broad-spectrum anti-coronavirus activity in vitro.

sample. The 2019-nCoV (virus strain: C-Tan-nCoV Wuhan strain 01) was diluted to 200 $TCID_{500}/100$ μL with the 2% FBS-DMEM medium. 50 μL of the diluted sample was added with an equal volume of 200 $TCID_{50}$ virus, and incubated at 37° C. for 1 h. 100 μL of the antibody-virus complexes were then added into the cells and incubated at 37° C. CPE was observed after incubation at 37° C. for 48 h. 100 μL of the culture supernatant was aspirated after 48 h for nucleic acid extraction, and 80 μL of an eluate was used for elution finally. 5 μL of nucleic acid extracts were taken to formulate a real-time fluorescent RT-PCR reaction mixture, which was analyzed on an ABI Q5 fluorescence quantitative PCR system. A standard curve was used to determine the virus $TCID_{50}$ of the samples based on the measured CT values of the samples, according to the following formula: virus replication inhibition rate (%)=(control $TCID_{50}$-fusion protein $TCID_{50}$)/control $TCID_{50}\times100\%$. The above experiment was completed in a Biosafety Level 3 laboratory.

10.2 Results

Figure 12:
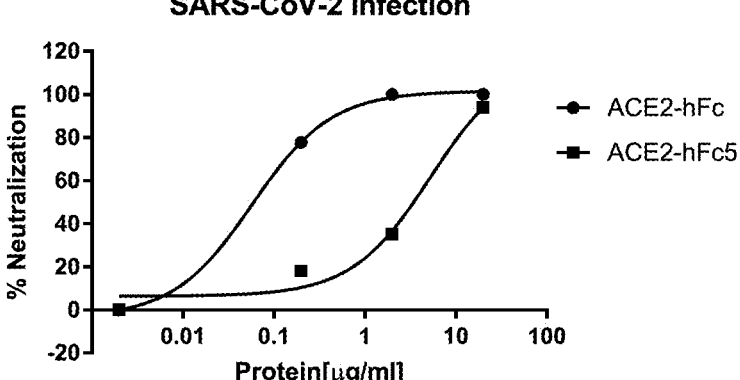
FIG. 12 shows that the ACE2-hFc5 fusion protein inhibits the infection of SARS-CoV2 live virus.

The neutralization effect of ACE2-hFc5 on live 2019-nCoV (C-Tan-nCoV Wuhan strain 01) virus was evaluated in a biosafety laboratory using Vero cells as the host cells. The experimental results show (FIG. 12) that both ACE2-hFc5 and ACE2-hFc have significant neutralizing activity against the infection of the coronavirus, with IC50 of 0.02-0.06 μg/mL and 5.3-6.8 μg/mL, respectively. ACE2-NN-hFc5 has better in vitro neutralization effect (which is hundreds of times higher than that of ACE2-NN-hFc), and 80% inhibition of the virus can still be observed at a concentration of 0.2 μg/mL. The above results fully demonstrate that ACE2-NN-hFc5 has an efficient anti-coronavirus activity in vitro.

TABLE 2

| | SARS-CoV2 initial strain D614 | SARS-CoV2 main epidemic strain G614 | SARS virus | pangolin coronavirus |
|---|---|---|---|---|
| | | | | |

Neutralizing Activity of ACE2-hFc5 Multimer against SARS-CoV-2 D614 and G614 strains, SARS virus, and Pangolin Coronavirus Pseudovirus Infection.

| | SARS-CoV2 initial strain D614 | SARS-CoV2 main epidemic strain G614 | SARS virus | pangolin coronavirus |
|---|---|---|---|---|
| $IC_{50}$(ng/mL) | 17.09 ± 7.08 | 9.56 ± 0.25 | 84.54 ± 33.4 | 108.2 |

TABLE 3

Neutralizing Activity of ACE2-hFc5 Multimer against Pseudovirus Infection of SARS-CoV-2 Main Variants.

| | SARS-CoV-2 variant pseudovirus | | | | | | | |
|---|---|---|---|---|---|---|---|---|
| | L18F | A222V | V367F | N439K | Y453F | N501Y | T478I | P1263L |
| IC50(ng/mL) | 0.669 | 1.151 | 1.975 | 0.2668 | 0.8352 | 0.036 | 0.86 | 2.168 |

Example 10: In Vitro Live Virus Neutralization Assay for SARS-CoV-2

10.1 Method

Vero cells were seeded into a 96-well plate at a density of approximately 2×10⁴ cells/well. On the following day, the cell culture medium was changed to 2% FBS-DMEM medium. The ACE2-hFc fusion protein was diluted with the 2% FBS-DMEM medium to working concentrations of 20 μg/mL, 2 μg/mL and 0.2 μg/mL, three replicate wells per

Example 11: Nebulizer Inhalation Evaluation of ACE2-hFc5 Fusion Protein in Hamsters

11.1 Methods

11.1.1 Deposition and Distribution Analysis of ACE2-NN-hFc5 in Respiratory Tracts and Lungs after Nebulizer Inhalation We selected a systemic exposure nebulizer delivery system for small animals, which included an air pump, a mass flow meter and an exposure box, for delivering Nebulized ACE2-hFc5. The nebulizer delivery system matched with an Aerogen solo nebulizer, an adapter and a nebulization collection device. For analysis of the deposition and distribution of the drug in respiratory tracts, the nasal lavage fluids (NLFs) of hamsters were collected by rinsing with normal saline at 0 h, 6 h and 24 h after drug delivery, respectively. The main trachea, bronchus and alveoli were collected and a portion of each was lysed with a tissue lysis buffer. The supernatant was taken by centrifugation to detect the contents of the ACE2-hFc5 multimers. For analysis of the deposition doses in lungs, each hamster was lavaged with 4 mL of normal saline to collect the bronchoalveolar lavage fluid (BALF), 15 min, 30 min and 60 min after nebulizer inhalation. The lungs were further taken out and homogenized. A proportion of lung homogenate was lysed with the tissue lysis buffer, and then the supernatant was taken by centrifugation to detect the contents of ACE2-hFc5 multimers.

11.1.2 ELISA Analysis of the Contents of ACE2-hFc5

The contents of ACE2-hFc5 multimers were analyzed using ELISA assay for binding SARS-CoV-2 RBD. In particular, 2 µg/mL of streptavidin was coated for capturing 2 µg/mL of biotin-labeled SARS-CoV-2 RBD. The diluted lavage fluid or tissue lysis supernatant to be tested was added while using the purified ACE2-NN-hFc5 as a standard. An HRP-labeled anti-hFc secondary antibody was used for detection. $OD_{450}$-$OD_{630}$ values were read with a microplate reader.

11.1.3 SEC-HPLC Analysis of Multimer Forms of ACE2-hFc5 Before and After Nebulization ACE2-hFc5 multimers before and after nebulization were subjected to aggregation and degradation analysis by an HPLC method. An Agilent 1260 high performance liquid chromatography analysis system, a G4000 TSK G4000SWx1 analytical column and a TSK gel guard column SWx1 were used. The buffer comprised 50 mM PB and 300 mM NaCl pH 6.7±0.1. The analysis was performed for 20 or 25 min at a flow rate of 0.8 mL/min.

Figure 13:
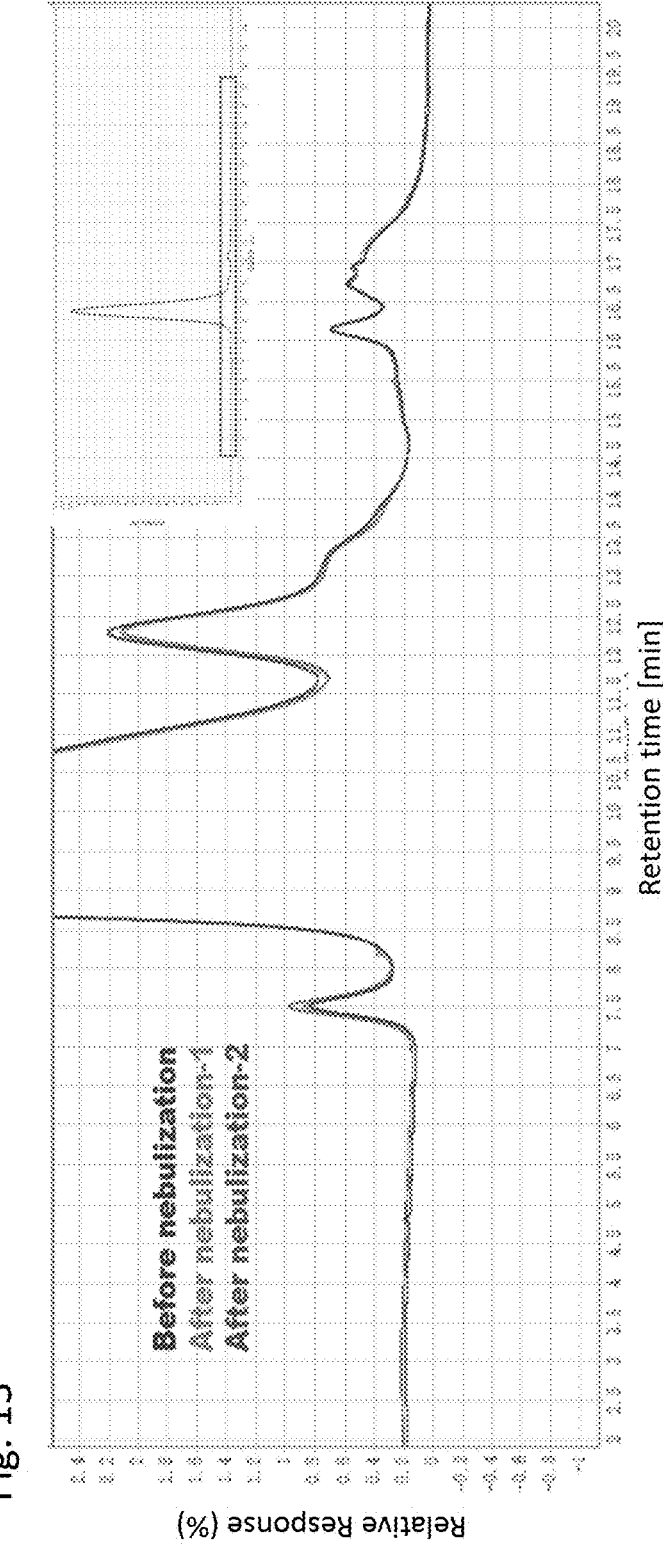
FIG. 13 shows the physicochemical properties of ACE2-hFc5 before and after nebulization as analyzed by SEC-HPLC.

11.2 Result: ACE2-NN-hFc5 can be Effectively Deposited in Hamster Alveoli Through Nebulizer Administration We explored the route of administration via the respiratory tract through nebulizer inhalation, since SARS-CoV-2 mainly causes infection of the respiratory tract, and the focus of infection mainly locates in the lung. We nebulized ACE2-hFc5 using the Aerogen's nebulizer and collected the nebulized droplets using matched glass tubes under ice bath with the recovery rate of 90% or more. We analyzed, by SEC-HPLC, the physicochemical properties of ACE2-hFc5 before and after nebulization, and its neutralizing activity against the infection of the SARS-CoV-2 pseudovirus. The results show that the nebulization does not cause aggregation and degradation of ACE2-NN-hFc5 (FIG. 13). Further, it shows that ACE2-NN-hFc5 can significantly inhibiting the infection of the SARS-CoV-2 pseudovirus, and its antiviral ability does not change significantly before and after nebulization (FIG. 14).

The nebulizer delivery system for small animals is further used to perform the administration through nebulizer inhalation (5 mg/mL ACE2-NN-hFc5) for the hamsters for 50 min. The nasal lavage fluid (NLF), main trachea, bronchus and alveoli of the hamsters were taken at 0 h, 6 h and 24 h after nebulization to analyze the deposition and distribution of ACE2-NN-hFc5 in each part of the respiratory tract. We found that the inhaled ACE2-hFc5 was mainly distributed in the alveoli (about 75%) at 0 h, 6 h and 24 h after inhalation. The distribution of ACE2-hFc5 in the NLF decreased rapidly, from 17.33% at 0 h to 0.7% at F24 h after inhalation. The distribution of ACE2-hFc5 in the main trachea was less, ranging from 0.35% to 3.4%. The distribution of ACE2-hFc5 in the bronchus gradually increased from 5% to 19%. These results indicate that the inhaled ACE2-NN-hFc5 can effectively reach the alveoli, and mainly distribute in the alveoli within 24 h after inhalation.

We further investigated the relationship between the inhaled doses of ACE2-hFc5 and the lung deposition in hamsters, and analyzed the neutralizing activity for the pseudoviruses in the BALF. We collected the BALF and lung homogenate from the hamsters after the nebulizer inhalation of ACE2-hFc5 at a concentration of 5 mg/mL for 15 min, 30 min and 60 min. Then, contents of the ACE2-hFc5 were detected by ELISA. The amounts of the ACE2-NN-hFc5 in both the BALF and lung homogenate were calculated as the total amount of lung deposition. The results show that, after the nebulizer inhalation of the ACE2-hFc5, the amount of lung deposition in the the hamsters increases with the increasing doses. The deposition amounts correspond to 6.48 µg, 18.69 µg and 33.35 µg for inhalation for 15 min, 30 min and 60 min, respectively. The deposition amounts of ACE2-hFc5 in the hamster lungs decreased rapidly after the inhalation. The deposition amounts at 12 hours after the inhalation were 14.73%-46% of that immediately after the inhalation. Nonetheless, when inhaling for 15 min and 30 min, the BALF obtained from the hamsters, each of which was lavaged with 4 mL of normal saline at 12 hours after inhalation, could still maintain 90% or more of the neutralizing activity against the SARS-CoV-2 pseudoviruses after being diluted 4 times.

Example 12: Efficacy Evaluation of ACE2-NN-hFc5 in a Hamster Model for New Coronavirus (SARS-CoV-2) Infection

12.1 Method

12.1.1 Experimental Design

All animal experiments were approved by the Animal Ethics Committee of the Kunming Institute of Biomedical Sciences of the Chinese Academy of Medical Sciences, and complied with the laboratory practice and guidelines of the National Kunming High-Level Biosafety Laboratory in Yunnan, China.

Adult Specific-Pathogen-Free (SPF) hamsters were transferred to the high-level biosafety laboratory and raised individually in respective cages. The hamsters were equally divided into three groups based on the body weights: an untreated control group; a group subjected to nebulized treatment for 15 min twice daily; and a group subjected to nebulized treatment for 30 min twice daily, with 7 hamsters in each group. In the experiment, the hamsters were inoculated with $10^4$ PFU of SARS-CoV-2 viruses (GD108 #) through nasal cavities. 2 hours later, the first nebulization inhalation was performed, with nebulization for 15 min (25 mg ACE2-hFc5) and 30 min (50 mg ACE2-hFc5), respectively. The nebulization inhalation was performed once every 12 hours, for a total of 6 times. The hamsters were weighed before each of the nebulization inhalations. The experiment ended at 62 h after the virus challenge. The lung tissues were taken for SARS-CoV-2 viral (gRNA) and subviral (sgRNA) genomic load analysis. 1 mL of PBS was added per 100 mg of the lung tissue (left lung). 200 μL was taken for RNA extraction after rapid homogenization, followed by RT-qPCR assay for SARS-CoV-2 viral gRNA and sgRNA load analysis. Statistical analysis was performed by using GraphPad Prism 8 software. Two-tailed Mann-Whitney U was used for the analysis of differences between two groups.

12.2 Results: The Nebulizer Administration of ACE2-hFc5 can Effectively Reduce the Viral Load in the Hamster Model for SARS-CoV-2 Infection Based on the established nebulizer inhalation delivery mode, we evaluated the in vivo antiviral ability of the ACE2-NN-hFC5 using the hamster model for SARS-CoV-2 infection. Two dose groups were provided in the experiment to evaluate the efficacy of the ACE2-hFC5, one with nebulizer inhalation for 15 minutes and the other with nebulizer inhalation for 30 minutes. The virus titers reached the highest on the third day after the hamsters were infected with SARS-CoV-2, and viremia was gradually improved with time. Thus, we chose the third day after the virus challenge as the experimental endpoint. After treatment with ACE2-NN-hFc5, there was a slight improvement trend in the reduction of the hamster body weights. According to the quantitative results of gRNA and sgRNA in the lung tissues, the nebulizer inhalation of ACE2-hFc5 can significantly inhibit the replication of SARS-CoV-2 virus in the lung tissues (FIG. 15). In FIG. 15, qPCR analysis was performed at the end of the experiment (62 hours after the challenge) to determine the changes of the SARS-CoV-2 genome (gRNA) and subgenome (sgRNA) in the hamster lungs. ● represents the untreated control group; ■ represents the ACE2-hFc5-15 min-BID group; ▲ represents the ACE2-hFc5-30 min-BID group; and the horizontal line represents a median. Mann-Whitney U was used for statistical analysis of differences between two groups. Therefore, the nebulizer inhalation of ACE2-hFc5 can effectively reduce the viral load in the hamster model for SARS-CoV-2 infection, and has the potential to prevent and treat the pneumonia caused by SARS-CoV-2.

Although the present disclosure has been described in detail above with general description, specific embodiments and experiments, some modifications or improvements can be made on the basis of the present disclosure, which is obvious to those skilled in the art. Therefore, these modifications or improvements made without departing from the spirit of the present disclosure all fall within the scope of protection of the present disclosure.

---

What is claimed:

1. An Fc fusion protein multimer ACE2-hFc(n) comprising n polypeptide monomer units, wherein each of the polypeptide monomer units is a dimer in which two soluble angiotensin-converting enzyme 2 (ACE2) truncated forms are linked to N-terminal ends of two heavy chain Fc domains of an antibody respectively, wherein said n polypeptide monomer units are further assembled into the Fc fusion protein multimer ACE2-hFc(n) via a tail located at each C-terminal end of the two heavy chain Fc domains, wherein each of the two ACE2 truncated forms comprises an extracellular domain of ACE2, and comprises the amino acid sequence as shown by SEQ ID NO: 1 or SEQ ID NO: 2, wherein the tail is an IgM derived tail and comprises the sequence as shown by SEQ ID NO: 17, wherein each of the two heavy chain Fc domains has a hinge region at its N-terminal, a CH2 domain and a CH3 domain of the antibody, wherein the antibody is an IgG1 antibody, and wherein n is selected from 4, 5 or 6.

2. The Fc fusion protein multimer according to claim 1, wherein the C-terminal end of each of the two heavy chain Fc domains is linked to the tail, and the n polypeptide monomer units have a total of 2n tails, which are connected to each other to form the Fc fusion protein multimer.

3. The Fc fusion protein multimer according to claim 1, wherein the Fc fusion protein multimer comprises one or more selected from the following group:

ACE2-hFc4, being a tetramer assembled from 4 polypeptide monomer units via the tails located at the C-terminal ends of the Fc domains, wherein each of the polypeptide monomer units comprises a dimer composed of two ACE2 truncated forms and two heavy chain Fc domains, and wherein one ACE2 truncated form, and one heavy chain Fc domain along with the tail comprise an amino acid sequence as shown by SEQ ID NO: 7; or ACE2-NN-hFc4, being a tetramer assembled from 4 polypeptide monomer units via the tails located at the C-terminal ends of the Fc domains, wherein each of the polypeptide monomer units comprises a dimer composed of two ACE2 truncated forms and two heavy chain Fc domains, and wherein one ACE2 truncated form, and one heavy chain Fc domain along with the tail comprise an amino acid sequence as shown by SEQ ID NO: 8; or ACE2-NN-hFc4-L309C, being a tetramer assembled from 4 polypeptide monomer units via the tails located at the C-terminal ends of the Fc domains, wherein each of the polypeptide monomer units comprises a dimer composed of two ACE2 truncated forms and two heavy chain Fc domains, and wherein one ACE2 truncated form, and one heavy chain Fc domain along with the tail comprise an amino acid sequence as shown by SEQ ID NO: 18, and the heavy chain Fc domain has an L309C mutation at position 309; or ACE2-hFc5, being a pentamer assembled from 5 polypeptide monomer units via the tails located at the C-terminal ends of the Fc domains, wherein each of the polypeptide monomer units comprises a dimer composed of two ACE2 truncated forms and two heavy chain Fc domains, and wherein one ACE2 truncated form, and one heavy chain Fc domain along with the tail comprise an amino acid sequence as shown by SEQ ID NO: 7; or ACE2-NN-hFc5, being a pentamer assembled from 5 polypeptide monomer units via the tails located at the C-terminal ends of the Fc domains, wherein each of the polypeptide monomer units comprises a dimer composed of two ACE2 truncated forms and two heavy chain Fc domains, and wherein one ACE2 truncated form, and one heavy chain Fc domain along with the tail comprise an amino acid sequence as shown by SEQ ID NO: 8; or ACE2-NN-hFc5-L309C, being a pentamer assembled from 5 polypeptide monomer units via the tails located at the C-terminal ends of the Fc domains, wherein each of the polypeptide monomer units comprises a dimer composed of two ACE2 truncated forms and two heavy chain Fc domains, and wherein one ACE2 truncated form, and one heavy chain Fc domain along with the tail comprise an amino acid sequence as shown by SEQ ID NO: 18, and wherein the heavy chain Fc domain comprises an L309C mutation at position 309; or ACE2-hFc6, being a hexamer assembled from 6 polypeptide monomer units via the tails located at the C-terminal ends of the Fc domains, wherein each of the polypeptide monomer units comprises a dimer composed of two ACE2 truncated forms and two heavy chain Fc domains, and wherein one ACE2 truncated form, and one heavy chain Fc domain along with the tail comprise an amino acid sequence as shown by SEQ ID NO: 7; or ACE2-NN-hFc6, being a hexamer assembled from 6 polypeptide monomer units via the tails located at the C-terminal ends of the Fc domains, wherein each of the polypeptide monomer units comprises a dimer composed of two ACE2 truncated forms and two heavy chain Fc domains, and wherein one ACE2 truncated form, and one heavy chain Fc domain along with the tail comprise an amino acid sequence as shown by SEQ ID NO: 8; or ACE2-NN-hFc6-L309C, being a hexamer assembled from 6 polypeptide monomer units via the tails located at the C-terminal ends of the Fc domains, wherein each of the polypeptide monomer units comprises a dimer composed of two ACE2 truncated forms and two heavy chain Fc domains, and wherein one ACE2 truncated form, and one heavy chain Fc domain along with the tail comprise an amino acid sequence as shown by SEQ ID NO: 18.

4. The Fc fusion protein multimer according to claim 1, wherein the soluble ACE2 truncated forms are glycosylated.

5. The Fc fusion protein multimer according to claim 1, wherein each of the two soluble ACE2 truncated forms is glycosylated at position(s) 53, 90, 103, 322, 432, 546 and/or 690 of human ACE2.

6. A pharmaceutical composition comprising: the Fc fusion protein multimer according to claim 1; and a pharmaceutically acceptable carrier.

7. A method for treating or preventing an ACE2-related disease, comprising administrating to a subject a therapeutically effective amount of the pharmaceutical composition of claim 6.

8. The method according to claim 7, wherein the disease is caused by an infection of a virus employing ACE2 as a receptor.

9. The method according to claim 7, wherein the disease is selected from pneumonia, severe acute respiratory infection, renal failure, heart failure, adult respiratory distress syndrome (ARDS), liver injury, intestinal disease, or severe acute respiratory syndrome.

10. The method according to claim 7, wherein the method is used for passive immunization of a medical worker or a person at risk of exposure to the virus.

11. The method according to claim 7, wherein the pharmaceutical composition is administered by inhalation, intranasal or airway instillation, ocular injection, middle ear injection, ear drops, topical injection, transdermal injection, parenteral injection, subcutaneous injection, intravenous injection, intradermal injection, intramuscular injection, intrapleural instillation, intraperitoneal injection, intralesional administration, application to mucosa, or transplantation of a sustained-release carrier.

12. The method according to claim 7, wherein the disease is caused by an infection of a virus comprising a coronavirus.

13. The method according to claim 12, wherein the virus is selected from the group consisting of SARS-COV, HCoV-NL63 and SARS-CoV2.

* * * * *

SEQUENCE LISTING

<160> NUMBER OF SEQ ID NOS: 18

<210> SEQ ID NO 1
<211> LENGTH: 596
<212> TYPE: PRT
<213> ORGANISM: Homo sapiens

<400> SEQUENCE: 1

```
Thr Ile Glu Glu Gln Ala Lys Thr Phe Leu Asp Lys Phe Asn His Glu
1               5                   10                  15

Ala Glu Asp Leu Phe Tyr Gln Ser Ser Leu Ala Ser Trp Asn Tyr Asn
            20                  25                  30

Thr Asn Ile Thr Glu Glu Asn Val Gln Asn Met Asn Asn Ala Gly Asp
        35                  40                  45

Lys Trp Ser Ala Phe Leu Lys Glu Gln Ser Thr Leu Ala Gln Met Tyr
    50                  55                  60

Pro Leu Gln Glu Ile Gln Asn Leu Thr Val Lys Leu Gln Leu Gln Ala
65                  70                  75                  80

Leu Gln Gln Asn Gly Ser Ser Val Leu Ser Glu Asp Lys Ser Lys Arg
                85                  90                  95

Leu Asn Thr Ile Leu Asn Thr Met Ser Thr Ile Tyr Ser Thr Gly Lys
            100                 105                 110

Val Cys Asn Pro Asp Asn Pro Gln Glu Cys Leu Leu Leu Glu Pro Gly
            115                 120                 125

Leu Asn Glu Ile Met Ala Asn Ser Leu Asp Tyr Asn Glu Arg Leu Trp
    130                 135                 140

Ala Trp Glu Ser Trp Arg Ser Glu Val Gly Lys Gln Leu Arg Pro Leu
145                 150                 155                 160

Tyr Glu Glu Tyr Val Val Leu Lys Asn Glu Met Ala Arg Ala Asn His
            165                 170                 175

Tyr Glu Asp Tyr Gly Asp Tyr Trp Arg Gly Asp Tyr Glu Val Asn Gly
```

```
                 180              185              190
Val Asp Gly Tyr Asp Tyr Ser Arg Gly Gln Leu Ile Glu Asp Val Glu
        195              200              205

His Thr Phe Glu Glu Ile Lys Pro Leu Tyr Glu His Leu His Ala Tyr
        210              215              220

Val Arg Ala Lys Leu Met Asn Ala Tyr Pro Ser Tyr Ile Ser Pro Ile
225              230              235              240

Gly Cys Leu Pro Ala His Leu Leu Gly Asp Met Trp Gly Arg Phe Trp
                 245              250              255

Thr Asn Leu Tyr Ser Leu Thr Val Pro Phe Gly Gln Lys Pro Asn Ile
                 260              265              270

Asp Val Thr Asp Ala Met Val Asp Gln Ala Trp Asp Ala Gln Arg Ile
        275              280              285

Phe Lys Glu Ala Glu Lys Phe Phe Val Ser Val Gly Leu Pro Asn Met
        290              295              300

Thr Gln Gly Phe Trp Glu Asn Ser Met Leu Thr Asp Pro Gly Asn Val
305              310              315              320

Gln Lys Ala Val Cys His Pro Thr Ala Trp Asp Leu Gly Lys Gly Asp
                 325              330              335

Phe Arg Ile Leu Met Cys Thr Lys Val Thr Met Asp Asp Phe Leu Thr
                 340              345              350

Ala His His Glu Met Gly His Ile Gln Tyr Asp Met Ala Tyr Ala Ala
        355              360              365

Gln Pro Phe Leu Leu Arg Asn Gly Ala Asn Glu Gly Phe His Glu Ala
        370              375              380

Val Gly Glu Ile Met Ser Leu Ser Ala Ala Thr Pro Lys His Leu Lys
385              390              395              400

Ser Ile Gly Leu Leu Ser Pro Asp Phe Gln Glu Asp Asn Glu Thr Glu
                 405              410              415

Ile Asn Phe Leu Leu Lys Gln Ala Leu Thr Ile Val Gly Thr Leu Pro
                 420              425              430

Phe Thr Tyr Met Leu Glu Lys Trp Arg Trp Met Val Phe Lys Gly Glu
        435              440              445

Ile Pro Lys Asp Gln Trp Met Lys Lys Trp Trp Glu Met Lys Arg Glu
        450              455              460

Ile Val Gly Val Val Glu Pro Val Pro His Asp Glu Thr Tyr Cys Asp
465              470              475              480

Pro Ala Ser Leu Phe His Val Ser Asn Asp Tyr Ser Phe Ile Arg Tyr
                 485              490              495

Tyr Thr Arg Thr Leu Tyr Gln Phe Gln Phe Gln Glu Ala Leu Cys Gln
        500              505              510

Ala Ala Lys His Glu Gly Pro Leu His Lys Cys Asp Ile Ser Asn Ser
        515              520              525

Thr Glu Ala Gly Gln Lys Leu Phe Asn Met Leu Arg Leu Gly Lys Ser
        530              535              540

Glu Pro Trp Thr Leu Ala Leu Glu Asn Val Val Gly Ala Lys Asn Met
545              550              555              560

Asn Val Arg Pro Leu Leu Asn Tyr Phe Glu Pro Leu Phe Thr Trp Leu
                 565              570              575

Lys Asp Gln Asn Lys Asn Ser Phe Val Gly Trp Ser Thr Asp Trp Ser
                 580              585              590

Pro Tyr Ala Asp
        595
```

-continued

<210> SEQ ID NO 2
<211> LENGTH: 596
<212> TYPE: PRT
<213> ORGANISM: Artificial Sequence
<220> FEATURE:
<223> OTHER INFORMATION: the sequence is synthesized

<400> SEQUENCE: 2

Thr Ile Glu Glu Gln Ala Lys Thr Phe Leu Asp Lys Phe Asn His Glu
1               5                   10                  15

Ala Glu Asp Leu Phe Tyr Gln Ser Ser Leu Ala Ser Trp Asn Tyr Asn
                20                  25                  30

Thr Asn Ile Thr Glu Glu Asn Val Gln Asn Met Asn Asn Ala Gly Asp
            35                  40                  45

Lys Trp Ser Ala Phe Leu Lys Glu Gln Ser Thr Leu Ala Gln Met Tyr
        50                  55                  60

Pro Leu Gln Glu Ile Gln Asn Leu Thr Val Lys Leu Gln Leu Gln Ala
65                  70                  75                  80

Leu Gln Gln Asn Gly Ser Ser Val Leu Ser Glu Asp Lys Ser Lys Arg
                85                  90                  95

Leu Asn Thr Ile Leu Asn Thr Met Ser Thr Ile Tyr Ser Thr Gly Lys
            100                 105                 110

Val Cys Asn Pro Asp Asn Pro Gln Glu Cys Leu Leu Leu Glu Pro Gly
            115                 120                 125

Leu Asn Glu Ile Met Ala Asn Ser Leu Asp Tyr Asn Glu Arg Leu Trp
        130                 135                 140

Ala Trp Glu Ser Trp Arg Ser Glu Val Gly Lys Gln Leu Arg Pro Leu
145                 150                 155                 160

Tyr Glu Glu Tyr Val Val Leu Lys Asn Glu Met Ala Arg Ala Asn His
                165                 170                 175

Tyr Glu Asp Tyr Gly Asp Tyr Trp Arg Gly Asp Tyr Glu Val Asn Gly
            180                 185                 190

Val Asp Gly Tyr Asp Tyr Ser Arg Gly Gln Leu Ile Glu Asp Val Glu
            195                 200                 205

His Thr Phe Glu Glu Ile Lys Pro Leu Tyr Glu His Leu His Ala Tyr
        210                 215                 220

Val Arg Ala Lys Leu Met Asn Ala Tyr Pro Ser Tyr Ile Ser Pro Ile
225                 230                 235                 240

Gly Cys Leu Pro Ala His Leu Leu Gly Asp Met Trp Gly Arg Phe Trp
                245                 250                 255

Thr Asn Leu Tyr Ser Leu Thr Val Pro Phe Gly Gln Lys Pro Asn Ile
            260                 265                 270

Asp Val Thr Asp Ala Met Val Asp Gln Ala Trp Asp Ala Gln Arg Ile
            275                 280                 285

Phe Lys Glu Ala Glu Lys Phe Phe Val Ser Val Gly Leu Pro Asn Met
        290                 295                 300

Thr Gln Gly Phe Trp Glu Asn Ser Met Leu Thr Asp Pro Gly Asn Val
305                 310                 315                 320

Gln Lys Ala Val Cys His Pro Thr Ala Trp Asp Leu Gly Lys Gly Asp
                325                 330                 335

Phe Arg Ile Leu Met Cys Thr Lys Val Thr Met Asp Asp Phe Leu Thr
            340                 345                 350

Ala His Asn Glu Met Gly Asn Ile Gln Tyr Asp Met Ala Tyr Ala Ala
            355                 360                 365

-continued

```
Gln Pro Phe Leu Leu Arg Asn Gly Ala Asn Glu Gly Phe His Glu Ala
    370             375             380

Val Gly Glu Ile Met Ser Leu Ser Ala Ala Thr Pro Lys His Leu Lys
385             390             395             400

Ser Ile Gly Leu Leu Ser Pro Asp Phe Gln Glu Asp Asn Glu Thr Glu
            405             410             415

Ile Asn Phe Leu Leu Lys Gln Ala Leu Thr Ile Val Gly Thr Leu Pro
            420             425             430

Phe Thr Tyr Met Leu Glu Lys Trp Arg Trp Met Val Phe Lys Gly Glu
            435             440             445

Ile Pro Lys Asp Gln Trp Met Lys Lys Trp Trp Glu Met Lys Arg Glu
    450             455             460

Ile Val Gly Val Val Glu Pro Val Pro His Asp Glu Thr Tyr Cys Asp
465             470             475             480

Pro Ala Ser Leu Phe His Val Ser Asn Asp Tyr Ser Phe Ile Arg Tyr
            485             490             495

Tyr Thr Arg Thr Leu Tyr Gln Phe Gln Phe Gln Glu Ala Leu Cys Gln
            500             505             510

Ala Ala Lys His Glu Gly Pro Leu His Lys Cys Asp Ile Ser Asn Ser
            515             520             525

Thr Glu Ala Gly Gln Lys Leu Phe Asn Met Leu Arg Leu Gly Lys Ser
    530             535             540

Glu Pro Trp Thr Leu Ala Leu Glu Asn Val Val Gly Ala Lys Asn Met
545             550             555             560

Asn Val Arg Pro Leu Leu Asn Tyr Phe Glu Pro Leu Phe Thr Trp Leu
            565             570             575

Lys Asp Gln Asn Lys Asn Ser Phe Val Gly Trp Ser Thr Asp Trp Ser
            580             585             590

Pro Tyr Ala Asp
        595

<210> SEQ ID NO 3
<211> LENGTH: 828
<212> TYPE: PRT
<213> ORGANISM: Artificial Sequence
<220> FEATURE:
<223> OTHER INFORMATION: the sequence is synthesized

<400> SEQUENCE: 3

Thr Ile Glu Glu Gln Ala Lys Thr Phe Leu Asp Lys Phe Asn His Glu
1               5               10              15

Ala Glu Asp Leu Phe Tyr Gln Ser Ser Leu Ala Ser Trp Asn Tyr Asn
            20              25              30

Thr Asn Ile Thr Glu Glu Asn Val Gln Asn Met Asn Asn Ala Gly Asp
            35              40              45

Lys Trp Ser Ala Phe Leu Lys Glu Gln Ser Thr Leu Ala Gln Met Tyr
    50              55              60

Pro Leu Gln Glu Ile Gln Asn Leu Thr Val Lys Leu Gln Leu Gln Ala
65              70              75              80

Leu Gln Gln Asn Gly Ser Ser Val Leu Ser Glu Asp Lys Ser Lys Arg
            85              90              95

Leu Asn Thr Ile Leu Asn Thr Met Ser Thr Ile Tyr Ser Thr Gly Lys
            100             105             110

Val Cys Asn Pro Asp Asn Pro Gln Glu Cys Leu Leu Leu Glu Pro Gly
            115             120             125
```

```
Leu Asn Glu Ile Met Ala Asn Ser Leu Asp Tyr Asn Glu Arg Leu Trp
    130                 135                 140

Ala Trp Glu Ser Trp Arg Ser Glu Val Gly Lys Gln Leu Arg Pro Leu
145                 150                 155                 160

Tyr Glu Glu Tyr Val Val Leu Lys Asn Glu Met Ala Arg Ala Asn His
                165                 170                 175

Tyr Glu Asp Tyr Gly Asp Tyr Trp Arg Gly Asp Tyr Glu Val Asn Gly
            180                 185                 190

Val Asp Gly Tyr Asp Tyr Ser Arg Gly Gln Leu Ile Glu Asp Val Glu
        195                 200                 205

His Thr Phe Glu Glu Ile Lys Pro Leu Tyr Glu His Leu His Ala Tyr
    210                 215                 220

Val Arg Ala Lys Leu Met Asn Ala Tyr Pro Ser Tyr Ile Ser Pro Ile
225                 230                 235                 240

Gly Cys Leu Pro Ala His Leu Leu Gly Asp Met Trp Gly Arg Phe Trp
                245                 250                 255

Thr Asn Leu Tyr Ser Leu Thr Val Pro Phe Gly Gln Lys Pro Asn Ile
                260                 265                 270

Asp Val Thr Asp Ala Met Val Asp Gln Ala Trp Asp Ala Gln Arg Ile
            275                 280                 285

Phe Lys Glu Ala Glu Lys Phe Phe Val Ser Val Gly Leu Pro Asn Met
    290                 295                 300

Thr Gln Gly Phe Trp Glu Asn Ser Met Leu Thr Asp Pro Gly Asn Val
305                 310                 315                 320

Gln Lys Ala Val Cys His Pro Thr Ala Trp Asp Leu Gly Lys Gly Asp
                325                 330                 335

Phe Arg Ile Leu Met Cys Thr Lys Val Thr Met Asp Asp Phe Leu Thr
                340                 345                 350

Ala His His Glu Met Gly His Ile Gln Tyr Asp Met Ala Tyr Ala Ala
            355                 360                 365

Gln Pro Phe Leu Leu Arg Asn Gly Ala Asn Glu Gly Phe His Glu Ala
    370                 375                 380

Val Gly Glu Ile Met Ser Leu Ser Ala Ala Thr Pro Lys His Leu Lys
385                 390                 395                 400

Ser Ile Gly Leu Leu Ser Pro Asp Phe Gln Glu Asp Asn Glu Thr Glu
                405                 410                 415

Ile Asn Phe Leu Leu Lys Gln Ala Leu Thr Ile Val Gly Thr Leu Pro
                420                 425                 430

Phe Thr Tyr Met Leu Glu Lys Trp Arg Trp Met Val Phe Lys Gly Glu
        435                 440                 445

Ile Pro Lys Asp Gln Trp Met Lys Lys Trp Trp Glu Met Lys Arg Glu
    450                 455                 460

Ile Val Gly Val Val Glu Pro Val Pro His Asp Glu Thr Tyr Cys Asp
465                 470                 475                 480

Pro Ala Ser Leu Phe His Val Ser Asn Asp Tyr Ser Phe Ile Arg Tyr
                485                 490                 495

Tyr Thr Arg Thr Leu Tyr Gln Phe Gln Phe Gln Glu Ala Leu Cys Gln
            500                 505                 510

Ala Ala Lys His Glu Gly Pro Leu His Lys Cys Asp Ile Ser Asn Ser
        515                 520                 525

Thr Glu Ala Gly Gln Lys Leu Phe Asn Met Leu Arg Leu Gly Lys Ser
    530                 535                 540
```

```
Glu Pro Trp Thr Leu Ala Leu Glu Asn Val Val Gly Ala Lys Asn Met
545                 550                 555                 560

Asn Val Arg Pro Leu Leu Asn Tyr Phe Glu Pro Leu Phe Thr Trp Leu
                565                 570                 575

Lys Asp Gln Asn Lys Asn Ser Phe Val Gly Trp Ser Thr Asp Trp Ser
                580                 585                 590

Pro Tyr Ala Asp Glu Pro Lys Ser Ser Asp Lys Thr His Thr Cys Pro
                595                 600                 605

Pro Cys Pro Ala Pro Glu Leu Leu Gly Gly Pro Ser Val Phe Leu Phe
                610                 615                 620

Pro Pro Lys Pro Lys Asp Thr Leu Met Ile Ser Arg Thr Pro Glu Val
625                 630                 635                 640

Thr Cys Val Val Val Asp Val Ser His Glu Asp Pro Glu Val Lys Phe
                645                 650                 655

Asn Trp Tyr Val Asp Gly Val Glu Val His Asn Ala Lys Thr Lys Pro
                660                 665                 670

Arg Glu Glu Gln Tyr Asn Ser Thr Tyr Arg Val Val Ser Val Leu Thr
                675                 680                 685

Val Leu His Gln Asp Trp Leu Asn Gly Lys Glu Tyr Lys Cys Lys Val
                690                 695                 700

Ser Asn Lys Ala Leu Pro Ala Pro Ile Glu Lys Thr Ile Ser Lys Ala
705                 710                 715                 720

Lys Gly Gln Pro Arg Glu Pro Gln Val Tyr Thr Leu Pro Pro Ser Arg
                725                 730                 735

Asp Glu Leu Thr Lys Asn Gln Val Ser Leu Thr Cys Leu Val Lys Gly
                740                 745                 750

Phe Tyr Pro Ser Asp Ile Ala Val Glu Trp Glu Ser Asn Gly Gln Pro
                755                 760                 765

Glu Asn Asn Tyr Lys Thr Thr Pro Pro Val Leu Asp Ser Asp Gly Ser
                770                 775                 780

Phe Phe Leu Tyr Ser Lys Leu Thr Val Asp Lys Ser Arg Trp Gln Gln
785                 790                 795                 800

Gly Asn Val Phe Ser Cys Ser Val Met His Glu Ala Leu His Asn His
                805                 810                 815

Tyr Thr Gln Lys Ser Leu Ser Leu Ser Pro Gly Lys
                820                 825
```

```
<210> SEQ ID NO 4
<211> LENGTH: 828
<212> TYPE: PRT
<213> ORGANISM: Artificial Sequence
<220> FEATURE:
<223> OTHER INFORMATION: the sequence is synthesized

<400> SEQUENCE: 4

Thr Ile Glu Glu Gln Ala Lys Thr Phe Leu Asp Lys Phe Asn His Glu
1                   5                   10                  15

Ala Glu Asp Leu Phe Tyr Gln Ser Ser Leu Ala Ser Trp Asn Tyr Asn
                20                  25                  30

Thr Asn Ile Thr Glu Glu Asn Val Gln Asn Met Asn Asn Ala Gly Asp
        35                  40                  45

Lys Trp Ser Ala Phe Leu Lys Glu Gln Ser Thr Leu Ala Gln Met Tyr
        50                  55                  60

Pro Leu Gln Glu Ile Gln Asn Leu Thr Val Lys Leu Gln Leu Gln Ala
65                  70                  75                  80
```

-continued

```
Leu Gln Gln Asn Gly Ser Ser Val Leu Ser Glu Asp Lys Ser Lys Arg
             85                  90                  95

Leu Asn Thr Ile Leu Asn Thr Met Ser Thr Ile Tyr Ser Thr Gly Lys
            100                 105                 110

Val Cys Asn Pro Asp Asn Pro Gln Glu Cys Leu Leu Leu Glu Pro Gly
            115                 120                 125

Leu Asn Glu Ile Met Ala Asn Ser Leu Asp Tyr Asn Glu Arg Leu Trp
130                 135                 140

Ala Trp Glu Ser Trp Arg Ser Glu Val Gly Lys Gln Leu Arg Pro Leu
145                 150                 155                 160

Tyr Glu Glu Tyr Val Val Leu Lys Asn Glu Met Ala Arg Ala Asn His
                165                 170                 175

Tyr Glu Asp Tyr Gly Asp Tyr Trp Arg Gly Asp Tyr Glu Val Asn Gly
            180                 185                 190

Val Asp Gly Tyr Asp Tyr Ser Arg Gly Gln Leu Ile Glu Asp Val Glu
            195                 200                 205

His Thr Phe Glu Glu Ile Lys Pro Leu Tyr Glu His Leu His Ala Tyr
            210                 215                 220

Val Arg Ala Lys Leu Met Asn Ala Tyr Pro Ser Tyr Ile Ser Pro Ile
225                 230                 235                 240

Gly Cys Leu Pro Ala His Leu Leu Gly Asp Met Trp Gly Arg Phe Trp
            245                 250                 255

Thr Asn Leu Tyr Ser Leu Thr Val Pro Phe Gly Gln Lys Pro Asn Ile
            260                 265                 270

Asp Val Thr Asp Ala Met Val Asp Gln Ala Trp Asp Ala Gln Arg Ile
            275                 280                 285

Phe Lys Glu Ala Glu Lys Phe Phe Val Ser Val Gly Leu Pro Asn Met
            290                 295                 300

Thr Gln Gly Phe Trp Glu Asn Ser Met Leu Thr Asp Pro Gly Asn Val
305                 310                 315                 320

Gln Lys Ala Val Cys His Pro Thr Ala Trp Asp Leu Gly Lys Gly Asp
            325                 330                 335

Phe Arg Ile Leu Met Cys Thr Lys Val Thr Met Asp Asp Phe Leu Thr
            340                 345                 350

Ala His Asn Glu Met Gly Asn Ile Gln Tyr Asp Met Ala Tyr Ala Ala
            355                 360                 365

Gln Pro Phe Leu Leu Arg Asn Gly Ala Asn Glu Gly Phe His Glu Ala
            370                 375                 380

Val Gly Glu Ile Met Ser Leu Ser Ala Ala Thr Pro Lys His Leu Lys
385                 390                 395                 400

Ser Ile Gly Leu Leu Ser Pro Asp Phe Gln Glu Asp Asn Glu Thr Glu
            405                 410                 415

Ile Asn Phe Leu Leu Lys Gln Ala Leu Thr Ile Val Gly Thr Leu Pro
            420                 425                 430

Phe Thr Tyr Met Leu Glu Lys Trp Arg Trp Met Val Phe Lys Gly Glu
            435                 440                 445

Ile Pro Lys Asp Gln Trp Met Lys Lys Trp Trp Glu Met Lys Arg Glu
            450                 455                 460

Ile Val Gly Val Val Glu Pro Val Pro His Asp Glu Thr Tyr Cys Asp
465                 470                 475                 480

Pro Ala Ser Leu Phe His Val Ser Asn Asp Tyr Ser Phe Ile Arg Tyr
            485                 490                 495

Tyr Thr Arg Thr Leu Tyr Gln Phe Gln Phe Gln Glu Ala Leu Cys Gln
```

-continued

```
                500                 505                 510

Ala Ala Lys His Glu Gly Pro Leu His Lys Cys Asp Ile Ser Asn Ser
        515                 520                 525

Thr Glu Ala Gly Gln Lys Leu Phe Asn Met Leu Arg Leu Gly Lys Ser
        530                 535                 540

Glu Pro Trp Thr Leu Ala Leu Glu Asn Val Val Gly Ala Lys Asn Met
545                 550                 555                 560

Asn Val Arg Pro Leu Leu Asn Tyr Phe Glu Pro Leu Phe Thr Trp Leu
                565                 570                 575

Lys Asp Gln Asn Lys Asn Ser Phe Val Gly Trp Ser Thr Asp Trp Ser
                580                 585                 590

Pro Tyr Ala Asp Glu Pro Lys Ser Ser Asp Lys Thr His Thr Cys Pro
                595                 600                 605

Pro Cys Pro Ala Pro Glu Leu Leu Gly Gly Pro Ser Val Phe Leu Phe
                610                 615                 620

Pro Pro Lys Pro Lys Asp Thr Leu Met Ile Ser Arg Thr Pro Glu Val
625                 630                 635                 640

Thr Cys Val Val Val Asp Val Ser His Glu Asp Pro Glu Val Lys Phe
                645                 650                 655

Asn Trp Tyr Val Asp Gly Val Glu Val His Asn Ala Lys Thr Lys Pro
                660                 665                 670

Arg Glu Glu Gln Tyr Asn Ser Thr Tyr Arg Val Val Ser Val Leu Thr
                675                 680                 685

Val Leu His Gln Asp Trp Leu Asn Gly Lys Glu Tyr Lys Cys Lys Val
        690                 695                 700

Ser Asn Lys Ala Leu Pro Ala Pro Ile Glu Lys Thr Ile Ser Lys Ala
705                 710                 715                 720

Lys Gly Gln Pro Arg Glu Pro Gln Val Tyr Thr Leu Pro Pro Ser Arg
                725                 730                 735

Asp Glu Leu Thr Lys Asn Gln Val Ser Leu Thr Cys Leu Val Lys Gly
                740                 745                 750

Phe Tyr Pro Ser Asp Ile Ala Val Glu Trp Glu Ser Asn Gly Gln Pro
                755                 760                 765

Glu Asn Asn Tyr Lys Thr Thr Pro Pro Val Leu Asp Ser Asp Gly Ser
        770                 775                 780

Phe Phe Leu Tyr Ser Lys Leu Thr Val Asp Lys Ser Arg Trp Gln Gln
785                 790                 795                 800

Gly Asn Val Phe Ser Cys Ser Val Met His Glu Ala Leu His Asn His
                805                 810                 815

Tyr Thr Gln Lys Ser Leu Ser Leu Ser Pro Gly Lys
                820                 825

<210> SEQ ID NO 5
<211> LENGTH: 844
<212> TYPE: PRT
<213> ORGANISM: Artificial Sequence
<220> FEATURE:
<223> OTHER INFORMATION: the sequence is synthesized

<400> SEQUENCE: 5

Met Pro Leu Leu Leu Leu Leu Pro Leu Leu Trp Ala Gly Ala Leu Ala
1                   5                   10                  15

Thr Ile Glu Glu Gln Ala Lys Thr Phe Leu Asp Lys Phe Asn His Glu
            20                  25                  30

Ala Glu Asp Leu Phe Tyr Gln Ser Ser Leu Ala Ser Trp Asn Tyr Asn
```

-continued

```
            35                  40                  45
Thr Asn Ile Thr Glu Glu Asn Val Gln Asn Met Asn Asn Ala Gly Asp
    50                  55                  60

Lys Trp Ser Ala Phe Leu Lys Glu Gln Ser Thr Leu Ala Gln Met Tyr
65                  70                  75                  80

Pro Leu Gln Glu Ile Gln Asn Leu Thr Val Lys Leu Gln Leu Gln Ala
                85                  90                  95

Leu Gln Gln Asn Gly Ser Ser Val Leu Ser Glu Asp Lys Ser Lys Arg
            100                 105                 110

Leu Asn Thr Ile Leu Asn Thr Met Ser Thr Ile Tyr Ser Thr Gly Lys
            115                 120                 125

Val Cys Asn Pro Asp Asn Pro Gln Glu Cys Leu Leu Leu Glu Pro Gly
    130                 135                 140

Leu Asn Glu Ile Met Ala Asn Ser Leu Asp Tyr Asn Glu Arg Leu Trp
145                 150                 155                 160

Ala Trp Glu Ser Trp Arg Ser Glu Val Gly Lys Gln Leu Arg Pro Leu
                165                 170                 175

Tyr Glu Glu Tyr Val Val Leu Lys Asn Glu Met Ala Arg Ala Asn His
            180                 185                 190

Tyr Glu Asp Tyr Gly Asp Tyr Trp Arg Gly Asp Tyr Glu Val Asn Gly
            195                 200                 205

Val Asp Gly Tyr Asp Tyr Ser Arg Gly Gln Leu Ile Glu Asp Val Glu
    210                 215                 220

His Thr Phe Glu Glu Ile Lys Pro Leu Tyr Glu His Leu His Ala Tyr
225                 230                 235                 240

Val Arg Ala Lys Leu Met Asn Ala Tyr Pro Ser Tyr Ile Ser Pro Ile
                245                 250                 255

Gly Cys Leu Pro Ala His Leu Leu Gly Asp Met Trp Gly Arg Phe Trp
            260                 265                 270

Thr Asn Leu Tyr Ser Leu Thr Val Pro Phe Gly Gln Lys Pro Asn Ile
            275                 280                 285

Asp Val Thr Asp Ala Met Val Asp Gln Ala Trp Asp Ala Gln Arg Ile
    290                 295                 300

Phe Lys Glu Ala Glu Lys Phe Phe Val Ser Val Gly Leu Pro Asn Met
305                 310                 315                 320

Thr Gln Gly Phe Trp Glu Asn Ser Met Leu Thr Asp Pro Gly Asn Val
                325                 330                 335

Gln Lys Ala Val Cys His Pro Thr Ala Trp Asp Leu Gly Lys Gly Asp
            340                 345                 350

Phe Arg Ile Leu Met Cys Thr Lys Val Thr Met Asp Asp Phe Leu Thr
            355                 360                 365

Ala His His Glu Met Gly His Ile Gln Tyr Asp Met Ala Tyr Ala Ala
    370                 375                 380

Gln Pro Phe Leu Leu Arg Asn Gly Ala Asn Glu Gly Phe His Glu Ala
385                 390                 395                 400

Val Gly Glu Ile Met Ser Leu Ser Ala Ala Thr Pro Lys His Leu Lys
                405                 410                 415

Ser Ile Gly Leu Leu Ser Pro Asp Phe Gln Glu Asp Asn Glu Thr Glu
            420                 425                 430

Ile Asn Phe Leu Leu Lys Gln Ala Leu Thr Ile Val Gly Thr Leu Pro
            435                 440                 445

Phe Thr Tyr Met Leu Glu Lys Trp Arg Trp Met Val Phe Lys Gly Glu
    450                 455                 460
```

-continued

```
Ile Pro Lys Asp Gln Trp Met Lys Lys Trp Trp Glu Met Lys Arg Glu
465                 470                 475                 480

Ile Val Gly Val Val Glu Pro Val Pro His Asp Glu Thr Tyr Cys Asp
                    485                 490                 495

Pro Ala Ser Leu Phe His Val Ser Asn Asp Tyr Ser Phe Ile Arg Tyr
                500                 505                 510

Tyr Thr Arg Thr Leu Tyr Gln Phe Gln Phe Gln Glu Ala Leu Cys Gln
            515                 520                 525

Ala Ala Lys His Glu Gly Pro Leu His Lys Cys Asp Ile Ser Asn Ser
        530                 535                 540

Thr Glu Ala Gly Gln Lys Leu Phe Asn Met Leu Arg Leu Gly Lys Ser
545                 550                 555                 560

Glu Pro Trp Thr Leu Ala Leu Glu Asn Val Val Gly Ala Lys Asn Met
                565                 570                 575

Asn Val Arg Pro Leu Leu Asn Tyr Phe Glu Pro Leu Phe Thr Trp Leu
                580                 585                 590

Lys Asp Gln Asn Lys Asn Ser Phe Val Gly Trp Ser Thr Asp Trp Ser
            595                 600                 605

Pro Tyr Ala Asp Glu Pro Lys Ser Ser Asp Lys Thr His Thr Cys Pro
        610                 615                 620

Pro Cys Pro Ala Pro Glu Leu Leu Gly Gly Pro Ser Val Phe Leu Phe
625                 630                 635                 640

Pro Pro Lys Pro Lys Asp Thr Leu Met Ile Ser Arg Thr Pro Glu Val
                645                 650                 655

Thr Cys Val Val Val Asp Val Ser His Glu Asp Pro Glu Val Lys Phe
                660                 665                 670

Asn Trp Tyr Val Asp Gly Val Glu Val His Asn Ala Lys Thr Lys Pro
            675                 680                 685

Arg Glu Glu Gln Tyr Asn Ser Thr Tyr Arg Val Val Ser Val Leu Thr
        690                 695                 700

Val Leu His Gln Asp Trp Leu Asn Gly Lys Glu Tyr Lys Cys Lys Val
705                 710                 715                 720

Ser Asn Lys Ala Leu Pro Ala Pro Ile Glu Lys Thr Ile Ser Lys Ala
                725                 730                 735

Lys Gly Gln Pro Arg Glu Pro Gln Val Tyr Thr Leu Pro Pro Ser Arg
                740                 745                 750

Asp Glu Leu Thr Lys Asn Gln Val Ser Leu Thr Cys Leu Val Lys Gly
            755                 760                 765

Phe Tyr Pro Ser Asp Ile Ala Val Glu Trp Glu Ser Asn Gly Gln Pro
        770                 775                 780

Glu Asn Asn Tyr Lys Thr Thr Pro Pro Val Leu Asp Ser Asp Gly Ser
785                 790                 795                 800

Phe Phe Leu Tyr Ser Lys Leu Thr Val Asp Lys Ser Arg Trp Gln Gln
                805                 810                 815

Gly Asn Val Phe Ser Cys Ser Val Met His Glu Ala Leu His Asn His
                820                 825                 830

Tyr Thr Gln Lys Ser Leu Ser Leu Ser Pro Gly Lys
            835                 840
```

```
<210> SEQ ID NO 6
<211> LENGTH: 844
<212> TYPE: PRT
<213> ORGANISM: Artificial Sequence
<220> FEATURE:
```

<223> OTHER INFORMATION: the sequence is synthesized

<400> SEQUENCE: 6

```
Met Pro Leu Leu Leu Leu Leu Pro Leu Leu Trp Ala Gly Ala Leu Ala
1               5                   10                  15

Thr Ile Glu Glu Gln Ala Lys Thr Phe Leu Asp Lys Phe Asn His Glu
            20                  25                  30

Ala Glu Asp Leu Phe Tyr Gln Ser Ser Leu Ala Ser Trp Asn Tyr Asn
            35                  40                  45

Thr Asn Ile Thr Glu Glu Asn Val Gln Asn Met Asn Asn Ala Gly Asp
        50                  55                  60

Lys Trp Ser Ala Phe Leu Lys Glu Gln Ser Thr Leu Ala Gln Met Tyr
65                  70                  75                  80

Pro Leu Gln Glu Ile Gln Asn Leu Thr Val Lys Leu Gln Leu Gln Ala
                85                  90                  95

Leu Gln Gln Asn Gly Ser Ser Val Leu Ser Glu Asp Lys Ser Lys Arg
            100                 105                 110

Leu Asn Thr Ile Leu Asn Thr Met Ser Thr Ile Tyr Ser Thr Gly Lys
        115                 120                 125

Val Cys Asn Pro Asp Asn Pro Gln Glu Cys Leu Leu Leu Glu Pro Gly
        130                 135                 140

Leu Asn Glu Ile Met Ala Asn Ser Leu Asp Tyr Asn Glu Arg Leu Trp
145                 150                 155                 160

Ala Trp Glu Ser Trp Arg Ser Glu Val Gly Lys Gln Leu Arg Pro Leu
                165                 170                 175

Tyr Glu Glu Tyr Val Val Leu Lys Asn Glu Met Ala Arg Ala Asn His
            180                 185                 190

Tyr Glu Asp Tyr Gly Asp Tyr Trp Arg Gly Asp Tyr Glu Val Asn Gly
            195                 200                 205

Val Asp Gly Tyr Asp Tyr Ser Arg Gly Gln Leu Ile Glu Asp Val Glu
        210                 215                 220

His Thr Phe Glu Glu Ile Lys Pro Leu Tyr Glu His Leu His Ala Tyr
225                 230                 235                 240

Val Arg Ala Lys Leu Met Asn Ala Tyr Pro Ser Tyr Ile Ser Pro Ile
                245                 250                 255

Gly Cys Leu Pro Ala His Leu Leu Gly Asp Met Trp Gly Arg Phe Trp
            260                 265                 270

Thr Asn Leu Tyr Ser Leu Thr Val Pro Phe Gly Gln Lys Pro Asn Ile
        275                 280                 285

Asp Val Thr Asp Ala Met Val Asp Gln Ala Trp Asp Ala Gln Arg Ile
        290                 295                 300

Phe Lys Glu Ala Glu Lys Phe Phe Val Ser Val Gly Leu Pro Asn Met
305                 310                 315                 320

Thr Gln Gly Phe Trp Glu Asn Ser Met Leu Thr Asp Pro Gly Asn Val
            325                 330                 335

Gln Lys Ala Val Cys His Pro Thr Ala Trp Asp Leu Gly Lys Gly Asp
            340                 345                 350

Phe Arg Ile Leu Met Cys Thr Lys Val Thr Met Asp Asp Phe Leu Thr
            355                 360                 365

Ala His Asn Glu Met Gly Asn Ile Gln Tyr Asp Met Ala Tyr Ala Ala
        370                 375                 380

Gln Pro Phe Leu Leu Arg Asn Gly Ala Asn Glu Gly Phe His Glu Ala
385                 390                 395                 400
```

```
Val Gly Glu Ile Met Ser Leu Ser Ala Ala Thr Pro Lys His Leu Lys
            405                 410                 415

Ser Ile Gly Leu Leu Ser Pro Asp Phe Gln Glu Asp Asn Glu Thr Glu
            420                 425                 430

Ile Asn Phe Leu Leu Lys Gln Ala Leu Thr Ile Val Gly Thr Leu Pro
            435                 440                 445

Phe Thr Tyr Met Leu Glu Lys Trp Arg Trp Met Val Phe Lys Gly Glu
    450                 455                 460

Ile Pro Lys Asp Gln Trp Met Lys Lys Trp Trp Glu Met Lys Arg Glu
465                 470                 475                 480

Ile Val Gly Val Val Glu Pro Val Pro His Asp Glu Thr Tyr Cys Asp
                485                 490                 495

Pro Ala Ser Leu Phe His Val Ser Asn Asp Tyr Ser Phe Ile Arg Tyr
            500                 505                 510

Tyr Thr Arg Thr Leu Tyr Gln Phe Gln Phe Gln Glu Ala Leu Cys Gln
            515                 520                 525

Ala Ala Lys His Glu Gly Pro Leu His Lys Cys Asp Ile Ser Asn Ser
            530                 535                 540

Thr Glu Ala Gly Gln Lys Leu Phe Asn Met Leu Arg Leu Gly Lys Ser
545                 550                 555                 560

Glu Pro Trp Thr Leu Ala Leu Glu Asn Val Val Gly Ala Lys Asn Met
            565                 570                 575

Asn Val Arg Pro Leu Leu Asn Tyr Phe Glu Pro Leu Phe Thr Trp Leu
            580                 585                 590

Lys Asp Gln Asn Lys Asn Ser Phe Val Gly Trp Ser Thr Asp Trp Ser
            595                 600                 605

Pro Tyr Ala Asp Glu Pro Lys Ser Ser Asp Lys Thr His Thr Cys Pro
    610                 615                 620

Pro Cys Pro Ala Pro Glu Leu Leu Gly Gly Pro Ser Val Phe Leu Phe
625                 630                 635                 640

Pro Pro Lys Pro Lys Asp Thr Leu Met Ile Ser Arg Thr Pro Glu Val
            645                 650                 655

Thr Cys Val Val Val Asp Val Ser His Glu Asp Pro Glu Val Lys Phe
            660                 665                 670

Asn Trp Tyr Val Asp Gly Val Glu Val His Asn Ala Lys Thr Lys Pro
            675                 680                 685

Arg Glu Glu Gln Tyr Asn Ser Thr Tyr Arg Val Val Ser Val Leu Thr
    690                 695                 700

Val Leu His Gln Asp Trp Leu Asn Gly Lys Glu Tyr Lys Cys Lys Val
705                 710                 715                 720

Ser Asn Lys Ala Leu Pro Ala Pro Ile Glu Lys Thr Ile Ser Lys Ala
            725                 730                 735

Lys Gly Gln Pro Arg Glu Pro Gln Val Tyr Thr Leu Pro Pro Ser Arg
            740                 745                 750

Asp Glu Leu Thr Lys Asn Gln Val Ser Leu Thr Cys Leu Val Lys Gly
            755                 760                 765

Phe Tyr Pro Ser Asp Ile Ala Val Glu Trp Glu Ser Asn Gly Gln Pro
    770                 775                 780

Glu Asn Asn Tyr Lys Thr Thr Pro Pro Val Leu Asp Ser Asp Gly Ser
785                 790                 795                 800

Phe Phe Leu Tyr Ser Lys Leu Thr Val Asp Lys Ser Arg Trp Gln Gln
            805                 810                 815

Gly Asn Val Phe Ser Cys Ser Val Met His Glu Ala Leu His Asn His
```

```
                820                 825                 830
Tyr Thr Gln Lys Ser Leu Ser Leu Ser Pro Gly Lys
        835                 840

<210> SEQ ID NO 7
<211> LENGTH: 862
<212> TYPE: PRT
<213> ORGANISM: Artificial Sequence
<220> FEATURE:
<223> OTHER INFORMATION: the sequence is synthesized

<400> SEQUENCE: 7

Met Pro Leu Leu Leu Leu Leu Pro Leu Leu Trp Ala Gly Ala Leu Ala
1               5                   10                  15

Thr Ile Glu Glu Gln Ala Lys Thr Phe Leu Asp Lys Phe Asn His Glu
            20                  25                  30

Ala Glu Asp Leu Phe Tyr Gln Ser Ser Leu Ala Ser Trp Asn Tyr Asn
        35                  40                  45

Thr Asn Ile Thr Glu Glu Asn Val Gln Asn Met Asn Asn Ala Gly Asp
    50                  55                  60

Lys Trp Ser Ala Phe Leu Lys Glu Gln Ser Thr Leu Ala Gln Met Tyr
65                  70                  75                  80

Pro Leu Gln Glu Ile Gln Asn Leu Thr Val Lys Leu Gln Leu Gln Ala
                85                  90                  95

Leu Gln Gln Asn Gly Ser Ser Val Leu Ser Glu Asp Lys Ser Lys Arg
            100                 105                 110

Leu Asn Thr Ile Leu Asn Thr Met Ser Thr Ile Tyr Ser Thr Gly Lys
        115                 120                 125

Val Cys Asn Pro Asp Asn Pro Gln Glu Cys Leu Leu Leu Glu Pro Gly
    130                 135                 140

Leu Asn Glu Ile Met Ala Asn Ser Leu Asp Tyr Asn Glu Arg Leu Trp
145                 150                 155                 160

Ala Trp Glu Ser Trp Arg Ser Glu Val Gly Lys Gln Leu Arg Pro Leu
                165                 170                 175

Tyr Glu Glu Tyr Val Val Leu Lys Asn Glu Met Ala Arg Ala Asn His
            180                 185                 190

Tyr Glu Asp Tyr Gly Asp Tyr Trp Arg Gly Asp Tyr Glu Val Asn Gly
        195                 200                 205

Val Asp Gly Tyr Asp Tyr Ser Arg Gly Gln Leu Ile Glu Asp Val Glu
    210                 215                 220

His Thr Phe Glu Glu Ile Lys Pro Leu Tyr Glu His Leu His Ala Tyr
225                 230                 235                 240

Val Arg Ala Lys Leu Met Asn Ala Tyr Pro Ser Tyr Ile Ser Pro Ile
                245                 250                 255

Gly Cys Leu Pro Ala His Leu Leu Gly Asp Met Trp Gly Arg Phe Trp
            260                 265                 270

Thr Asn Leu Tyr Ser Leu Thr Val Pro Phe Gly Gln Lys Pro Asn Ile
        275                 280                 285

Asp Val Thr Asp Ala Met Val Asp Gln Ala Trp Asp Ala Gln Arg Ile
    290                 295                 300

Phe Lys Glu Ala Glu Lys Phe Phe Val Ser Val Gly Leu Pro Asn Met
305                 310                 315                 320

Thr Gln Gly Phe Trp Glu Asn Ser Met Leu Thr Asp Pro Gly Asn Val
                325                 330                 335

Gln Lys Ala Val Cys His Pro Thr Ala Trp Asp Leu Gly Lys Gly Asp
```

-continued

```
            340              345              350
Phe Arg Ile Leu Met Cys Thr Lys Val Thr Met Asp Asp Phe Leu Thr
        355              360              365

Ala His His Glu Met Gly His Ile Gln Tyr Asp Met Ala Tyr Ala Ala
    370              375              380

Gln Pro Phe Leu Leu Arg Asn Gly Ala Asn Glu Gly Phe His Glu Ala
385              390              395              400

Val Gly Glu Ile Met Ser Leu Ser Ala Ala Thr Pro Lys His Leu Lys
            405              410              415

Ser Ile Gly Leu Leu Ser Pro Asp Phe Gln Glu Asp Asn Glu Thr Glu
            420              425              430

Ile Asn Phe Leu Leu Lys Gln Ala Leu Thr Ile Val Gly Thr Leu Pro
        435              440              445

Phe Thr Tyr Met Leu Glu Lys Trp Arg Trp Met Val Phe Lys Gly Glu
        450              455              460

Ile Pro Lys Asp Gln Trp Met Lys Lys Trp Trp Glu Met Lys Arg Glu
465              470              475              480

Ile Val Gly Val Val Glu Pro Val Pro His Asp Glu Thr Tyr Cys Asp
            485              490              495

Pro Ala Ser Leu Phe His Val Ser Asn Asp Tyr Ser Phe Ile Arg Tyr
            500              505              510

Tyr Thr Arg Thr Leu Tyr Gln Phe Gln Phe Gln Glu Ala Leu Cys Gln
        515              520              525

Ala Ala Lys His Glu Gly Pro Leu His Lys Cys Asp Ile Ser Asn Ser
        530              535              540

Thr Glu Ala Gly Gln Lys Leu Phe Asn Met Leu Arg Leu Gly Lys Ser
545              550              555              560

Glu Pro Trp Thr Leu Ala Leu Glu Asn Val Val Gly Ala Lys Asn Met
            565              570              575

Asn Val Arg Pro Leu Leu Asn Tyr Phe Glu Pro Leu Phe Thr Trp Leu
            580              585              590

Lys Asp Gln Asn Lys Asn Ser Phe Val Gly Trp Ser Thr Asp Trp Ser
        595              600              605

Pro Tyr Ala Asp Glu Pro Lys Ser Ser Asp Lys Thr His Thr Cys Pro
    610              615              620

Pro Cys Pro Ala Pro Glu Leu Leu Gly Gly Pro Ser Val Phe Leu Phe
625              630              635              640

Pro Pro Lys Pro Lys Asp Thr Leu Met Ile Ser Arg Thr Pro Glu Val
            645              650              655

Thr Cys Val Val Val Asp Val Ser His Glu Asp Pro Glu Val Lys Phe
            660              665              670

Asn Trp Tyr Val Asp Gly Val Glu Val His Asn Ala Lys Thr Lys Pro
        675              680              685

Arg Glu Glu Gln Tyr Asn Ser Thr Tyr Arg Val Val Ser Val Leu Thr
        690              695              700

Val Leu His Gln Asp Trp Leu Asn Gly Lys Glu Tyr Lys Cys Lys Val
705              710              715              720

Ser Asn Lys Ala Leu Pro Ala Pro Ile Glu Lys Thr Ile Ser Lys Ala
            725              730              735

Lys Gly Gln Pro Arg Glu Pro Gln Val Tyr Thr Leu Pro Pro Ser Arg
            740              745              750

Asp Glu Leu Thr Lys Asn Gln Val Ser Leu Thr Cys Leu Val Lys Gly
            755              760              765
```

```
Phe Tyr Pro Ser Asp Ile Ala Val Glu Trp Glu Ser Asn Gly Gln Pro
    770             775             780
```

```
Glu Asn Asn Tyr Lys Thr Thr Pro Pro Val Leu Asp Ser Asp Gly Ser
785             790             795             800
```

```
Phe Phe Leu Tyr Ser Lys Leu Thr Val Asp Lys Ser Arg Trp Gln Gln
            805             810             815
```

```
Gly Asn Val Phe Ser Cys Ser Val Met His Glu Ala Leu His Asn His
            820             825             830
```

```
Tyr Thr Gln Lys Ser Leu Ser Leu Ser Thr Gly Lys Pro Thr Leu Tyr
        835             840             845
```

```
Asn Val Ser Leu Val Met Ser Asp Thr Ala Gly Thr Cys Tyr
    850             855             860
```

<210> SEQ ID NO 8
<211> LENGTH: 862
<212> TYPE: PRT
<213> ORGANISM: Artificial Sequence
<220> FEATURE:
<223> OTHER INFORMATION: the sequence is synthesized

<400> SEQUENCE: 8

```
Met Pro Leu Leu Leu Leu Leu Pro Leu Leu Trp Ala Gly Ala Leu Ala
1               5               10              15
```

```
Thr Ile Glu Glu Gln Ala Lys Thr Phe Leu Asp Lys Phe Asn His Glu
            20              25              30
```

```
Ala Glu Asp Leu Phe Tyr Gln Ser Ser Leu Ala Ser Trp Asn Tyr Asn
        35              40              45
```

```
Thr Asn Ile Thr Glu Glu Asn Val Gln Asn Met Asn Asn Ala Gly Asp
    50              55              60
```

```
Lys Trp Ser Ala Phe Leu Lys Glu Gln Ser Thr Leu Ala Gln Met Tyr
65              70              75              80
```

```
Pro Leu Gln Glu Ile Gln Asn Leu Thr Val Lys Leu Gln Leu Gln Ala
            85              90              95
```

```
Leu Gln Gln Asn Gly Ser Ser Val Leu Ser Glu Asp Lys Ser Lys Arg
            100             105             110
```

```
Leu Asn Thr Ile Leu Asn Thr Met Ser Thr Ile Tyr Ser Thr Gly Lys
            115             120             125
```

```
Val Cys Asn Pro Asp Asn Pro Gln Glu Cys Leu Leu Leu Glu Pro Gly
    130             135             140
```

```
Leu Asn Glu Ile Met Ala Asn Ser Leu Asp Tyr Asn Glu Arg Leu Trp
145             150             155             160
```

```
Ala Trp Glu Ser Trp Arg Ser Glu Val Gly Lys Gln Leu Arg Pro Leu
            165             170             175
```

```
Tyr Glu Glu Tyr Val Val Leu Lys Asn Glu Met Ala Arg Ala Asn His
            180             185             190
```

```
Tyr Glu Asp Tyr Gly Asp Tyr Trp Arg Gly Asp Tyr Glu Val Asn Gly
            195             200             205
```

```
Val Asp Gly Tyr Asp Tyr Ser Arg Gly Gln Leu Ile Glu Asp Val Glu
    210             215             220
```

```
His Thr Phe Glu Glu Ile Lys Pro Leu Tyr Glu His Leu His Ala Tyr
225             230             235             240
```

```
Val Arg Ala Lys Leu Met Asn Ala Tyr Pro Ser Tyr Ile Ser Pro Ile
            245             250             255
```

```
Gly Cys Leu Pro Ala His Leu Leu Gly Asp Met Trp Gly Arg Phe Trp
            260             265             270
```

```
Thr Asn Leu Tyr Ser Leu Thr Val Pro Phe Gly Gln Lys Pro Asn Ile
    275                 280                 285

Asp Val Thr Asp Ala Met Val Asp Gln Ala Trp Asp Ala Gln Arg Ile
    290                 295                 300

Phe Lys Glu Ala Glu Lys Phe Phe Val Ser Val Gly Leu Pro Asn Met
305                 310                 315                 320

Thr Gln Gly Phe Trp Glu Asn Ser Met Leu Thr Asp Pro Gly Asn Val
                325                 330                 335

Gln Lys Ala Val Cys His Pro Thr Ala Trp Asp Leu Gly Lys Gly Asp
            340                 345                 350

Phe Arg Ile Leu Met Cys Thr Lys Val Thr Met Asp Asp Phe Leu Thr
        355                 360                 365

Ala His Asn Glu Met Gly Asn Ile Gln Tyr Asp Met Ala Tyr Ala Ala
    370                 375                 380

Gln Pro Phe Leu Leu Arg Asn Gly Ala Asn Glu Gly Phe His Glu Ala
385                 390                 395                 400

Val Gly Glu Ile Met Ser Leu Ser Ala Ala Thr Pro Lys His Leu Lys
                405                 410                 415

Ser Ile Gly Leu Leu Ser Pro Asp Phe Gln Glu Asp Asn Glu Thr Glu
            420                 425                 430

Ile Asn Phe Leu Leu Lys Gln Ala Leu Thr Ile Val Gly Thr Leu Pro
        435                 440                 445

Phe Thr Tyr Met Leu Glu Lys Trp Arg Trp Met Val Phe Lys Gly Glu
    450                 455                 460

Ile Pro Lys Asp Gln Trp Met Lys Lys Trp Trp Glu Met Lys Arg Glu
465                 470                 475                 480

Ile Val Gly Val Val Glu Pro Val Pro His Asp Glu Thr Tyr Cys Asp
                485                 490                 495

Pro Ala Ser Leu Phe His Val Ser Asn Asp Tyr Ser Phe Ile Arg Tyr
            500                 505                 510

Tyr Thr Arg Thr Leu Tyr Gln Phe Gln Phe Gln Glu Ala Leu Cys Gln
        515                 520                 525

Ala Ala Lys His Glu Gly Pro Leu His Lys Cys Asp Ile Ser Asn Ser
    530                 535                 540

Thr Glu Ala Gly Gln Lys Leu Phe Asn Met Leu Arg Leu Gly Lys Ser
545                 550                 555                 560

Glu Pro Trp Thr Leu Ala Leu Glu Asn Val Val Gly Ala Lys Asn Met
                565                 570                 575

Asn Val Arg Pro Leu Leu Asn Tyr Phe Glu Pro Leu Phe Thr Trp Leu
            580                 585                 590

Lys Asp Gln Asn Lys Asn Ser Phe Val Gly Trp Ser Thr Asp Trp Ser
        595                 600                 605

Pro Tyr Ala Asp Glu Pro Lys Ser Ser Asp Lys Thr His Thr Cys Pro
    610                 615                 620

Pro Cys Pro Ala Pro Glu Leu Leu Gly Gly Pro Ser Val Phe Leu Phe
625                 630                 635                 640

Pro Pro Lys Pro Lys Asp Thr Leu Met Ile Ser Arg Thr Pro Glu Val
                645                 650                 655

Thr Cys Val Val Val Asp Val Ser His Glu Asp Pro Glu Val Lys Phe
            660                 665                 670

Asn Trp Tyr Val Asp Gly Val Glu Val His Asn Ala Lys Thr Lys Pro
        675                 680                 685
```

-continued

```
Arg Glu Glu Gln Tyr Asn Ser Thr Tyr Arg Val Val Ser Val Leu Thr
    690                 695                 700

Val Leu His Gln Asp Trp Leu Asn Gly Lys Glu Tyr Lys Cys Lys Val
705                 710                 715                 720

Ser Asn Lys Ala Leu Pro Ala Pro Ile Glu Lys Thr Ile Ser Lys Ala
                725                 730                 735

Lys Gly Gln Pro Arg Glu Pro Gln Val Tyr Thr Leu Pro Pro Ser Arg
                740                 745                 750

Asp Glu Leu Thr Lys Asn Gln Val Ser Leu Thr Cys Leu Val Lys Gly
            755                 760                 765

Phe Tyr Pro Ser Asp Ile Ala Val Glu Trp Glu Ser Asn Gly Gln Pro
    770                 775                 780

Glu Asn Asn Tyr Lys Thr Thr Pro Pro Val Leu Asp Ser Asp Gly Ser
785                 790                 795                 800

Phe Phe Leu Tyr Ser Lys Leu Thr Val Asp Lys Ser Arg Trp Gln Gln
                805                 810                 815

Gly Asn Val Phe Ser Cys Ser Val Met His Glu Ala Leu His Asn His
                820                 825                 830

Tyr Thr Gln Lys Ser Leu Ser Leu Ser Thr Gly Lys Pro Thr Leu Tyr
            835                 840                 845

Asn Val Ser Leu Val Met Ser Asp Thr Ala Gly Thr Cys Tyr
    850                 855                 860

<210> SEQ ID NO 9
<211> LENGTH: 1273
<212> TYPE: PRT
<213> ORGANISM: Coaxana purpurea

<400> SEQUENCE: 9

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
            115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
            195                 200                 205
```

```
Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
                260                 265                 270

Arg Thr Phe Leu Leu Lys Tyr Asn Glu Asn Gly Thr Ile Thr Asp Ala
                275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
                340                 345                 350

Trp Asn Arg Lys Arg Ile Ser Asn Cys Val Ala Asp Tyr Ser Val Leu
                355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
                435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
                515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
    610                 615                 620
```

-continued

```
His Ala Asp Gln Leu Thr Pro Thr Trp Arg Val Tyr Ser Thr Gly Ser
625             630             635             640

Asn Val Phe Gln Thr Arg Ala Gly Cys Leu Ile Gly Ala Glu His Val
            645             650             655

Asn Asn Ser Tyr Glu Cys Asp Ile Pro Ile Gly Ala Gly Ile Cys Ala
            660             665             670

Ser Tyr Gln Thr Gln Thr Asn Ser Pro Arg Arg Ala Arg Ser Val Ala
            675             680             685

Ser Gln Ser Ile Ile Ala Tyr Thr Met Ser Leu Gly Ala Glu Asn Ser
            690             695             700

Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
            725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
            755             760             765

Gly Ile Ala Val Glu Gln Asp Lys Asn Thr Gln Glu Val Phe Ala Gln
            770             775             780

Val Lys Gln Ile Tyr Lys Thr Pro Pro Ile Lys Asp Phe Gly Gly Phe
785             790             795             800

Asn Phe Ser Gln Ile Leu Pro Asp Pro Ser Lys Pro Ser Lys Arg Ser
            805             810             815

Phe Ile Glu Asp Leu Leu Phe Asn Lys Val Thr Leu Ala Asp Ala Gly
            820             825             830

Phe Ile Lys Gln Tyr Gly Asp Cys Leu Gly Asp Ile Ala Ala Arg Asp
            835             840             845

Leu Ile Cys Ala Gln Lys Phe Asn Gly Leu Thr Val Leu Pro Pro Leu
            850             855             860

Leu Thr Asp Glu Met Ile Ala Gln Tyr Thr Ser Ala Leu Leu Ala Gly
865             870             875             880

Thr Ile Thr Ser Gly Trp Thr Phe Gly Ala Gly Ala Ala Leu Gln Ile
            885             890             895

Pro Phe Ala Met Gln Met Ala Tyr Arg Phe Asn Gly Ile Gly Val Thr
            900             905             910

Gln Asn Val Leu Tyr Glu Asn Gln Lys Leu Ile Ala Asn Gln Phe Asn
            915             920             925

Ser Ala Ile Gly Lys Ile Gln Asp Ser Leu Ser Ser Thr Ala Ser Ala
            930             935             940

Leu Gly Lys Leu Gln Asp Val Val Asn Gln Asn Ala Gln Ala Leu Asn
945             950             955             960

Thr Leu Val Lys Gln Leu Ser Ser Asn Phe Gly Ala Ile Ser Ser Val
            965             970             975

Leu Asn Asp Ile Leu Ser Arg Leu Asp Lys Val Glu Ala Glu Val Gln
            980             985             990

Ile Asp Arg Leu Ile Thr Gly Arg  Leu Gln Ser Leu Gln  Thr Tyr Val
            995             1000            1005

Thr Gln  Gln Leu Ile Arg Ala  Ala Glu Ile Arg Ala  Ser Ala Asn Leu
    1010            1015            1020

Ala  Ala Thr Lys Met Ser  Glu Cys Val Leu Gly  Gln Ser Lys Arg Val
1025            1030            1035            1040

Asp Phe Cys Gly Lys  Gly Tyr His Leu Met  Ser Phe Pro Gln Ser  Ala
```

```
                     1045              1050              1055

Pro His Gly Val  Val Phe Leu His Val  Thr Tyr Val Pro Ala  Gln Glu
             1060              1065              1070

Lys Asn Phe  Thr Thr Ala Pro Ala  Ile Cys His Asp Gly  Lys Ala His
         1075              1080              1085

Phe Pro  Arg Glu Gly Val Phe  Val Ser Asn Gly Thr  His Trp Phe Val
         1090              1095              1100

Thr  Gln Arg Asn Phe Tyr  Glu Pro Gln Ile Ile  Thr Thr Asp Asn Thr
1105              1110              1115              1120

Phe Val Ser Gly Asn  Cys Asp Val Val Ile  Gly Ile Val Asn Asn  Thr
             1125              1130              1135

Val Tyr Asp Pro  Leu Gln Pro Glu Leu  Asp Ser Phe Lys Glu  Glu Leu
         1140              1145              1150

Asp Lys Tyr  Phe Lys Asn His Thr  Ser Pro Asp Val Asp  Leu Gly Asp
         1155              1160              1165

Ile Ser  Gly Ile Asn Ala Ser  Val Val Asn Ile Gln  Lys Glu Ile Asp
         1170              1175              1180

Arg  Leu Asn Glu Val Ala  Lys Asn Leu Asn Glu  Ser Leu Ile Asp Leu
1185              1190              1195              1200

Gln Glu Leu Gly Lys  Tyr Glu Gln Tyr Ile  Lys Trp Pro Trp Tyr  Ile
             1205              1210              1215

Trp Leu Gly Phe  Ile Ala Gly Leu Ile  Ala Ile Val Met Val  Thr Ile
             1220              1225              1230

Met Leu Cys  Cys Met Thr Ser Cys  Cys Ser Cys Leu Lys  Gly Cys Cys
         1235              1240              1245

Ser Cys  Gly Ser Cys Cys Lys  Phe Asp Glu Asp Asp  Ser Glu Pro Val
         1250              1255              1260

Leu  Lys Gly Val Lys Leu  His Tyr Thr
1265              1270
```

<210> SEQ ID NO 10
<211> LENGTH: 1273
<212> TYPE: PRT
<213> ORGANISM: Artificial Sequence
<220> FEATURE:
<223> OTHER INFORMATION: the sequence is synthesized

<400> SEQUENCE: 10

```
Met Phe Val Phe Leu Val Leu Leu Pro Leu Val Ser Ser Gln Cys Val
1               5                  10                 15

Asn Leu Thr Thr Arg Thr Gln Leu Pro Pro Ala Tyr Thr Asn Ser Phe
            20                 25                 30

Thr Arg Gly Val Tyr Tyr Pro Asp Lys Val Phe Arg Ser Ser Val Leu
        35                 40                 45

His Ser Thr Gln Asp Leu Phe Leu Pro Phe Phe Ser Asn Val Thr Trp
    50                 55                 60

Phe His Ala Ile His Val Ser Gly Thr Asn Gly Thr Lys Arg Phe Asp
65                 70                 75                 80

Asn Pro Val Leu Pro Phe Asn Asp Gly Val Tyr Phe Ala Ser Thr Glu
            85                 90                 95

Lys Ser Asn Ile Ile Arg Gly Trp Ile Phe Gly Thr Thr Leu Asp Ser
            100                105                110

Lys Thr Gln Ser Leu Leu Ile Val Asn Asn Ala Thr Asn Val Val Ile
        115                120                125

Lys Val Cys Glu Phe Gln Phe Cys Asn Asp Pro Phe Leu Gly Val Tyr
```

-continued

```
              130                 135                 140
Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
                180                 185                 190

Val Phe Lys Asn Ile Asp Gly Tyr Phe Lys Ile Tyr Ser Lys His Thr
                195                 200                 205

Pro Ile Asn Leu Val Arg Asp Leu Pro Gln Gly Phe Ser Ala Leu Glu
        210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
                260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
        290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
                340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
        370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
        450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
                515                 520                 525

Lys Ser Thr Asn Leu Val Lys Asn Lys Cys Val Asn Phe Asn Phe Asn
        530                 535                 540

Gly Leu Thr Gly Thr Gly Val Leu Thr Glu Ser Asn Lys Lys Phe Leu
545                 550                 555                 560
```

```
Pro Phe Gln Gln Phe Gly Arg Asp Ile Ala Asp Thr Thr Asp Ala Val
            565             570             575

Arg Asp Pro Gln Thr Leu Glu Ile Leu Asp Ile Thr Pro Cys Ser Phe
            580             585             590

Gly Gly Val Ser Val Ile Thr Pro Gly Thr Asn Thr Ser Asn Gln Val
            595             600             605

Ala Val Leu Tyr Gln Asp Val Asn Cys Thr Glu Val Pro Val Ala Ile
        610             615             620

His Ala Asp Gln Leu Thr Pro Thr Trp Arg Val Tyr Ser Thr Gly Ser
625             630             635             640

Asn Val Phe Gln Thr Arg Ala Gly Cys Leu Ile Gly Ala Glu His Val
            645             650             655

Asn Asn Ser Tyr Glu Cys Asp Ile Pro Ile Gly Ala Gly Ile Cys Ala
            660             665             670

Ser Tyr Gln Thr Gln Thr Asn Ser Pro Ser Arg Ala Ser Ser Val Ala
            675             680             685

Ser Gln Ser Ile Ile Ala Tyr Thr Met Ser Leu Gly Ala Glu Asn Ser
        690             695             700

Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
            725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
            755             760             765

Gly Ile Ala Val Glu Gln Asp Lys Asn Thr Gln Glu Val Phe Ala Gln
        770             775             780

Val Lys Gln Ile Tyr Lys Thr Pro Pro Ile Lys Asp Phe Gly Gly Phe
785             790             795             800

Asn Phe Ser Gln Ile Leu Pro Asp Pro Ser Lys Pro Ser Lys Arg Ser
            805             810             815

Phe Ile Glu Asp Leu Leu Phe Asn Lys Val Thr Leu Ala Asp Ala Gly
            820             825             830

Phe Ile Lys Gln Tyr Gly Asp Cys Leu Gly Asp Ile Ala Ala Arg Asp
            835             840             845

Leu Ile Cys Ala Gln Lys Phe Asn Gly Leu Thr Val Leu Pro Pro Leu
        850             855             860

Leu Thr Asp Glu Met Ile Ala Gln Tyr Thr Ser Ala Leu Leu Ala Gly
865             870             875             880

Thr Ile Thr Ser Gly Trp Thr Phe Gly Ala Gly Ala Ala Leu Gln Ile
            885             890             895

Pro Phe Ala Met Gln Met Ala Tyr Arg Phe Asn Gly Ile Gly Val Thr
            900             905             910

Gln Asn Val Leu Tyr Glu Asn Gln Lys Leu Ile Ala Asn Gln Phe Asn
            915             920             925

Ser Ala Ile Gly Lys Ile Gln Asp Ser Leu Ser Ser Thr Ala Ser Ala
        930             935             940

Leu Gly Lys Leu Gln Asp Val Val Asn Gln Asn Ala Gln Ala Leu Asn
945             950             955             960

Thr Leu Val Lys Gln Leu Ser Ser Asn Phe Gly Ala Ile Ser Ser Val
            965             970             975
```

```
Leu Asn Asp Ile Leu Ser Arg Leu Asp Lys Val Glu Ala Glu Val Gln
            980             985             990

Ile Asp Arg Leu Ile Thr Gly Arg  Leu Gln Ser Leu Gln  Thr Tyr Val
        995             1000            1005

Thr Gln  Gln Leu Ile Arg Ala  Ala Glu Ile Arg Ala  Ser Ala Asn Leu
    1010            1015            1020

Ala  Ala Thr Lys Met Ser  Glu Cys Val Leu Gly  Gln Ser Lys Arg Val
1025            1030            1035            1040

Asp Phe Cys Gly Lys  Gly Tyr His Leu Met  Ser Phe Pro Gln Ser  Ala
            1045            1050            1055

Pro His Gly Val  Val Phe Leu His Val  Thr Tyr Val Pro Ala  Gln Glu
            1060            1065            1070

Lys Asn Phe  Thr Thr Ala Pro Ala  Ile Cys His Asp Gly  Lys Ala His
    1075            1080            1085

Phe Pro  Arg Glu Gly Val Phe  Val Ser Asn Gly Thr  His Trp Phe Val
    1090            1095            1100

Thr  Gln Arg Asn Phe Tyr  Glu Pro Gln Ile Ile  Thr Thr Asp Asn Thr
1105            1110            1115            1120

Phe Val Ser Gly Asn  Cys Asp Val Val Ile  Gly Ile Val Asn Asn  Thr
            1125            1130            1135

Val Tyr Asp Pro  Leu Gln Pro Glu Leu  Asp Ser Phe Lys Glu  Glu Leu
        1140            1145            1150

Asp Lys Tyr  Phe Lys Asn His Thr  Ser Pro Asp Val Asp  Leu Gly Asp
    1155            1160            1165

Ile Ser  Gly Ile Asn Ala Ser  Val Val Asn Ile Gln  Lys Glu Ile Asp
    1170            1175            1180

Arg  Leu Asn Glu Val Ala  Lys Asn Leu Asn Glu  Ser Leu Ile Asp Leu
1185            1190            1195            1200

Gln Glu Leu Gly Lys  Tyr Glu Gln Tyr Ile  Lys Trp Pro Trp Tyr  Ile
            1205            1210            1215

Trp Leu Gly Phe  Ile Ala Gly Leu Ile  Ala Ile Val Met Val  Thr Ile
            1220            1225            1230

Met Leu Cys  Cys Met Thr Ser Cys  Cys Ser Cys Leu Lys  Gly Cys Cys
    1235            1240            1245

Ser Cys  Gly Ser Cys Cys Lys  Phe Asp Glu Asp Asp  Ser Glu Pro Val
    1250            1255            1260

Leu  Lys Gly Val Lys Leu  His Tyr Thr
1265            1270
```

<210> SEQ ID NO 11
<211> LENGTH: 1208
<212> TYPE: PRT
<213> ORGANISM: Artificial Sequence
<220> FEATURE:
<223> OTHER INFORMATION: the sequence is synthesized

<400> SEQUENCE: 11

```
Met Phe Val Phe Leu Val Leu Leu Pro Leu Val Ser Ser Gln Cys Val
1               5               10              15

Asn Leu Thr Thr Arg Thr Gln Leu Pro Pro Ala Tyr Thr Asn Ser Phe
            20              25              30

Thr Arg Gly Val Tyr Tyr Pro Asp Lys Val Phe Arg Ser Ser Val Leu
        35              40              45

His Ser Thr Gln Asp Leu Phe Leu Pro Phe Phe Ser Asn Val Thr Trp
    50              55              60
```

-continued

```
Phe His Ala Ile His Val Ser Gly Thr Asn Gly Thr Lys Arg Phe Asp
65              70              75              80

Asn Pro Val Leu Pro Phe Asn Asp Gly Val Tyr Phe Ala Ser Thr Glu
                85              90              95

Lys Ser Asn Ile Ile Arg Gly Trp Ile Phe Gly Thr Thr Leu Asp Ser
            100             105             110

Lys Thr Gln Ser Leu Leu Ile Val Asn Asn Ala Thr Asn Val Val Ile
        115             120             125

Lys Val Cys Glu Phe Gln Phe Cys Asn Asp Pro Phe Leu Gly Val Tyr
    130             135             140

Tyr His Lys Asn Asn Lys Ser Trp Met Glu Ser Glu Phe Arg Val Tyr
145             150             155             160

Ser Ser Ala Asn Asn Cys Thr Phe Glu Tyr Val Ser Gln Pro Phe Leu
            165             170             175

Met Asp Leu Glu Gly Lys Gln Gly Asn Phe Lys Asn Leu Arg Glu Phe
        180             185             190

Val Phe Lys Asn Ile Asp Gly Tyr Phe Lys Ile Tyr Ser Lys His Thr
    195             200             205

Pro Ile Asn Leu Val Arg Asp Leu Pro Gln Gly Phe Ser Ala Leu Glu
    210             215             220

Pro Leu Val Asp Leu Pro Ile Gly Ile Asn Ile Thr Arg Phe Gln Thr
225             230             235             240

Leu Leu Ala Leu His Arg Ser Tyr Leu Thr Pro Gly Asp Ser Ser Ser
            245             250             255

Gly Trp Thr Ala Gly Ala Ala Ala Tyr Tyr Val Gly Tyr Leu Gln Pro
        260             265             270

Arg Thr Phe Leu Leu Lys Tyr Asn Glu Asn Gly Thr Ile Thr Asp Ala
        275             280             285

Val Asp Cys Ala Leu Asp Pro Leu Ser Glu Thr Lys Cys Thr Leu Lys
    290             295             300

Ser Phe Thr Val Glu Lys Gly Ile Tyr Gln Thr Ser Asn Phe Arg Val
305             310             315             320

Gln Pro Thr Glu Ser Ile Val Arg Phe Pro Asn Ile Thr Asn Leu Cys
            325             330             335

Pro Phe Gly Glu Val Phe Asn Ala Thr Arg Phe Ala Ser Val Tyr Ala
        340             345             350

Trp Asn Arg Lys Arg Ile Ser Asn Cys Val Ala Asp Tyr Ser Val Leu
        355             360             365

Tyr Asn Ser Ala Ser Phe Ser Thr Phe Lys Cys Tyr Gly Val Ser Pro
    370             375             380

Thr Lys Leu Asn Asp Leu Cys Phe Thr Asn Val Tyr Ala Asp Ser Phe
385             390             395             400

Val Ile Arg Gly Asp Glu Val Arg Gln Ile Ala Pro Gly Gln Thr Gly
            405             410             415

Lys Ile Ala Asp Tyr Asn Tyr Lys Leu Pro Asp Asp Phe Thr Gly Cys
        420             425             430

Val Ile Ala Trp Asn Ser Asn Asn Leu Asp Ser Lys Val Gly Gly Asn
        435             440             445

Tyr Asn Tyr Leu Tyr Arg Leu Phe Arg Lys Ser Asn Leu Lys Pro Phe
    450             455             460

Glu Arg Asp Ile Ser Thr Glu Ile Tyr Gln Ala Gly Ser Thr Pro Cys
465             470             475             480

Asn Gly Val Glu Gly Phe Asn Cys Tyr Phe Pro Leu Gln Ser Tyr Gly
```

-continued

```
                        485                 490                 495
Phe Gln Pro Thr Asn Gly Val Gly Tyr Gln Pro Tyr Arg Val Val Val
            500                 505                 510
Leu Ser Phe Glu Leu Leu His Ala Pro Ala Thr Val Cys Gly Pro Lys
            515                 520                 525
Lys Ser Thr Asn Leu Val Lys Asn Lys Cys Val Asn Phe Asn Phe Asn
            530                 535                 540
Gly Leu Thr Gly Thr Gly Val Leu Thr Glu Ser Asn Lys Lys Phe Leu
545                 550                 555                 560
Pro Phe Gln Gln Phe Gly Arg Asp Ile Ala Asp Thr Thr Asp Ala Val
            565                 570                 575
Arg Asp Pro Gln Thr Leu Glu Ile Leu Asp Ile Thr Pro Cys Ser Phe
            580                 585                 590
Gly Gly Val Ser Val Ile Thr Pro Gly Thr Asn Thr Ser Asn Gln Val
            595                 600                 605
Ala Val Leu Tyr Gln Asp Val Asn Cys Thr Glu Val Pro Val Ala Ile
            610                 615                 620
His Ala Asp Gln Leu Thr Pro Thr Trp Arg Val Tyr Ser Thr Gly Ser
625                 630                 635                 640
Asn Val Phe Gln Thr Arg Ala Gly Cys Leu Ile Gly Ala Glu His Val
            645                 650                 655
Asn Asn Ser Tyr Glu Cys Asp Ile Pro Ile Gly Ala Gly Ile Cys Ala
            660                 665                 670
Ser Tyr Gln Thr Gln Thr Asn Ser Pro Arg Arg Ala Arg Ser Val Ala
            675                 680                 685
Ser Gln Ser Ile Ile Ala Tyr Thr Met Ser Leu Gly Ala Glu Asn Ser
            690                 695                 700
Val Ala Tyr Ser Asn Asn Ser Ile Ala Ile Pro Thr Asn Phe Thr Ile
705                 710                 715                 720
Ser Val Thr Thr Glu Ile Leu Pro Val Ser Met Thr Lys Thr Ser Val
            725                 730                 735
Asp Cys Thr Met Tyr Ile Cys Gly Asp Ser Thr Glu Cys Ser Asn Leu
            740                 745                 750
Leu Leu Gln Tyr Gly Ser Phe Cys Thr Gln Leu Asn Arg Ala Leu Thr
            755                 760                 765
Gly Ile Ala Val Glu Gln Asp Lys Asn Thr Gln Glu Val Phe Ala Gln
            770                 775                 780
Val Lys Gln Ile Tyr Lys Thr Pro Pro Ile Lys Asp Phe Gly Gly Phe
785                 790                 795                 800
Asn Phe Ser Gln Ile Leu Pro Asp Pro Ser Lys Pro Ser Lys Arg Ser
            805                 810                 815
Phe Ile Glu Asp Leu Leu Phe Asn Lys Val Thr Leu Ala Asp Ala Gly
            820                 825                 830
Phe Ile Lys Gln Tyr Gly Asp Cys Leu Gly Asp Ile Ala Ala Arg Asp
            835                 840                 845
Leu Ile Cys Ala Gln Lys Phe Asn Gly Leu Thr Val Leu Pro Pro Leu
            850                 855                 860
Leu Thr Asp Glu Met Ile Ala Gln Tyr Thr Ser Ala Leu Leu Ala Gly
865                 870                 875                 880
Thr Ile Thr Ser Gly Trp Thr Phe Gly Ala Gly Ala Ala Leu Gln Ile
            885                 890                 895
Pro Phe Ala Met Gln Met Ala Tyr Arg Phe Asn Gly Ile Gly Val Thr
            900                 905                 910
```

-continued

```
Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
        930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg Leu Gln Ser Leu Gln Thr Tyr Val
                995                 1000                1005

Thr Gln Gln Leu Ile Arg Ala Ala Glu Ile Arg Ala Ser Ala Asn Leu
    1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055

Pro His Gly Val Val Phe Leu His Val Thr Tyr Val Pro Ala Gln Glu
                1060                1065                1070

Lys Asn Phe Thr Thr Ala Pro Ala Ile Cys His Asp Gly Lys Ala His
                1075                1080                1085

Phe Pro Arg Glu Gly Val Phe Val Ser Asn Gly Thr His Trp Phe Val
    1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
                1125                1130                1135

Val Tyr Asp Pro Leu Gln Pro Glu Leu Asp Ser Phe Lys Glu Glu Leu
                1140                1145                1150

Asp Lys Tyr Phe Lys Asn His Thr Ser Pro Asp Val Asp Leu Gly Asp
                1155                1160                1165

Ile Ser Gly Ile Asn Ala Ser Val Val Asn Ile Gln Lys Glu Ile Asp
    1170                1175                1180

Arg Leu Asn Glu Val Ala Lys Asn Leu Asn Glu Ser Leu Ile Asp Leu
1185                1190                1195                1200

Gln Glu Leu Gly Lys Tyr Glu Gln
                1205
```

```
<210> SEQ ID NO 12
<211> LENGTH: 1208
<212> TYPE: PRT
<213> ORGANISM: Artificial Sequence
<220> FEATURE:
<223> OTHER INFORMATION: the sequence is synthesized

<400> SEQUENCE: 12
```

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
                20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60
```

```
Phe His Ala Ile His Val Ser Gly Thr Asn Gly Thr Lys Arg Phe Asp
65                  70              75                  80

Asn Pro Val Leu Pro Phe Asn Asp Gly Val Tyr Phe Ala Ser Thr Glu
                85              90                  95

Lys Ser Asn Ile Ile Arg Gly Trp Ile Phe Gly Thr Thr Leu Asp Ser
            100             105             110

Lys Thr Gln Ser Leu Leu Ile Val Asn Asn Ala Thr Asn Val Val Ile
            115             120             125

Lys Val Cys Glu Phe Gln Phe Cys Asn Asp Pro Phe Leu Gly Val Tyr
        130             135             140

Tyr His Lys Asn Asn Lys Ser Trp Met Glu Ser Glu Phe Arg Val Tyr
145             150             155             160

Ser Ser Ala Asn Asn Cys Thr Phe Glu Tyr Val Ser Gln Pro Phe Leu
            165             170             175

Met Asp Leu Glu Gly Lys Gln Gly Asn Phe Lys Asn Leu Arg Glu Phe
            180             185             190

Val Phe Lys Asn Ile Asp Gly Tyr Phe Lys Ile Tyr Ser Lys His Thr
        195             200             205

Pro Ile Asn Leu Val Arg Asp Leu Pro Gln Gly Phe Ser Ala Leu Glu
        210             215             220

Pro Leu Val Asp Leu Pro Ile Gly Ile Asn Ile Thr Arg Phe Gln Thr
225             230             235             240

Leu Leu Ala Leu His Arg Ser Tyr Leu Thr Pro Gly Asp Ser Ser Ser
            245             250             255

Gly Trp Thr Ala Gly Ala Ala Ala Tyr Tyr Val Gly Tyr Leu Gln Pro
            260             265             270

Arg Thr Phe Leu Leu Lys Tyr Asn Glu Asn Gly Thr Ile Thr Asp Ala
        275             280             285

Val Asp Cys Ala Leu Asp Pro Leu Ser Glu Thr Lys Cys Thr Leu Lys
        290             295             300

Ser Phe Thr Val Glu Lys Gly Ile Tyr Gln Thr Ser Asn Phe Arg Val
305             310             315             320

Gln Pro Thr Glu Ser Ile Val Arg Phe Pro Asn Ile Thr Asn Leu Cys
            325             330             335

Pro Phe Gly Glu Val Phe Asn Ala Thr Arg Phe Ala Ser Val Tyr Ala
            340             345             350

Trp Asn Arg Lys Arg Ile Ser Asn Cys Val Ala Asp Tyr Ser Val Leu
        355             360             365

Tyr Asn Ser Ala Ser Phe Ser Thr Phe Lys Cys Tyr Gly Val Ser Pro
    370             375             380

Thr Lys Leu Asn Asp Leu Cys Phe Thr Asn Val Tyr Ala Asp Ser Phe
385             390             395             400

Val Ile Arg Gly Asp Glu Val Arg Gln Ile Ala Pro Gly Gln Thr Gly
            405             410             415

Lys Ile Ala Asp Tyr Asn Tyr Lys Leu Pro Asp Asp Phe Thr Gly Cys
            420             425             430

Val Ile Ala Trp Asn Ser Asn Asn Leu Asp Ser Lys Val Gly Gly Asn
        435             440             445

Tyr Asn Tyr Leu Tyr Arg Leu Phe Arg Lys Ser Asn Leu Lys Pro Phe
    450             455             460

Glu Arg Asp Ile Ser Thr Glu Ile Tyr Gln Ala Gly Ser Thr Pro Cys
465             470             475             480
```

-continued

```
Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Ser Arg Ala Ser Ser Val Ala
            675                 680                 685

Ser Gln Ser Ile Ile Ala Tyr Thr Met Ser Leu Gly Ala Glu Asn Ser
            690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
```

-continued

```
          900              905              910
Gln Asn Val Leu Tyr Glu Asn Gln Lys Leu Ile Ala Asn Gln Phe Asn
     915                  920              925

Ser Ala Ile Gly Lys Ile Gln Asp Ser Leu Ser Ser Thr Ala Ser Ala
     930                  935              940

Leu Gly Lys Leu Gln Asp Val Val Asn Gln Asn Ala Gln Ala Leu Asn
945                  950              955              960

Thr Leu Val Lys Gln Leu Ser Ser Asn Phe Gly Ala Ile Ser Ser Val
               965              970              975

Leu Asn Asp Ile Leu Ser Arg Leu Asp Lys Val Glu Ala Glu Val Gln
               980              985              990

Ile Asp Arg Leu Ile Thr Gly Arg  Leu Gln Ser Leu Gln  Thr Tyr Val
               995              1000              1005

Thr Gln  Gln Leu Ile Arg Ala  Ala Glu Ile Arg Ala  Ser Ala Asn Leu
     1010              1015              1020

Ala  Ala Thr Lys Met Ser  Glu Cys Val Leu Gly  Gln Ser Lys Arg Val
1025              1030              1035              1040

Asp Phe Cys Gly Lys  Gly Tyr His Leu Met  Ser Phe Pro Gln Ser  Ala
               1045              1050              1055

Pro His Gly Val  Val Phe Leu His Val  Thr Tyr Val Pro Ala  Gln Glu
               1060              1065              1070

Lys Asn Phe  Thr Thr Ala Pro Ala  Ile Cys His Asp Gly  Lys Ala His
               1075              1080              1085

Phe Pro  Arg Glu Gly Val Phe  Val Ser Asn Gly Thr  His Trp Phe Val
               1090              1095              1100

Thr  Gln Arg Asn Phe Tyr  Glu Pro Gln Ile Ile  Thr Thr Asp Asn Thr
1105              1110              1115              1120

Phe Val Ser Gly Asn  Cys Asp Val Val Ile  Gly Ile Val Asn Asn  Thr
               1125              1130              1135

Val Tyr Asp Pro  Leu Gln Pro Glu Leu  Asp Ser Phe Lys Glu  Glu Leu
               1140              1145              1150

Asp Lys Tyr  Phe Lys Asn His Thr  Ser Pro Asp Val Asp  Leu Gly Asp
               1155              1160              1165

Ile Ser  Gly Ile Asn Ala Ser  Val Val Asn Ile Gln  Lys Glu Ile Asp
               1170              1175              1180

Arg  Leu Asn Glu Val Ala  Lys Asn Leu Asn Glu  Ser Leu Ile Asp Leu
1185              1190              1195              1200

Gln Glu Leu Gly Lys  Tyr Glu Gln
               1205
```

```
<210> SEQ ID NO 13
<211> LENGTH: 1443
<212> TYPE: PRT
<213> ORGANISM: Artificial Sequence
<220> FEATURE:
<223> OTHER INFORMATION: the sequence is synthesized

<400> SEQUENCE: 13

Met Pro Leu Leu Leu Leu Leu Pro Leu Leu Trp Ala Gly Ala Leu Ala
1               5              10              15

Thr Ile Glu Glu Gln Ala Lys Thr Phe Leu Asp Lys Phe Asn His Glu
               20              25              30

Ala Glu Asp Leu Phe Tyr Gln Ser Ser Leu Ala Ser Trp Asn Tyr Asn
     35              40              45

Thr Asn Ile Thr Glu Glu Asn Val Gln Asn Met Asn Asn Ala Gly Asp
```

-continued

```
            50                  55                  60

Lys Trp Ser Ala Phe Leu Lys Glu Gln Ser Thr Leu Ala Gln Met Tyr
65                  70                  75                  80

Pro Leu Gln Glu Ile Gln Asn Leu Thr Val Lys Leu Gln Leu Gln Ala
                85                  90                  95

Leu Gln Gln Asn Gly Ser Ser Val Leu Ser Glu Asp Lys Ser Lys Arg
                100                 105                 110

Leu Asn Thr Ile Leu Asn Thr Met Ser Thr Ile Tyr Ser Thr Gly Lys
                115                 120                 125

Val Cys Asn Pro Asp Asn Pro Gln Glu Cys Leu Leu Leu Glu Pro Gly
                130                 135                 140

Leu Asn Glu Ile Met Ala Asn Ser Leu Asp Tyr Asn Glu Arg Leu Trp
145                 150                 155                 160

Ala Trp Glu Ser Trp Arg Ser Glu Val Gly Lys Gln Leu Arg Pro Leu
                165                 170                 175

Tyr Glu Glu Tyr Val Val Leu Lys Asn Glu Met Ala Arg Ala Asn His
                180                 185                 190

Tyr Glu Asp Tyr Gly Asp Tyr Trp Arg Gly Asp Tyr Glu Val Asn Gly
                195                 200                 205

Val Asp Gly Tyr Asp Tyr Ser Arg Gly Gln Leu Ile Glu Asp Val Glu
                210                 215                 220

His Thr Phe Glu Glu Ile Lys Pro Leu Tyr Glu His Leu His Ala Tyr
225                 230                 235                 240

Val Arg Ala Lys Leu Met Asn Ala Tyr Pro Ser Tyr Ile Ser Pro Ile
                245                 250                 255

Gly Cys Leu Pro Ala His Leu Leu Gly Asp Met Trp Gly Arg Phe Trp
                260                 265                 270

Thr Asn Leu Tyr Ser Leu Thr Val Pro Phe Gly Gln Lys Pro Asn Ile
                275                 280                 285

Asp Val Thr Asp Ala Met Val Asp Gln Ala Trp Asp Ala Gln Arg Ile
                290                 295                 300

Phe Lys Glu Ala Glu Lys Phe Phe Val Ser Val Gly Leu Pro Asn Met
305                 310                 315                 320

Thr Gln Gly Phe Trp Glu Asn Ser Met Leu Thr Asp Pro Gly Asn Val
                325                 330                 335

Gln Lys Ala Val Cys His Pro Thr Ala Trp Asp Leu Gly Lys Gly Asp
                340                 345                 350

Phe Arg Ile Leu Met Cys Thr Lys Val Thr Met Asp Asp Phe Leu Thr
                355                 360                 365

Ala His Asn Glu Met Gly Asn Ile Gln Tyr Asp Met Ala Tyr Ala Ala
                370                 375                 380

Gln Pro Phe Leu Leu Arg Asn Gly Ala Asn Glu Gly Phe His Glu Ala
385                 390                 395                 400

Val Gly Glu Ile Met Ser Leu Ser Ala Ala Thr Pro Lys His Leu Lys
                405                 410                 415

Ser Ile Gly Leu Leu Ser Pro Asp Phe Gln Glu Asp Asn Glu Thr Glu
                420                 425                 430

Ile Asn Phe Leu Leu Lys Gln Ala Leu Thr Ile Val Gly Thr Leu Pro
                435                 440                 445

Phe Thr Tyr Met Leu Glu Lys Trp Arg Trp Met Val Phe Lys Gly Glu
                450                 455                 460

Ile Pro Lys Asp Gln Trp Met Lys Lys Trp Trp Glu Met Lys Arg Glu
465                 470                 475                 480
```

-continued

```
Ile Val Gly Val Val Glu Pro Val Pro His Asp Glu Thr Tyr Cys Asp
            485             490                 495

Pro Ala Ser Leu Phe His Val Ser Asn Asp Tyr Ser Phe Ile Arg Tyr
            500             505                 510

Tyr Thr Arg Thr Leu Tyr Gln Phe Gln Phe Gln Glu Ala Leu Cys Gln
            515             520                 525

Ala Ala Lys His Glu Gly Pro Leu His Lys Cys Asp Ile Ser Asn Ser
        530             535             540

Thr Glu Ala Gly Gln Lys Leu Phe Asn Met Leu Arg Leu Gly Lys Ser
545             550             555             560

Glu Pro Trp Thr Leu Ala Leu Glu Asn Val Val Gly Ala Lys Asn Met
            565             570             575

Asn Val Arg Pro Leu Leu Asn Tyr Phe Glu Pro Leu Phe Thr Trp Leu
            580             585             590

Lys Asp Gln Asn Lys Asn Ser Phe Val Gly Trp Ser Thr Asp Trp Ser
            595             600             605

Pro Tyr Ala Asp Glu Pro Lys Ser Ser Asp Lys Thr His Thr Cys Pro
        610             615             620

Pro Cys Pro Ala Pro Glu Leu Leu Gly Gly Pro Ser Val Phe Leu Phe
625             630             635             640

Pro Pro Lys Pro Lys Asp Thr Leu Met Ile Ser Arg Thr Pro Glu Val
            645             650             655

Thr Cys Val Val Val Asp Val Ser His Glu Asp Pro Glu Val Lys Phe
            660             665             670

Asn Trp Tyr Val Asp Gly Val Glu Val His Asn Ala Lys Thr Lys Pro
            675             680             685

Arg Glu Glu Gln Tyr Asn Ser Thr Tyr Arg Val Val Ser Val Leu Thr
        690             695             700

Val Leu His Gln Asp Trp Leu Asn Gly Lys Glu Tyr Lys Cys Lys Val
705             710             715             720

Ser Asn Lys Ala Leu Pro Ala Pro Ile Glu Lys Thr Ile Ser Lys Ala
            725             730             735

Lys Gly Gln Pro Arg Glu Pro Gln Val Tyr Thr Leu Pro Pro Ser Arg
            740             745             750

Asp Glu Leu Thr Lys Asn Gln Val Ser Leu Thr Cys Leu Val Lys Gly
            755             760             765

Phe Tyr Pro Ser Asp Ile Ala Val Glu Trp Glu Ser Asn Gly Gln Pro
        770             775             780

Glu Asn Asn Tyr Lys Thr Thr Pro Pro Val Leu Asp Ser Asp Gly Ser
785             790             795             800

Phe Phe Leu Tyr Ser Lys Leu Thr Val Asp Lys Ser Arg Trp Gln Gln
            805             810             815

Gly Asn Val Phe Ser Cys Ser Val Met His Glu Ala Leu His Asn His
            820             825             830

Tyr Thr Gln Lys Ser Leu Ser Leu Ser Pro Gly Lys Ala Ala Ala Thr
            835             840             845

Ile Glu Glu Gln Ala Lys Thr Phe Leu Asp Lys Phe Asn His Glu Ala
        850             855             860

Glu Asp Leu Phe Tyr Gln Ser Ser Leu Ala Ser Trp Asn Tyr Asn Thr
865             870             875             880

Asn Ile Thr Glu Glu Asn Val Gln Asn Met Asn Asn Ala Gly Asp Lys
            885             890             895
```

-continued

```
Trp Ser Ala Phe Leu Lys Glu Gln Ser Thr Leu Ala Gln Met Tyr Pro
            900                 905                 910

Leu Gln Glu Ile Gln Asn Leu Thr Val Lys Leu Gln Leu Gln Ala Leu
        915                 920                 925

Gln Gln Asn Gly Ser Ser Val Leu Ser Glu Asp Lys Ser Lys Arg Leu
        930                 935             940

Asn Thr Ile Leu Asn Thr Met Ser Thr Ile Tyr Ser Thr Gly Lys Val
945                 950                 955                 960

Cys Asn Pro Asp Asn Pro Gln Glu Cys Leu Leu Leu Glu Pro Gly Leu
                965                 970                 975

Asn Glu Ile Met Ala Asn Ser Leu Asp Tyr Asn Glu Arg Leu Trp Ala
                980                 985                 990

Trp Glu Ser Trp Arg Ser Glu Val  Gly Lys Gln Leu Arg  Pro Leu Tyr
            995                 1000                1005

Glu Glu  Tyr Val Val Leu Lys  Asn Glu Met Ala Arg  Ala Asn His Tyr
        1010                1015                1020

Glu  Asp Tyr Gly Asp Tyr  Trp Arg Gly Asp Tyr  Glu Val Asn Gly Val
1025                1030                1035                1040

Asp Gly Tyr Asp Tyr  Ser Arg Gly Gln Leu  Ile Glu Asp Val Glu  His
                1045                1050                1055

Thr Phe Glu Glu  Ile Lys Pro Leu Tyr  Glu His Leu His Ala  Tyr Val
                1060                1065                1070

Arg Ala Lys  Leu Met Asn Ala Tyr  Pro Ser Tyr Ile Ser  Pro Ile Gly
            1075                1080                1085

Cys Leu  Pro Ala His Leu Leu  Gly Asp Met Trp Gly  Arg Phe Trp Thr
        1090                1095                1100

Asn  Leu Tyr Ser Leu Thr  Val Pro Phe Gly Gln  Lys Pro Asn Ile Asp
1105                1110                1115                1120

Val Thr Asp Ala Met  Val Asp Gln Ala Trp  Asp Ala Gln Arg Ile  Phe
                1125                1130                1135

Lys Glu Ala Glu  Lys Phe Phe Val Ser  Val Gly Leu Pro Asn  Met Thr
                1140                1145                1150

Gln Gly Phe  Trp Glu Asn Ser Met  Leu Thr Asp Pro Gly  Asn Val Gln
            1155                1160                1165

Lys Ala  Val Cys His Pro Thr  Ala Trp Asp Leu Gly  Lys Gly Asp Phe
        1170                1175                1180

Arg  Ile Leu Met Cys Thr  Lys Val Thr Met Asp  Asp Phe Leu Thr Ala
1185                1190                1195                1200

His Asn Glu Met Gly  Asn Ile Gln Tyr Asp  Met Ala Tyr Ala Ala  Gln
                1205                1210                1215

Pro Phe Leu Leu  Arg Asn Gly Ala Asn  Glu Gly Phe His Glu  Ala Val
                1220                1225                1230

Gly Glu Ile  Met Ser Leu Ser Ala  Ala Thr Pro Lys His  Leu Lys Ser
            1235                1240                1245

Ile Gly  Leu Leu Ser Pro Asp  Phe Gln Glu Asp Asn  Glu Thr Glu Ile
        1250                1255                1260

Asn  Phe Leu Leu Lys Gln  Ala Leu Thr Ile Val  Gly Thr Leu Pro Phe
1265                1270                1275                1280

Thr Tyr Met Leu Glu  Lys Trp Arg Trp Met  Val Phe Lys Gly Glu  Ile
                1285                1290                1295

Pro Lys Asp Gln  Trp Met Lys Lys Trp  Trp Glu Met Lys Arg  Glu Ile
                1300                1305                1310

Val Gly Val  Val Glu Pro Val Pro  His Asp Glu Thr Tyr  Cys Asp Pro
```

-continued

```
            1315                 1320                 1325

Ala Ser  Leu Phe His Val Ser  Asn Asp Tyr Ser Phe  Ile Arg Tyr Tyr
    1330                 1335                 1340

Thr  Arg Thr Leu Tyr Gln  Phe Gln Phe Gln Glu  Ala Leu Cys Gln Ala
1345                 1350                 1355                 1360

Ala Lys His Glu Gly  Pro Leu His Lys Cys  Asp Ile Ser Asn Ser  Thr
                1365                 1370                 1375

Glu Ala Gly Gln  Lys Leu Phe Asn Met  Leu Arg Leu Gly Lys  Ser Glu
                1380                 1385                 1390

Pro Trp Thr  Leu Ala Leu Glu Asn  Val Val Gly Ala Lys  Asn Met Asn
                1395                 1400                 1405

Val Arg  Pro Leu Leu Asn Tyr  Phe Glu Pro Leu Phe  Thr Trp Leu Lys
        1410                 1415                 1420

Asp  Gln Asn Lys Asn Ser  Phe Val Gly Trp Ser  Thr Asp Trp Ser Pro
1425                 1430                 1435                 1440

Tyr Ala Asp

<210> SEQ ID NO 14
<211> LENGTH: 1440
<212> TYPE: PRT
<213> ORGANISM: Artificial Sequence
<220> FEATURE:
<223> OTHER INFORMATION: the sequence is synthesized

<400> SEQUENCE: 14

Met Pro Leu Leu Leu Leu Leu Pro Leu Leu Trp Ala Gly Ala Leu Ala
1                5                   10                  15

Thr Ile Glu Glu Gln Ala Lys Thr Phe Leu Asp Lys Phe Asn His Glu
                20                  25                  30

Ala Glu Asp Leu Phe Tyr Gln Ser Ser Leu Ala Ser Trp Asn Tyr Asn
                35                  40                  45

Thr Asn Ile Thr Glu Glu Asn Val Gln Asn Met Asn Asn Ala Gly Asp
    50                  55                  60

Lys Trp Ser Ala Phe Leu Lys Glu Gln Ser Thr Leu Ala Gln Met Tyr
65                  70                  75                  80

Pro Leu Gln Glu Ile Gln Asn Leu Thr Val Lys Leu Gln Leu Gln Ala
                85                  90                  95

Leu Gln Gln Asn Gly Ser Ser Val Leu Ser Glu Asp Lys Ser Lys Arg
                100                 105                 110

Leu Asn Thr Ile Leu Asn Thr Met Ser Thr Ile Tyr Ser Thr Gly Lys
                115                 120                 125

Val Cys Asn Pro Asp Asn Pro Gln Glu Cys Leu Leu Leu Glu Pro Gly
    130                 135                 140

Leu Asn Glu Ile Met Ala Asn Ser Leu Asp Tyr Asn Glu Arg Leu Trp
145                 150                 155                 160

Ala Trp Glu Ser Trp Arg Ser Glu Val Gly Lys Gln Leu Arg Pro Leu
                165                 170                 175

Tyr Glu Glu Tyr Val Val Leu Lys Asn Glu Met Ala Arg Ala Asn His
                180                 185                 190

Tyr Glu Asp Tyr Gly Asp Tyr Trp Arg Gly Asp Tyr Glu Val Asn Gly
                195                 200                 205

Val Asp Gly Tyr Asp Tyr Ser Arg Gly Gln Leu Ile Glu Asp Val Glu
    210                 215                 220

His Thr Phe Glu Glu Ile Lys Pro Leu Tyr Glu His Leu His Ala Tyr
225                 230                 235                 240
```

-continued

```
Val Arg Ala Lys Leu Met Asn Ala Tyr Pro Ser Tyr Ile Ser Pro Ile
            245                 250                 255

Gly Cys Leu Pro Ala His Leu Leu Gly Asp Met Trp Gly Arg Phe Trp
            260                 265                 270

Thr Asn Leu Tyr Ser Leu Thr Val Pro Phe Gly Gln Lys Pro Asn Ile
            275                 280                 285

Asp Val Thr Asp Ala Met Val Asp Gln Ala Trp Asp Ala Gln Arg Ile
            290                 295                 300

Phe Lys Glu Ala Glu Lys Phe Phe Val Ser Val Gly Leu Pro Asn Met
305                 310                 315                 320

Thr Gln Gly Phe Trp Glu Asn Ser Met Leu Thr Asp Pro Gly Asn Val
            325                 330                 335

Gln Lys Ala Val Cys His Pro Thr Ala Trp Asp Leu Gly Lys Gly Asp
            340                 345                 350

Phe Arg Ile Leu Met Cys Thr Lys Val Thr Met Asp Asp Phe Leu Thr
            355                 360                 365

Ala His Asn Glu Met Gly Asn Ile Gln Tyr Asp Met Ala Tyr Ala Ala
            370                 375                 380

Gln Pro Phe Leu Leu Arg Asn Gly Ala Asn Glu Gly Phe His Glu Ala
385                 390                 395                 400

Val Gly Glu Ile Met Ser Leu Ser Ala Ala Thr Pro Lys His Leu Lys
            405                 410                 415

Ser Ile Gly Leu Leu Ser Pro Asp Phe Gln Glu Asp Asn Glu Thr Glu
            420                 425                 430

Ile Asn Phe Leu Leu Lys Gln Ala Leu Thr Ile Val Gly Thr Leu Pro
            435                 440                 445

Phe Thr Tyr Met Leu Glu Lys Trp Arg Trp Met Val Phe Lys Gly Glu
            450                 455                 460

Ile Pro Lys Asp Gln Trp Met Lys Lys Trp Trp Glu Met Lys Arg Glu
465                 470                 475                 480

Ile Val Gly Val Val Glu Pro Val Pro His Asp Glu Thr Tyr Cys Asp
            485                 490                 495

Pro Ala Ser Leu Phe His Val Ser Asn Asp Tyr Ser Phe Ile Arg Tyr
            500                 505                 510

Tyr Thr Arg Thr Leu Tyr Gln Phe Gln Phe Gln Glu Ala Leu Cys Gln
            515                 520                 525

Ala Ala Lys His Glu Gly Pro Leu His Lys Cys Asp Ile Ser Asn Ser
            530                 535                 540

Thr Glu Ala Gly Gln Lys Leu Phe Asn Met Leu Arg Leu Gly Lys Ser
545                 550                 555                 560

Glu Pro Trp Thr Leu Ala Leu Glu Asn Val Val Gly Ala Lys Asn Met
            565                 570                 575

Asn Val Arg Pro Leu Leu Asn Tyr Phe Glu Pro Leu Phe Thr Trp Leu
            580                 585                 590

Lys Asp Gln Asn Lys Asn Ser Phe Val Gly Trp Ser Thr Asp Trp Ser
            595                 600                 605

Pro Tyr Ala Asp Thr Ile Glu Glu Gln Ala Lys Thr Phe Leu Asp Lys
            610                 615                 620

Phe Asn His Glu Ala Glu Asp Leu Phe Tyr Gln Ser Ser Leu Ala Ser
625                 630                 635                 640

Trp Asn Tyr Asn Thr Asn Ile Thr Glu Glu Asn Val Gln Asn Met Asn
            645                 650                 655
```

```
Asn Ala Gly Asp Lys Trp Ser Ala Phe Leu Lys Glu Gln Ser Thr Leu
            660             665             670

Ala Gln Met Tyr Pro Leu Gln Glu Ile Gln Asn Leu Thr Val Lys Leu
            675             680             685

Gln Leu Gln Ala Leu Gln Gln Asn Gly Ser Ser Val Leu Ser Glu Asp
            690             695             700

Lys Ser Lys Arg Leu Asn Thr Ile Leu Asn Thr Met Ser Thr Ile Tyr
705             710             715             720

Ser Thr Gly Lys Val Cys Asn Pro Asp Asn Pro Gln Glu Cys Leu Leu
                725             730             735

Leu Glu Pro Gly Leu Asn Glu Ile Met Ala Asn Ser Leu Asp Tyr Asn
            740             745             750

Glu Arg Leu Trp Ala Trp Glu Ser Trp Arg Ser Glu Val Gly Lys Gln
            755             760             765

Leu Arg Pro Leu Tyr Glu Glu Tyr Val Val Leu Lys Asn Glu Met Ala
            770             775             780

Arg Ala Asn His Tyr Glu Asp Tyr Gly Asp Tyr Trp Arg Gly Asp Tyr
785             790             795             800

Glu Val Asn Gly Val Asp Gly Tyr Asp Tyr Ser Arg Gly Gln Leu Ile
                805             810             815

Glu Asp Val Glu His Thr Phe Glu Glu Ile Lys Pro Leu Tyr Glu His
            820             825             830

Leu His Ala Tyr Val Arg Ala Lys Leu Met Asn Ala Tyr Pro Ser Tyr
            835             840             845

Ile Ser Pro Ile Gly Cys Leu Pro Ala His Leu Leu Gly Asp Met Trp
            850             855             860

Gly Arg Phe Trp Thr Asn Leu Tyr Ser Leu Thr Val Pro Phe Gly Gln
865             870             875             880

Lys Pro Asn Ile Asp Val Thr Asp Ala Met Val Asp Gln Ala Trp Asp
                885             890             895

Ala Gln Arg Ile Phe Lys Glu Ala Glu Lys Phe Phe Val Ser Val Gly
                900             905             910

Leu Pro Asn Met Thr Gln Gly Phe Trp Glu Asn Ser Met Leu Thr Asp
            915             920             925

Pro Gly Asn Val Gln Lys Ala Val Cys His Pro Thr Ala Trp Asp Leu
            930             935             940

Gly Lys Gly Asp Phe Arg Ile Leu Met Cys Thr Lys Val Thr Met Asp
945             950             955             960

Asp Phe Leu Thr Ala His Asn Glu Met Gly Asn Ile Gln Tyr Asp Met
                965             970             975

Ala Tyr Ala Ala Gln Pro Phe Leu Leu Arg Asn Gly Ala Asn Glu Gly
                980             985             990

Phe His Glu Ala Val Gly Glu Ile  Met Ser Leu Ser Ala  Ala Thr Pro
            995             1000             1005

Lys His  Leu Lys Ser Ile Gly  Leu Leu Ser Pro Asp  Phe Gln Glu Asp
            1010             1015             1020

Asn  Glu Thr Glu Ile Asn  Phe Leu Leu Lys Gln  Ala Leu Thr Ile Val
1025             1030             1035             1040

Gly Thr Leu Pro Phe  Thr Tyr Met Leu Glu  Lys Trp Arg Trp Met  Val
                1045             1050             1055

Phe Lys Gly Glu  Ile Pro Lys Asp Gln  Trp Met Lys Lys Trp  Trp Glu
            1060             1065             1070

Met Lys Arg  Glu Ile Val Gly Val  Val Glu Pro Val Pro  His Asp Glu
```

-continued

```
            1075              1080              1085

Thr Tyr  Cys Asp Pro Ala Ser  Leu Phe His Val Ser  Asn Asp Tyr Ser
    1090              1095              1100

Phe  Ile Arg Tyr Tyr Thr  Arg Thr Leu Tyr Gln  Phe Gln Phe Gln Glu
1105              1110              1115              1120

Ala Leu Cys Gln Ala  Ala Lys His Glu Gly  Pro Leu His Lys Cys  Asp
              1125              1130              1135

Ile Ser Asn Ser  Thr Glu Ala Gly Gln  Lys Leu Phe Asn Met  Leu Arg
              1140              1145              1150

Leu Gly Lys  Ser Glu Pro Trp Thr  Leu Ala Leu Glu Asn  Val Val Gly
          1155              1160              1165

Ala Lys  Asn Met Asn Val Arg  Pro Leu Leu Asn Tyr  Phe Glu Pro Leu
    1170              1175              1180

Phe  Thr Trp Leu Lys Asp  Gln Asn Lys Asn Ser  Phe Val Gly Trp Ser
1185              1190              1195              1200

Thr Asp Trp Ser Pro  Tyr Ala Asp Glu Pro  Lys Ser Ser Asp Lys  Thr
              1205              1210              1215

His Thr Cys Pro  Pro Cys Pro Ala Pro  Glu Leu Leu Gly Gly  Pro Ser
              1220              1225              1230

Val Phe Leu  Phe Pro Pro Lys Pro  Lys Asp Thr Leu Met  Ile Ser Arg
          1235              1240              1245

Thr Pro  Glu Val Thr Cys Val  Val Val Asp Val Ser  His Glu Asp Pro
    1250              1255              1260

Glu  Val Lys Phe Asn Trp  Tyr Val Asp Gly Val  Glu Val His Asn Ala
1265              1270              1275              1280

Lys Thr Lys Pro Arg  Glu Glu Gln Tyr Asn  Ser Thr Tyr Arg Val  Val
              1285              1290              1295

Ser Val Leu Thr  Val Leu His Gln Asp  Trp Leu Asn Gly Lys  Glu Tyr
          1300              1305              1310

Lys Cys Lys  Val Ser Asn Lys Ala  Leu Pro Ala Pro Ile  Glu Lys Thr
          1315              1320              1325

Ile Ser  Lys Ala Lys Gly Gln  Pro Arg Glu Pro Gln  Val Tyr Thr Leu
    1330              1335              1340

Pro  Pro Ser Arg Asp Glu  Leu Thr Lys Asn Gln  Val Ser Leu Thr Cys
1345              1350              1355              1360

Leu Val Lys Gly Phe  Tyr Pro Ser Asp Ile  Ala Val Glu Trp Glu  Ser
              1365              1370              1375

Asn Gly Gln Pro  Glu Asn Asn Tyr Lys  Thr Thr Pro Pro Val  Leu Asp
              1380              1385              1390

Ser Asp Gly  Ser Phe Phe Leu Tyr  Ser Lys Leu Thr Val  Asp Lys Ser
          1395              1400              1405

Arg Trp  Gln Gln Gly Asn Val  Phe Ser Cys Ser Val  Met His Glu Ala
    1410              1415              1420

Leu  His Asn His Tyr Thr  Gln Lys Ser Leu Ser  Leu Ser Pro Gly Lys
1425              1430              1435              1440
```

<210> SEQ ID NO 15
<211> LENGTH: 18
<212> TYPE: PRT
<213> ORGANISM: Artificial Sequence
<220> FEATURE:
<223> OTHER INFORMATION: the sequence is synthesized

<400> SEQUENCE: 15

Pro Thr Leu Tyr Asn Val Ser Leu Val Met Ser Asp Thr Ala Gly Thr

-continued

```
1                5                10               15

Cys Tyr

<210> SEQ ID NO 16
<211> LENGTH: 18
<212> TYPE: PRT
<213> ORGANISM: Artificial Sequence
<220> FEATURE:
<223> OTHER INFORMATION: the sequence is synthesized

<400> SEQUENCE: 16

Pro Thr His Val Asn Val Ser Val Val Met Ala Glu Val Asp Gly Thr
1                5                10               15

Cys Tyr

<210> SEQ ID NO 17
<211> LENGTH: 21
<212> TYPE: PRT
<213> ORGANISM: Artificial Sequence
<220> FEATURE:
<223> OTHER INFORMATION: the sequence is synthesized

<400> SEQUENCE: 17

Thr Gly Lys Pro Thr Leu Tyr Asn Val Ser Leu Val Met Ser Asp Thr
1                5                10               15

Ala Gly Thr Cys Tyr
            20

<210> SEQ ID NO 18
<211> LENGTH: 862
<212> TYPE: PRT
<213> ORGANISM: Artificial Sequence
<220> FEATURE:
<223> OTHER INFORMATION: the sequence is synthesized

<400> SEQUENCE: 18

Met Pro Leu Leu Leu Leu Leu Pro Leu Leu Trp Ala Gly Ala Leu Ala
1                5                10               15

Thr Ile Glu Glu Gln Ala Lys Thr Phe Leu Asp Lys Phe Asn His Glu
            20               25               30

Ala Glu Asp Leu Phe Tyr Gln Ser Ser Leu Ala Ser Trp Asn Tyr Asn
         35               40               45

Thr Asn Ile Thr Glu Glu Asn Val Gln Asn Met Asn Asn Ala Gly Asp
      50               55               60

Lys Trp Ser Ala Phe Leu Lys Glu Gln Ser Thr Leu Ala Gln Met Tyr
65               70               75               80

Pro Leu Gln Glu Ile Gln Asn Leu Thr Val Lys Leu Gln Leu Gln Ala
            85               90               95

Leu Gln Gln Asn Gly Ser Ser Val Leu Ser Glu Asp Lys Ser Lys Arg
            100              105              110

Leu Asn Thr Ile Leu Asn Thr Met Ser Thr Ile Tyr Ser Thr Gly Lys
         115              120              125

Val Cys Asn Pro Asp Asn Pro Gln Glu Cys Leu Leu Leu Glu Pro Gly
      130              135              140

Leu Asn Glu Ile Met Ala Asn Ser Leu Asp Tyr Asn Glu Arg Leu Trp
145              150              155              160

Ala Trp Glu Ser Trp Arg Ser Glu Val Gly Lys Gln Leu Arg Pro Leu
            165              170              175

Tyr Glu Glu Tyr Val Val Leu Lys Asn Glu Met Ala Arg Ala Asn His
```

-continued

```
                180              185              190
Tyr Glu Asp Tyr Gly Asp Tyr Trp Arg Gly Asp Tyr Glu Val Asn Gly
        195              200              205

Val Asp Gly Tyr Asp Tyr Ser Arg Gly Gln Leu Ile Glu Asp Val Glu
        210              215              220

His Thr Phe Glu Glu Ile Lys Pro Leu Tyr Glu His Leu His Ala Tyr
225              230              235              240

Val Arg Ala Lys Leu Met Asn Ala Tyr Pro Ser Tyr Ile Ser Pro Ile
            245              250              255

Gly Cys Leu Pro Ala His Leu Leu Gly Asp Met Trp Gly Arg Phe Trp
            260              265              270

Thr Asn Leu Tyr Ser Leu Thr Val Pro Phe Gly Gln Lys Pro Asn Ile
            275              280              285

Asp Val Thr Asp Ala Met Val Asp Gln Ala Trp Asp Ala Gln Arg Ile
        290              295              300

Phe Lys Glu Ala Glu Lys Phe Phe Val Ser Val Gly Leu Pro Asn Met
305              310              315              320

Thr Gln Gly Phe Trp Glu Asn Ser Met Leu Thr Asp Pro Gly Asn Val
            325              330              335

Gln Lys Ala Val Cys His Pro Thr Ala Trp Asp Leu Gly Lys Gly Asp
            340              345              350

Phe Arg Ile Leu Met Cys Thr Lys Val Thr Met Asp Asp Phe Leu Thr
            355              360              365

Ala His Asn Glu Met Gly Asn Ile Gln Tyr Asp Met Ala Tyr Ala Ala
        370              375              380

Gln Pro Phe Leu Leu Arg Asn Gly Ala Asn Glu Gly Phe His Glu Ala
385              390              395              400

Val Gly Glu Ile Met Ser Leu Ser Ala Ala Thr Pro Lys His Leu Lys
            405              410              415

Ser Ile Gly Leu Leu Ser Pro Asp Phe Gln Glu Asp Asn Glu Thr Glu
            420              425              430

Ile Asn Phe Leu Leu Lys Gln Ala Leu Thr Ile Val Gly Thr Leu Pro
            435              440              445

Phe Thr Tyr Met Leu Glu Lys Trp Arg Trp Met Val Phe Lys Gly Glu
        450              455              460

Ile Pro Lys Asp Gln Trp Met Lys Lys Trp Trp Glu Met Lys Arg Glu
465              470              475              480

Ile Val Gly Val Val Glu Pro Val Pro His Asp Glu Thr Tyr Cys Asp
            485              490              495

Pro Ala Ser Leu Phe His Val Ser Asn Asp Tyr Ser Phe Ile Arg Tyr
            500              505              510

Tyr Thr Arg Thr Leu Tyr Gln Phe Gln Phe Gln Glu Ala Leu Cys Gln
            515              520              525

Ala Ala Lys His Glu Gly Pro Leu His Lys Cys Asp Ile Ser Asn Ser
        530              535              540

Thr Glu Ala Gly Gln Lys Leu Phe Asn Met Leu Arg Leu Gly Lys Ser
545              550              555              560

Glu Pro Trp Thr Leu Ala Leu Glu Asn Val Val Gly Ala Lys Asn Met
            565              570              575

Asn Val Arg Pro Leu Leu Asn Tyr Phe Glu Pro Leu Phe Thr Trp Leu
            580              585              590

Lys Asp Gln Asn Lys Asn Ser Phe Val Gly Trp Ser Thr Asp Trp Ser
            595              600              605
```

```
Pro Tyr Ala Asp Glu Pro Lys Ser Ser Asp Lys Thr His Thr Cys Pro
    610             615             620

Pro Cys Pro Ala Pro Glu Leu Leu Gly Gly Pro Ser Val Phe Leu Phe
625             630             635             640

Pro Pro Lys Pro Lys Asp Thr Leu Met Ile Ser Arg Thr Pro Glu Val
        645             650             655

Thr Cys Val Val Val Asp Val Ser His Glu Asp Pro Glu Val Lys Phe
        660             665             670

Asn Trp Tyr Val Asp Gly Val Glu Val His Asn Ala Lys Thr Lys Pro
        675             680             685

Arg Glu Glu Gln Tyr Asn Ser Thr Tyr Arg Val Val Ser Val Leu Thr
    690             695             700

Val Cys His Gln Asp Trp Leu Asn Gly Lys Glu Tyr Lys Cys Lys Val
705             710             715             720

Ser Asn Lys Ala Leu Pro Ala Pro Ile Glu Lys Thr Ile Ser Lys Ala
        725             730             735

Lys Gly Gln Pro Arg Glu Pro Gln Val Tyr Thr Leu Pro Pro Ser Arg
        740             745             750

Asp Glu Leu Thr Lys Asn Gln Val Ser Leu Thr Cys Leu Val Lys Gly
    755             760             765

Phe Tyr Pro Ser Asp Ile Ala Val Glu Trp Glu Ser Asn Gly Gln Pro
    770             775             780

Glu Asn Asn Tyr Lys Thr Thr Pro Pro Val Leu Asp Ser Asp Gly Ser
785             790             795             800

Phe Phe Leu Tyr Ser Lys Leu Thr Val Asp Lys Ser Arg Trp Gln Gln
        805             810             815

Gly Asn Val Phe Ser Cys Ser Val Met His Glu Ala Leu His Asn His
        820             825             830

Tyr Thr Gln Lys Ser Leu Ser Leu Ser Thr Gly Lys Pro Thr Leu Tyr
        835             840             845

Asn Val Ser Leu Val Met Ser Asp Thr Ala Gly Thr Cys Tyr
    850             855             860
```